US011446307B2

(12) United States Patent
Litzinger et al.

(10) Patent No.: US 11,446,307 B2
(45) Date of Patent: Sep. 20, 2022

(54) CRYSTALLINE FORMS OF A DEOXYCYTIDINE KINASE INHIBITOR AND USES THEREOF

(71) Applicant: Trethera Corporation, Sherman Oaks, CA (US)

(72) Inventors: David Litzinger, Poway, CA (US); Kenneth A. Schultz, Sherman Oaks, CA (US)

(73) Assignee: TRETHERA CORPORATION, Sherman Oaks, CA (US)

( * ) Notice: Subject to any disclaimer, the term of this patent is extended or adjusted under 35 U.S.C. 154(b) by 0 days.

(21) Appl. No.: 17/576,128

(22) Filed: Jan. 14, 2022

(65) Prior Publication Data

US 2022/0135555 A1 May 5, 2022

Related U.S. Application Data

(63) Continuation of application No. 17/516,420, filed on Nov. 1, 2021.

(60) Provisional application No. 63/108,803, filed on Nov. 2, 2020, provisional application No. 63/190,107, filed on May 18, 2021.

(51) Int. Cl.
*A61K 31/5377* (2006.01)
*C07D 417/12* (2006.01)
*A61P 25/00* (2006.01)
*A61P 37/06* (2006.01)

(52) U.S. Cl.
CPC .......... *A61K 31/5377* (2013.01); *A61P 25/00* (2018.01); *A61P 37/06* (2018.01); *C07D 417/12* (2013.01); *C07B 2200/13* (2013.01)

(58) Field of Classification Search
CPC ............................ C07D 417/12; A61P 25/00
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,033,252 A | 7/1991 | Carter | |
| 5,052,558 A | 10/1991 | Carter | |
| 5,212,162 A | 5/1993 | Missel et al. | |
| 5,323,907 A | 6/1994 | Kalvelage | |
| 5,403,841 A | 4/1995 | Lang et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koster | |
| 8,101,740 B2 | 1/2012 | Radu et al. | |
| 9,598,404 B2 | 3/2017 | Radu et al. | |
| 9,688,673 B2 | 6/2017 | Radu et al. | |
| 9,981,961 B2 | 5/2018 | Radu et al. | |
| 10,570,124 B2 * | 2/2020 | Radu ....................... | A61P 35/00 |
| 2007/0100137 A1 | 5/2007 | Dellinger et al. | |
| 2008/0146571 A1 | 6/2008 | Augeri et al. | |
| 2008/0182847 A1 | 7/2008 | Augeri et al. | |
| 2009/0163545 A1 | 6/2009 | Goldfarb | |
| 2010/0022544 A1 | 1/2010 | Nell et al. | |
| 2010/0292253 A1 | 11/2010 | Trullinger et al. | |
| 2012/0289545 A1 | 11/2012 | Lu et al. | |
| 2013/0089626 A1 | 4/2013 | Pollard et al. | |
| 2013/0336883 A1 | 12/2013 | Radu et al. | |
| 2019/0000850 A1 | 1/2019 | Radu et al. | |
| 2019/0016714 A1 | 1/2019 | Radu et al. | |
| 2022/0133735 A1 | 5/2022 | Litzinger et al. | |

FOREIGN PATENT DOCUMENTS

| | | |
|---|---|---|
| WO | WO-02059098 A1 | 8/2002 |
| WO | WO-03072100 A1 | 9/2003 |
| WO | WO-03072102 A1 | 9/2003 |
| WO | WO-2004092131 A1 | 10/2004 |
| WO | WO-2007039171 A1 | 4/2007 |
| WO | WO-2008076778 A1 | 6/2008 |
| WO | WO-2009038795 A2 | 3/2009 |
| WO | WO-2012122368 A1 | 9/2012 |
| WO | WO-2015023776 A2 | 2/2015 |
| WO | WO-2015023776 A3 | 11/2015 |
| WO | WO-2016130562 A2 | 8/2016 |
| WO | WO-2016130581 A2 | 8/2016 |
| WO | WO-2016130581 A3 | 10/2016 |
| WO | WO-2017120585 A1 | 7/2017 |
| WO | WO-2016130581 A8 | 8/2017 |
| WO | WO-2017204262 A1 | 11/2017 |
| WO | WO-2018237084 A1 | 12/2018 |
| WO | WO-2019165073 A1 | 8/2019 |
| WO | WO-2022094409 A1 | 5/2022 |

OTHER PUBLICATIONS

Poddar et al. (2020).*
McMahon et al. (2000).*
Pinedo et al. (2000).*
Co-pending U.S. Appl. No. 17/516,420, inventors Litzinger; David et al., filed Nov. 1, 2021.
PCT/US2021/057584 International Search Report and Written Opinion dated Feb. 25, 2022.
Abdel-Fatah et al. Untangling the ATR-CHEK1 network for prognostication, prediction and therapeutic target validation in breast cancer. Mol Oncol. 9(3):569-85. (2014).
Al-Minawi et al. The ERCC1/XPF endonuclease is required for efficient single-strand annealing and gene conversion in mammalian cells. Nucleic Acids Res. 36(1):1-9 (2008).
Al-Muhammed et al. In-vivo studies on dexamethasone sodium phosphate liposomes. J Microencapsul. 13(3):293-306 (1996).

(Continued)

*Primary Examiner* — Paul V Ward
(74) *Attorney, Agent, or Firm* — Wilson Sonsini Goodrich & Rosati

(57) ABSTRACT

Described herein are crystalline forms of compounds that are deoxycytidine kinase (dCK) inhibitors, methods of making such crystalline forms, pharmaceutical compositions and medicaments comprising such crystalline forms, and methods of using such crystalline forms in the treatment of conditions, diseases, or disorders that would benefit from modulation of deoxycytidine kinase (dCK) activity.

23 Claims, 27 Drawing Sheets

(56) References Cited

OTHER PUBLICATIONS

Arner et al. Mammalian Deoxyribonucleoside Kinases. Pharmac. Ther. 67:155-186 (1995).
Arpaia et al. Mitochondrial basis for immune deficiency. Evidence from purine nucleoside phosphorylase-deficient mice. J Exper Med 191:2197-2208 (2000).
Audeh et al. Oral poly(ADP-ribose) polymerase inhibitor olaparib in patients with BRCA1 or BRCA2 mutations and recurrent ovarian cancer: a proof-of-concept trial. Lancet 376:245-251 (2010).
Austin et al. Nucleoside salvage pathway kinases regulate hematopoiesis by linking nucleotide metabolism with replication stress. J Exp Med 209(12):2215-2228 (2012).
Aye et al. Mechanistic studies of semicarbazone triapine targeting human ribonucleotide reductase in vitro and in mammalian cells: tyrosyl radical quenching not involving reactive oxygen species. J Biol Chem. 287(42):35768-35778 (20120.
Baron et al. Study of the thymocyte cell cycle by bivariate analysis of incorporated bromodeoxyuridine and DNA content. EP J Immunol 20:1231-1236 (1990).
Bartek et al. Thresholds of replication stress signaling in cancer development and treatment. Nat Struct Mol Biol 19(1):5-7 (2012).
Begg et al. A method to measure the duration of DNA synthesis and the potential doubling time from a single sample. Cytometry 6:620-626 (1985).
Berge et al. Pharmaceutical Salts. Journal of Pharmaceutical Sciences 66(1):1-19 (Jan. 1977).
Beyaert et al. A crucial role for ATR in the regulation of deoxycytidine kinase activity. Biochem Pharmacol 100:40-50 (2015).
Bhattacharyya. Application of Positron Emission Tomography in Drug Development. Biochem. Pharmacol. 1:1000e128 (2012).
Bianchi et al. Changes of deoxyribonucleoside triphosphate pools induced by hydroxyurea and their relation to DNA synthesis. The Journal of biological chemistry 261:16037-16042 (1986).
Bjursell et al. Deoxyribonucleoside triphosphate pools of normal and transformed baby-hamster-kidney cells. Eur J Biochem 29:348-352 (1972).
Bjursell et al. Effects of thymidine on deoxyribonucleoside triphosphate pools and deoxyribonucleic acid synthesis in Chinese hamster ovary cells. J Biol Chem 248:3904-3909 (1973).
Blackwood et al. Combination drug scheduling defines a "window of opportunity" for chemopotentiation of gemcitabine by an orally bioavailable, selective ChK1 inhibitor, GNE-900. Mol Cancer Ther. 12(10):1968-1980 (2013).
Blasina et al. Breaching the DNA damage checkpoint via PF-00477736, a novel smallmolecule inhibitor of checkpoint kinase 1. Mol Cancer Ther. 7(8):2394-2404 (2008).
Bolderson et al. ATM is required for the cellular response to thymidine induced replication fork stress. Hum Mol Genet 13:2937-2945 (2004).
Borst et al. Targeted radiosensitization by the Chk1 inhibitor SAR-020106. Int J Radiat Oncol Biol Phys. 85(4):1110-1118 (2013).
Boulos et al. Chemotherapeutic agents circumvent emergence of dasatinib-resistant BCR-ABL kinase mutations in a precise mouse model of Philadelphia chromosome-positive acute lymphoblastic leukemia. Blood 117(13):3585-3595 (2011).
Bourne. Boomer, a simulation and modeling program for pharmacokinetic and pharmacodynamic data analysis. Comput Methods Programs Biomed 29:191-5 (1989).
Bourne. Multi-Forte, a microcomputer program for modelling and simulation of pharmacokinetic data. Comput Methods Programs Biomed 23:277-81 (1986).
Bristow et al. Hepatic oxygen and glucose metabolism in the fetal lamb. Response to hypoxia. J Clin Invest 71:1047-1061 (1983).
Brooks et al. A potent Chk1 inhibitor is selectively cytotoxic in melanomas with high levels of replicative stress. Oncogene. 32(6):788-796 (2013).
Bryant et al. Chk1 inhibition as a novel therapeutic strategy for treating triple-negative breast and ovarian cancers. BMC Cancer. 14:570 (2014).
Bryant et al. Inhibition of the checkpoint kinase Chk1 induces DNA damage and cell death in human Leukemia and Lymphoma cells. Mol Cancer. 13:147 (2014).
Busby et al. The radiosensitizing agent 7-hydroxystaurosporine (UCN-01) inhibits the DNA damage checkpoint kinase hChk1. Cancer Res. 60(8):2108-2112 (2000).
Calvo et al. Preclinical analyses and phase I evaluation of LY2603618 administered in combination with pemetrexed and cisplatin in patients with advanced cancer. Invest New Drugs.32(5):955-968 (2014).
Cancer Genome Atlas Research Network. Integrated genomic analyses of ovarian carcinoma. Nature 474:609-615 (2011).
Cancer [online], [retrieved on Jul. 6, 2007] Retrieved from the Internet, URL: http://www.nlm.nih.gov/medlineplus/cancer.html (2007).
Cannistra. Cancer of the ovary. N Engl J Med 351:2519-2529 (2004).
Carbonaro et al. In vivo transduction by intravenous injection of a lentiviral vector expressing human ADA into neonatal ADA gene knockout mice: a novel form of enzyme replacement therapy for ADA deficiency. Mol Ther 13:1110-1120 (2006).
Carbonaro et al. Neonatal bone marrow transplantation of ADA-deficient SCID mice results in immunologic reconstitution despite low levels of engraftment and an absence of selective donor T lymphoid expansion. Blood 111:5745-5754 (2008).
Chaudhuri et al. CHK1 and WEE1 inhibition combine synergistically to enhance therapeutic efficacy in acute myeloid leukemia ex vivo. Haematologica. 99(4):688-696 (2014).
Chauhan et al. Heterocyclic o-xylylenes; thiazole, oxazole and imidazole analogues. Tetrahedron Letters 31:1487-1490 (1990).
Chitambar et al. A novel gallium compound synergistically enhances bortezomib-induced apoptosis in mantle cell lymphoma cells. Leuk Res. 34(7):950-953 (2010).
Chitambar et al. Development of gallium compounds for treatment of lymphoma: gallium maltolate, a novel hydroxypyrone gallium compound, induces apoptosis and circumvents lymphoma cell resistance to gallium nitrate. J Pharmacol Exp Ther. 322(3):1228-1236 (2007).
Chiuten et al. Clinical phase I-II and pharmacokinetic study of high-dose thymidine given by continuous intravenous infusion. Cancer Res. 40:818-22 (1980).
Choi et al. A deficiency in nucleoside salvage impairs murine lymphocyte development, homeostasis, and survival. J Immunol 188:3920-7 (2012).
Chonn et al. Recent advances in liposomal drug-delivery systems. Curr Opin Biotechnol. 6(6):698-708 (1995).
Chottiner et al. Cloning and Expression of Human Deoxycytidine Kinase cDNA. PNAS USA 88:1531-1535 (1991).
Ciofani et al. Determining gammadelta versus alphass T cell development. Nat Rev Immunol 10:657-663 (2010).
Cohen et al. Simultaneous analysis of eight nucleoside triphosphates in cell lines by liquid chromatography coupled with tandem mass spectrometry. J Chromatogr B Analyt Technol Biomed Life Sci. 877:3831-40 (2009).
Cole et al. RNAi screen of the protein kinome identifies checkpoint kinase 1 (CHKI) as a therapeutic target in neuroblastoma. PNAS USA 108(8):3336-3341 (2011).
Collery et al. Gallium in cancer treatment. Crit Rev Oncol Hematol. 42(3):283-296 (2002).
Converso et al. Development of thioquinazolinones, allosteric Chk1 kinase inhibitors. Bioorg Med Chem Lett. 19(4):1240-1244 (2009).
Corey et al. Highly enantioselective borane reduction of ketones catalyzed by chiral oxazaborolidines. Mechanism and synthetic implications. J. Am. Chem. Soc. 109:5551-5553 (1987).
Crane et al. Reactions of Some Ortho and Para Halogenated Aromatic Nitriles with Ethylenediamine: Selective Synthesis of Imidazolines. Tetrahedron 60:5325-5330 (2004).
Csapo et al. Activation of deoxycytidine kinase by gamma-irradiation and inactivation by hyperosmotic shock in human lymphocytes. Biochem Pharmacol 65(12):2031-2039 (2003).
Czernin et al. PET/CT Imaging: The Incremental Value of Assessing the Glucose Metabolic Phenotype and the Structure of Cancers in a Single Examination. Eur. J. Radiol. 73:470-480 (2010).

(56) References Cited

OTHER PUBLICATIONS

Dai et al. The novel Chk1 inhibitor MK-8776 sensitizes human leukemia cells to HDAC inhibitors by targeting the intra-S checkpoint and DNA replication and repair. Mol Cancer Ther. 12(6):878-889 (2013).
Datta et al. Kinetic properties and inhibition of human T lymphoblast deoxycytidine kinase. J Biol Chem 264(16):9359-9364 (1989).
Davies et al. Chk1 inhibition and Wee1 inhibition combine synergistically to impede cellular proliferation. Cancer Biol Ther. 12(9):788-796 (2011).
Davies et al. Single-agent inhibition of Chk1 is antiproliferative in human cancer cell lines in vitro and inhibits tumor xenograft growth in vivo. Oncol Res. 19(7):349-363 (2011).
De Bono et al. Translating cancer research into targeted therapeutics. Nature 467:543-9 (2010).
De Murcia et al. Requirement of poly(ADP-ribose) polymerase in recovery from DNA damage in mice and in cells. PNAS USA 94:7303-7307 (1997).
Del Nagro et al. Chk1 inhibition in p53-deficient cell lines drives rapid chromosome fragmentation followed by caspase-independent cell death. Cell Cycle. 13(2):303-314 (2014).
Ding et al. MLH1 expression sensitivities ovarian cancer cells to cell death mediated by XIAP inhibition. Br J Cancer 101:269-277 (2009).
Dobrovolsky et al. Effect of arylformamidase (kynurenine formamidase) gene inactivation in mice on enzymatic activity, kynurenine pathway metabolites and phenotype. Biochimica et biophysica acta 1724:163-172 (2005a).
Dobrovolsky et al. Mice deficient for cytosolic thymidine kinase gene develop fatal kidney disease. Molecular genetics and metabolism 78:1-10 (2003).
Dobrovolsky et al. Micronucleated erythrocyte frequency in control and azidothymidine-treated Tk+/+, Tk+/- and Tk-/- mice. Mutation research 570:227-235 (2005b).
Emsley et al. Features and development of Coot. Acta Crystallogr D Biol Crystallogr. 66(Pt 4):486-501 (2010).
Engelke et al. Sensitization of pancreatic cancer to chemoradiation by the Chk1 inhibitor MK8776. Clin Cancer Res. 2013;19(16):4412-4421.
Eriksson et al. Allosteric regulation of calf thymus ribonucleotide reductase. Ciba Found Symp 68:165-175 (1978).
Eriksson et al. Structure and function of cellular deoxyribonucleoside kinases. Cell Mol Life Sci 59:1327-1346 (2002).
Eyles et al. Oral delivery and fate of poly(lactic acid) microsphere-encapsulated interferon in rats. J Pharm Pharmacol. 49(7):669-74 (1997).
Fan et al. Bioluminescent assays for high-throughput screening. Assay Drug Dev Technol. 5(1):127-136(2007).
Finch et al. Triapine (3-aminopyridine-2-carboxaldehyde thiosemicarbazone; 3-AP): an inhibitor of ribonucleotide reductase with antineoplastic activity. Adv Enzyme Regul. 39:3-12 (1999).
Fingl et al. Chapter 1: General Principles. The Pharmacological Basis of Therapeutics (49 pgs) (1975).
Fleisher, David et al., Improved Oral drug delivery: solubility limitations overcome by the use of prodrugs. Advanced Drug Delivery Reviews 19(2):115-130 (May 22, 1996).
Fokas et al. Targeting ATR in DNA damage response and cancer therapeutics. Cancer Treat Rev. 40(1):109-117 (2014).
Fokas et al. Targeting ATR in vivo using the novel inhibitor VE-822 results in selective sensitization of pancreatic tumors to radiation. Cell Death Dis. 3:0441 (2012).
Fong et al. Inhibition of poly(ADP-ribose) polymerase in tumors from BRCA mutation carriers. N Engl J Med 361(2):123-134 (2009).
Fong et al. Poly(ADP)-ribose polymerase inhibition: frequent durable responses in BRCA carrier ovarian cancer correlating with platinum-free interval. J Clin Oncol 28:2512-2519 (2010).
Foote et al. Discovery of 4- {4-[(3R)-3-Methylmorpholin-4-yl]-6-[1-(methylsulfonyl)cyclopropyl]pyrimidin-2-yll -1H-indole (AZ20): a potent and selective inhibitor of ATR protein kinase with monotherapy in vivo antitumor activity. J Med Chem. 56(5):2125-2138 (2013).
Fyrberg et al. Cell cycle effect on the activity of deoxynucleoside analogue metabolising enzymes. Biochem Biophy Res Comm 357:847-853 (2007).
Gagou et al. Enhanced H2AX phosphorylation, DNA replication fork arrest, and cell death in the absence of Chk1. Mol Biol Cell 21:739-752 (2010).
Gambhir. Molecular Imaging of Cancer with Positron Emission Tomography. Nat. Rev. Cancer 2:683-693 (2002).
Gao et al.: Controlled release of a contraceptive steroid from biodegradable and injectable gel formulations: in vitro evaluation. Pharm Res. 12(6):857-863 (1995).
Gazzard et al. Discovery of the 1,7-diazacarbazole class of inhibitors of checkpoint kinase 1. Bioorg Med Chem Lett. 24(24):5704-5709 (2014).
Gehring et al. Thymidine secretion by cultured chicken embryo fibroblasts and NIH/3T3 cells: quantification and time course. Biochemical and biophysical research communications 177:259-264 (1991).
Gelmon et al. Olaparib in patients with recurrent high-grade serous or poorly differentiated ovarian carcinoma or triple-negative breast cancer: a phase 2, multicentre, open-label, nonrandomised study. Lancet Oncol 12:852-861 (2011).
Gentry. Viral thymidine kinases and their relatives. Pharmacol Ther 54:319-355 (1992).
Giles et al. Phase T and pharmacodynamic study of Triapine, a novel ribonucleotide reductase inhibitor, in patients with advanced leukemia. Leuk Res. 27(12):1077-1083 (2003).
Godsey et al. Structural basis for the preference of UTP over ATP in human deoxycytidine kinase: illuminating the role of main-chain reorganization. Biochemistry 45:452-61 (2006).
Golub et al., Molecular classification of cancer: class discovery and class prediction by gene expression monitoring. Science. 286(5439):531-537 (1999).
Graeser et al. A marker of homologous recombination predicts pathologic complete response to neoadjuvant chemotherapy in primary breast cancer. Clin Cancer Res 16:6159-6168 (2010).
Gudipati et al. Solution-phase parallel synthesis with oligoethylene glycol sorting tags. Preparation of all four stereoisomers of the hydroxybutenolide fragment of murisolin and related acetogenins. J Org Chem 71:3599-607 (2006).
Guerra et al. Chronic pancreatitis is essential for induction of pancreatic ductal adenocarcinoma by K-Ras oncogenes in adult mice. Cancer Cell 11:291-302 (2007).
Guertin et al. Preclinical evaluation of the WEE1 inhibitor MK-1775 as single-agent anticancer therapy. Mol Cancer Ther. 12(8):1442-1452 (2013).
Guertin et al. Unique functions of CHK1 and WEE1 underlie synergistic anti-tumor activity upon pharmacologic inhibition. Cancer Cell Int. 12(1):45 (2012).
Gura, et al. Autism spectrum disorder screening in primary care. J Dev Behav Pediatr. 32(1):48-51 (2011).
Guzi et al. Targeting the replication checkpoint using SCH 900776, a potent and functionally selective CHK1 inhibitor identified via high content screening. Mol Cancer Ther. 10(4):591-602 (2011).
Hale et al. Hypoxia in the thymus: role of oxygen tension in thymocyte survival. Am J Physiol Heart Circ Physiol 28(4):H1467-77 (2002).
Hanahan et al. Hallmarks of cancer: the next generation. Cell 144:646-674 (2011).
Hargreaves. The Role of Molecular Imaging in Drug Discovery and Development. Clin. Pharmacol. Ther. 83:349-353 (2008).
Hastak et al. DNA synthesis from unbalanced nucleotide pools causes limited DNA damage that triggers ATR-CHK1-dependent p53 activation. PNAS USA 105:6314-9 (2008).
Haveman et al. Time course of enhanced activity of deoxycytidine kinase and thymidine kinase 1 and 2 in cultured human squamous lung carcinoma cells, SW-1573, induced by gamma-irradiation. Oncol Rep 16:901-905 (2006).
Heitz et al. Poly(ADP-ribosyl)ation polymerases: mechanism and new target of anticancer therapy. Expert Rev Anticancer Ther 10:1125-1136 (2010).

(56) References Cited

OTHER PUBLICATIONS

Helin. Regulation of cell proliferation by the E2F transcription factors. Curr Opin Genet Dev 8:28-35 (1998).
Hengstschlager et al. Cell cycle regulation of deoxycytidine kinase. Evidence for post-transcriptional control. FEBS letters 321:237-240 (1993).
Hirai et al. MK-1775, a small molecule Wee1 inhibitor, enhances anti-tumor efficacy of various DNA-damaging agents, including 5-fluorouracil. Cancer Biol Ther. 9(7):514-522 (2010).
Hirai et al. Small—molecule inhibition of Wee1 kinase by MK-1775 selectively sensitizes p53-deficient tumor cells to DNA-damaging agents. Mol Cancer Ther. 8(11):2992-3000 (2009).
Huntoon et al. ATR inhibition broadly sensitizes ovarian cancer cells to chemotherapy independent of BRCA status. Cancer Res. 73(12):3683-3691 (2013).
Hynes et al. Evaluation of the likelihood of a selective CHK1 inhibitor (LY2603618) to inhibit CYP2D6 with desipramine as a probe substrate in cancer patients. Biopharm Drug Dis-pos. 36:49-63 (2014).
Jackson et al. An indolocarbazole inhibitor of human checkpoint kinase (Chk1) abrogates cell cycle arrest caused by DNA damage. Cancer Res. 60(3):566-572 (2000).
Jadvar et al. 18F-FDG Uptake in Lung, Breast, and Colon Cancers: Molecular Biology Correlates and Disease Characterization. J. Nucl. Med. 50:1820-1827 (2009).
Jain et al. Metabolite profiling identifies a key role for glycine in rapid cancer cell proliferation. Science. 336:1040-4 (2012).
Jessop et al. Lead optimization and structure-based design of potent and bioavailable deoxycytidine kinase inhibitors. Bioorg Med Chem Lett 19(23):6784-6787 (2009).
Johnson et al. Compromised CDK1 activity sensitizes BRCA-proficient cancers to PARP inhibition. Nat Med 17:875-882 (2011).
Johnson et al. Pre-clinical evaluation of cyclin-dependent kinase 2 and 1 inhibition in anti-estrogen-sensitive and resistant breast cancer cells. Br J Cancer 102:342-350 (2010).
Johnson et al., Relationships between drug activity in NCI preclinical in vitro and in vivo models and early clinical trials. British Journal of Cancer 84(10):1424-1431 (2001).
Jordheim et al. Characterization of a gemcitabine-resistant murine leukemic cell line: reversion of in vitro resistance by a mononucleotide prodrug. Clin Cancer res 10(16):5614-5621 (2004).
Jorgensen et al. Comparison of Simple Potential Functions for Simulating Liquid Water. Journal of Chemical Physics 79:926-935 (1983).
Jorgensen et al. Development and testing of the OPLS all-atom force field on conformational energetics and properties of organic liquids. Journal of the American Chemical Society 118:11225-11236 (1996).
Jorgensen et al. Free energies of hydration from a generalized Born model and an ALL-atom force field. Journal of Physical Chemistry B 108:16264-16270 (2004).
Jorgensen et al. Molecular modeling of organic and biomolecular systems using BOSS and MCPRO. Journal of Computational Chemistry 26:1689-1700 (2005).
Jorgensen et al. Perspective on Free-Energy Perturbation Calculations for Chemical Equilibria. J. Chem. Theory Comput 4:869-876 (2008).
Joseph et al. Synthesis of Benzyl Bromides with Hexabromoacetone: an Alternative Path to Drug Intermediates. Tetrahedron Lett. 52:13-16 (2011).
Josse et al. ATR Inhibitors VE-821 and VX-970 Sensitize Cancer Cells to Topoisomerase I Inhibitors by Disabling DNA Replication Initiation and Fork Elongation Responses. Cancer Res. 74(23):6968-6979 (2014).
Kabsch. XDS. Acta Crystallogr D Biol Crystallogr 66:125-32 (2010).
Kamphorst et al. Liquid chromatography-high resolution mass spectrometry analysis of fatty acid metabolism. Anal Chem. 83:9114-22 (2011).
Karp et al. Phase I and pharmacologic trial of cytosine arabinoside with the selective checkpoint 1 inhibitor Sch 900776 in refractory acute leukemias. Clin Cancer Res. 18(24):6723-6731 (2012).
Kawabe. G2 checkpoint abrogators as anticancer drugs. Mol Cancer Ther. 3(4):513-519 (2004).
Ke et al. Control of dTTp pool size by anaphase promoting complex/cyclosome is essential for the maintenance of genetic stability. Genes Dev 19:1920-1933 (2005).
King et al. Characterization and preclinical development of LY2603618: a selective and potent Chk1 inhibitor. Invest New Drugs. 32(2):213-226 (2014).
Koc et al. Hydroxyurea arrests DNA replication by a mechanism that preserves basal dNTP pools. J Biol Chem. 279(1):223-230 (2004).
Kolesar et al. Population pharmacokinetics of 3-aminopyridine-2-carboxaldehyde thiosemicarbazone (Triapine(R)) in cancer patients. Cancer Chemother Pharmacol. 67(2):393-400 (2011).
Krishnan et al. Novel Role of 3-Phosphoglycerate Kinase, a Glycolytic Enzyme, in the Activation of L-Nucleoside Analogs, a new class of Anticancer and Antiviral Agents. J. Biol. Chem. 278:36726-36732 (2003).
Kufe et al. Effect of high-dose thymidine infusions in patients with mycosis fungoides. Cancer. 48:1513-6 (1981).
Kufe et al. High-dose thymidine infusions in patients with leukemia and lymphoma. Blood. 55:580-9 (1980).
Kumar et al. Highly mutagenic and severely imbalanced dNTP pools can escape detection by the S-phase checkpoint. Nucleic Acids Res 38:3975-3983 (2010).
Kumar et al. Mechanisms of mutagenesis in vivo due to imbalanced dNTP pools. Nucleic Acids Res 39:1360-1371 (2011).
Lainchbury et al. Discovery of 3-alkoxyamino-5-(pyridin-2-ylamino)pyrazine-2-carbonitriles as selective, orally bioavailable CHK1 inhibitors. J Med Chem. 55(22):10229-10240 (2012).
Laing et al. Noninvasive prediction of tumor responses to gemcitabine using positron emission tomography. PNAS USA 106(8):2847-2852 (2009).
Lala et al. Role of nitric oxide in tumor progression: Lessons from experimental tumors. Cancer and Metastasis Reviews 17(1):91-106 (1998).
Laxer et al. (15N5)-Labeled Adenine Derivatives: Synthesis and Studies of Tautomerism by 15N NMR Spectroscopy and Theoretical Calculations. J. Org. Chem., 66:5463-5481 (2001).
Lee et al. Role of checkpoint kinase 1 (Chk1) in the mechanisms of resistance to histone deacetylase inhibitors. PNAS USA 108(49):19629-19634 (2011).
Li et al. Defective gene expression, S phase progression, and maturation during hematopoiesis in E2F1/E2F2 mutant mice. Molecular and cellular biology 23:3607-3622 (2003).
Liu et al. Characterization of Torin2, an ATP-competitive inhibitor of mTOR, ATM, and ATR. Cancer Res. 73(8):2574-2586 (2013).
Luo et al. Principles of cancer therapy: oncogene and non-oncogene addiction. Cell 36:823-837 (2009).
Lv et al. Computational studies on the binding mechanism between triazolone inhibitors and Chk1 by molecular docking and molecular dynamics. Mol Biosyst. 11(1):275-286 (2015).
Ma et al. A multicenter phase II trial of 3-aminopyridine-2-carboxaldehyde thiosemicarbazone (3-AP, Triapine) and gemcitabine in advanced non-small-cell lung cancer with pharmacokinetic evaluation using peripheral bloom mononuclear cells. Invest New Drugs 26:169-173 (2008).
Mackenzie et al. A Phase II study of 3-aminopyridine-2-carboxaldehyde thiosemicarbazone (3-AP) and gemcitabine in advanced pancreatic carcinoma. Atrial of the Princess Margaret hospital Phase II consortium. Invest New Drugs 25:553-558 (2007).
Maddocks, et al. Serine starvation induces stress and p53-dependent metabolic remodelling in cancer cells. Nature. 493(7433):542-6 (2013).
Maillard et al. The requirement for Notch signaling at the beta-selection checkpoint in vivo is absolute and independent of the pre-T cell receptor. J Exper Med 203:2239-2245 (2006).
Mathews et al. Measuring DNA precursor pools in mitochondria. Methods Mol Biol 554:371-381 (2009).

(56) References Cited

OTHER PUBLICATIONS

Matsuoka et al. ATM and ATR substrate analysis reveals extensive protein networks responsive to DNA damage. Science 316(5828):1160-1166 (2007).
Matthews et al. Pharmacological abrogation of S-phase checkpoint enhances the anti-tumor activity of gemcitabine in vivo. Cell Cycle. 6(1): 104-110 (2007).
Matthews et al. Structure-based design, discovery and development of checkpoint kinase inhibitors as potential anticancer therapies. Expert Opin Drug Discov. 8(6):621-640 (2013).
McNeely et al. CHEK again: revisiting the development of CHK1 inhibitors for cancer therapy. Pharmacol Ther. 142(1):1-10 (2014).
Metropolis et al. The Monte Carlo Method. J. Am. Statistical Assn. 44:335-341 (1949).
Montano et al. Preclinical development of the novel Chk1 inhibitor SCH900776 in combination with DNA-damaging agents and antimetabolites. Mol Cancer Ther. 11(2):427-438 (2012).
Montano et al. Sensitization of human cancer cells to gemcitabine by the Chk1 inhibitor MK-8776: cell cycle per-turbation and impact of administration schedule in vitro and in vivo. BMC Cancer. 13:604 (2013).
Morgan et al. Mechanism of radiosensitization by the Chk1/2 inhibitor AZD7762 involves abrogation of the G2 checkpoint and inhibition of homologous recombinational DNA repair. Cancer Res. 70(12):4972-4981 (2010).
Mukherjee et al. The dual PI3K/mTOR inhibitor NVP-BEZ235 is a potent inhibitor of ATM-and DNA-PKCs-mediated DNA damage responses. Neoplasia. 14(1):34-43 (2012).
Muller et al. Fluorine in Pharmaceuticals: Looking Beyond Intuition. Science 317:1881-1886 (2007).
Murphy et al. Development of new deoxycytidine kinase inhibitors and noninvasive in vivo evaluation using positron emission tomography. J Med Chem 56(17):6696-6708 (2013).
Murshudov et al. REFMAC5 for the refinement of macromolecular crystal structures. Acta Crystallogr D. Biol Crystallog. 67(Pt 4):355-367 (2011).
Nair-Gill et al. PET probes for distinct metabolic pathways have different cell specificities during immune responses in mice. J Clin Invest. 120(6):2005-15 (2010).
Nassar et al. Improving the decision-making process in structural modification of drug candidates: reducing toxicity. Drug Discov Today 9:1055-1064 (2004).
Nathanson et al. Co-targeting of convergent nucleotide biosynthetic pathways for leukemia eradication. J Exp Med 211(3):473-486 (2014).
Nomme et al. Structural characterization of new deoxycytidine kinase inhibitors rationalizes the affinity-determining moieties of the molecules. Acta Crystallogr D Biol Crystallogr. 70:68-78 (2014).
Nomme et al. Structure-guided development of deoxycytidine kinase inhibitors with nanomolar affinity and improved metabolic stability. J Med Chem 57(22):9480-9494 (2014).
Nyhan. Disorders of purine and pyrimidine metabolism. Molecular genetics and metabolism 86:25-33 (2005).
O'Dwyer et al. Role of thymidine in biochemical modulation: a review. Cancer Res. 47:3911-9 (1987).
Okonya et al. Synthesis of 2-Oxazolone-4-Carboxylates from 3-Nosyloxy- and 3-Bromo-2-ketoesters. J. Org. Chem. 67:1102-1108 (2002).
Oliver et al. dNTP pools imbalance as a signal to initiate apoptosis. Experientia 52:995-1000 (1996).
Ooi et al. Increased deoxycytidine kinase activity by etoposide in L1210 murine leukemic cells. Biol Pharm Bull 19(10):1382-1383 (1996).
Oriuchi et al. Present Role and Future Prospects of Positron Emission Tomography in Clinical Oncology. Cancer Sci. 97:1291-1297 (2006).
Ostro et al. Use of Liposomes as Injectable-Drug Delivery Systems. Am J Hosp Pharm 46(8):1576-1587 (Aug. 1989).
Overwijk et al. gp100/pmel 17 is a inurine tumor rejection antigen: induction of seIP'-reactive, tumoricidal T cells using high-affinity, altered peptide ligand. J Exp Med 188:277-286 (1998).
Palmer et al. 4-Phenylpyrrolo[3,4-c]carbazole-1,3(2H,6H)-dione inhibitors of the checkpoint kinase Wee1. Structure-activity relationships for chromophore modification and phenyl ring substitution. J Med Chem. 49(16):4896-4911 (2006).
Papinazath et al. Effects of purine nucleoside phosphorylase deficiency on thymocyte development. J Allergy Clin Immunol 128(4):854-863 (2011).
Park et al. Metabolism of Fluorine-containing Drugs. Annu. Rev. Pharmacol. Toxicol. 41:443-470 (2001).
Parmar et al. Distribution of hematopoietic stem cells in the bone marrow according to regional hypoxia. Proceedings of the National Academy of Sciences of the United States of America 104:5431-5436 (2007).
Parsels et al. Gemcitabine sensitization by checkpoint kinase 1 inhibition correlates with inhibition of a Rad51 DNA damage response in pancreatic cancer cells. Mol Cancer Ther. 8(1):45-54 (2009).
Pasti et al. Reaction of Human UMP-CMP Kinase with Natural and Analog Substrates. Eur. J. Biochem. 270:1784-1790 (2003).
PCT/US2012/028259 International Search Report and Written Opinion dated May 24, 2012.
PCT/US2014/050931 International Search Report and Written Opinion dated Nov. 14, 2014.
PCT/US2016/017172 International Search Report and Written Opinion dated Aug. 5, 2016.
PCT/US2016/017199 International Search Report and Written Opinion dated Sep. 7, 2016.
PCT/US2017/012718 International Search Report and Written Opinion dated May 10, 2017.
Pearce et al. Chapter 18: Failure modes in anticancer drug discovery and development, Cancer Drug Design and Discovery Edited by Stephen Neidle pp. 424-435 (2008).
Penit et al. Regulation of thymocyte proliferation and survival by deoxynucleosides. Deoxycytidine produced by thymic accessory cells protects thymocytes from deoxyguanosine toxicity and stimulates their spontaneous proliferation. EP J Immunol 16:257-263 (1986).
Peralta-Leal et al. PARP inhibitors: new partners in the therapy of cancer and inflammatory diseases. Free Radic Biol Med 47:13-26 (2009).
Petersen et al. p53-dependent G(1) arrest in 1st or 2nd cell cycle may protect human cancer cells from cell death after treatment with ionizing radiation and Chk1 inhibitors. Cell Prolif. 43(4):365-371 (2010).
Pines et al. Targeting radiation-resistant hypoxic tumour cells through ATR inhibition. Br J Cancer. 107(2):291-299 (2012).
Prevo et al. The novel ATR inhibitor VE-821 increases sensitivity of pancreatic cancer cells to radiation and chemotherapy. Cancer Biol Ther. 13(11):1072-1081 (2012).
Probst et al. Oxygen dependent regulation of mammalian ribonucleotide reductase in vivo and possible significance for replicon initiation. Biochemical and biophysical research communications 163:334-340 (1989).
PubChem CID-60202410, located at https://pubchem.ncbi.nlm.nih.gov/compound/60202410, create date Oct. 15, 2012, last accessed Apr. 20, 2017.
PubChem CID-60202449, located at https://pubchem.ncbi.nlm.nih.gov/compound/60202449, create date Oct. 15, 2012, last accessed Apr. 20, 2017s.
Radu et al. Molecular imaging of lymphoid organs and immune activation by positron emission tomography with a new [18F]-labeled 2'-deoxycytidine analog. Nat Med 14(7):783-788 (2008).
Rao. Recent developments of collagen-based materials for medical applications and drug delivery systems. J Biomater Sci Polym Ed. 7(7):623-45 (1995).
Rawlinson et al. gammaH2AX and Chk1 phosphorylation as predictive pharmacodynamic biomarkers of Chk1 inhibitor-chemotherapy combination treatments. BMC Cancer. 14:483 (2014).

(56) References Cited

OTHER PUBLICATIONS

Reader et al. Structure-guided evolution of potent and selective CHK1 inhibitors through scaffold morphing. J Med Chem. 54(24):8328-8342 (2011).
Reaper et al. Selective killing of ATM- or p53-deficient cancer cells through inhibition of ATR. Nat Chem Biol. 7(7):428-430 (2011).
Reichard et al. Utilization of desoxyribosides in the synthesis of polynucleotides. The Journal of biological chemistry 188:839-846 (1951).
Reichard. Interactions between deoxyribonucleotide and DNA synthesis. Annu. Rev. Biochem. 57:349-374 (1988).
Reichard. Ribonucleotide reductases: the evolution of allosteric regulation. Arch Biochem Biophys 397:149-155 (2002).
Reinhardt et al. Exploiting synthetic lethal interactions for targeted cancer therapy. Cell Cycle 8:3112-3119 (2009).
Repasky et al. Improved semiempirical heats of formation through the use of bond and group equivalents. J Comput Chem 23:498-510 (2002).
Repasky et al. PDDG/PM3 and PDDG/MNDO: improved semiempirical methods. J Comput Chem 23:1601-22 (2002).
Riesterer et al. A novel Chk inhibitor, XL-844, increases human cancer cell radiosensitivity through promotion of mitotic catastrophe. Invest New Drugs. 29(3):514-522 (2011).
Rigo et al. Oncological Application of Positron Emission Tomography with Fluorine-18. Eur. J. Nucl. Med. 23:1641-1674 (1996).
Rodriguez et al. Thymidine selectively enhances growth suppressive effects of camptothecin/irinotecan in MSI+ cells and tumors containing a mutation of MRE11. Clin Cancer Res 14:5476-5483 (2008).
Russell et al. Combination therapy targeting the Chk1 and Wee1 kinases shows therapeutic efficacy in neuroblastoma. Cancer Res. 73(2):776-784 (2013).
Ruzankina et al. Deletion of the developmentally essential gene ATR in adult mice leads to age-related phenotypes and stem cell loss. Cell stem cell 1:113-126 (2007).
Sabini et al. Non-enantioselectivity property of human deoxycytidine kinase explained by structures of the enzyme in complex with L- and D-nucleosides. J Med Chem 50(13):3004-3014 (2007).
Sabini et al. Structural basis for substrate promiscuity of dCK. J Mol Biol 378:607-21 (2008).
Sabini et al. Structure of human dCK suggests strategies to improve anticancer and antiviral therapy. Nat Struct Biol 10:513-9 (2003).
Salovska et al. Radiosensitization of human leukemic HL-60 cells by ATR kinase inhibitor (VE-821): phosphoproteomic analysis. Int J Mol Sci. 15(7):12007-12026 (2014).
Sarmento et al. CHK1 overexpression in T-cell acute lymphoblastic leukemia is essential for proliferation and survival by preventing excessive replication stress. Oncogene 34:2978-2990 (2014).
Sausville et al. Phase I dose-escalation study of AZD7762, a checkpoint kinase inhibitor, in combination with gemcitabine in US patients with advanced solid tumors. Cancer Chemother Pharmacol. 73(3):539-549 (2014).
Schenk et al. Effects of selective check-point kinase 1 inhibition on cytarabine cytotoxicity in acute myelogenous leukemia cells in vitro. Clin Cancer Res. 18(19):5364-5373 (2012).
Schoppy et al. Oncogenic stress sensitizes murine cancers to hypomorphic suppression of ATR. J Clin Invest 122(1):241-252 (2012).
Schuttelkopf et al. PRODRG: a tool for high-throughput crystallography of protein-ligand complexes. Acta Crystallogr D Biol Crystallogr 60:1355-63 (2004).
Schwarzenberg et al. Human biodistribution and radiation dosimetry of novel PET probes targeting the deoxyribonucleoside salvage pathway. European journal of nuclear medicine and molecular imaging. 38:711-21 (2011).
Seiler et al. The intra-S-phase checkpoint affects both DNA replication initiation and elongation: single-cell and -DNA fiber analyses. Mol Cell Biol. 27(16):5806-5818 (2007).
Sherley et al. Regulation of human thymidine kinase during the cell cycle. The Journal of biological chemistry 263:8350-8358 (1988).
Sherman et al. Enzymatic assay for deoxyribonucleoside triphosphates using synthetic oligonucleotides as template primers. Anal Biochem 180:222-226 (1989).
Shewach et al. Nucleotide Specificity of Human Deoxycytidine Kinase. Mol. Pharmacol. 42:518-524 (1992).
Shields et al. Imaging proliferation in vivo with [F-18]FLT and positron emission tomography. Nature Med 4:1334-6 (1998).
Shortman et al. Early T lymphocyte progenitors. Annu Rev Immunol 14:29-47 (1996).
Shu et al. Novel PET probes specific for deoxycytidine kinase. J Nucl Med 51 (7):1092-1098 (2010).
Shu et al. Role of biotransformation studies in minimizing metabolism-related liabilities in drug discovery. AAPS J 10:178-92 (2008).
Simone. Oncology: Introduction, ,Cecil Textbook of Medicine, 20th Edition, vol. 1004-1010 (1996).
Smal et al. Identification of in vivo phosphorylation sites on human deoxycytidine kinase. Role of Ser-74 in the control of enzyme activity. J Biol Chem 281:4887-4893 (2006).
Sorensen et al. The cell-cycle checkpoint kinase Chk1 is required for mammalian homologous recombination repair. Nat Cell Biol. 7(2):195-201 (2005).
Sproul et al. Is activation of the intra-S checkpoint in human fibroblasts an important factor in protection against UV-induced mutagenesis? Cell Cycle. 12(22):3555-3563 (2013).
Stadecker. Comparison of pyrimidine and purine nucleoside secretion and nucleoside kinase expression in resident and elicited peritoneal macrophages. J Immunol 126:1724-1727 (1981).
Staub et al. DNA synthesis and nucleoside metabolism in human tonsillar lymphocyte subpopulations. Acta Otolaryngol Suppl 454:118-124 (1988).
Still et al. Semianalytical Treatment of Solvation for Molecular Mechanics and Dynamics. Journal of the American Chemical Society 112:6127-6129 (1990).
Syljuasen et al. Inhibition of Chk1 by CEP-3891 accelerates mitotic nuclear fragmentation in response to ionizing Radiation. Cancer Res. 64(24):9035-9040 (2004).
Syljuasen et al. Inhibition of human Chk1 causes increased initiation of DNA replication, phosphorylation of ATR targets, and DNA breakage. Mol Cell Biol. 25(9):3553-3562 (2005).
Taghon et al. Delayed, asynchronous, and reversible T-lineage specification induced by Notch/Delta signaling. Gene Dev 19:965-978 (2005).
Taghon et al. Developmental and molecular characterization of emerging beta- and gammadelta-selected pre-T cells in the adult mouse thymus. Immunity 24:53-64 (2006).
Tannous, B.A.: Gaussia Luciferase Reporter Assay for Monitoring Biological Processes in Culture and in Vivo. Nat Protoc. 4(4): 582-591 (2009).
Tao et al. Radiosensitization by Chir-124, a selective CHKI inhibitor: effects of p53 and cell cycle checkpoints. Cell Cycle. 8(8):1196-1205 (2009).
Tarver et al. 5-Fluorocytosine derivatives as inhibitors of deoxycytidine kinase. Bioorg Med Chem Lett 19(23):6780-6783 (2009).
Teng et al. Structure-based design and syn-thesis of (5-arylamino-2H-pyrazol-3-yl)-biphenyl-2',4'-diols as novel and potent human CHK1 inhibitors. J Med Chem. 50(22):5253-5256 (2007).
Terry et al. Flow cytometry after bromodeoxyuridine labeling to measure S and G2+M phase durations plus doubling times in vitro and in vivo. Nature protocols 1:859-869 (2006).
Thompson et al. The cancer therapeutic potential of Chk1 inhibitors: how mechanistic studies impact on clinical trial design. Br J Clin Pharmacol. 76(3):358-369 (2013).
Thompson et al. The Mre1 nuclease is critical for the sensitivity of cells to Chk1 inhibition. PLoS One. 7(8):e44021 (2012).
Torrents et al. Ribonucleotide reductases: divergent evolution of an ancient enzyme. Journal of molecular evolution 55:138-152 (2002).
Toy et al. Requirement for deoxycytidine kinase in T and B lymphocyte development. PNAS USA 107(12):5551-5556 (2010).
Tse et al. CHIR-124, a novel potent inhibitor of Chk1, potentiates the cytotoxicity of topoisomerase I poisons in vitro and in vivo. Clin Cancer Res. 13(2 Pt 1):591-602 (2007).
U.S. Appl. No. 61/450,319, filed Mar. 8, 2011 entitled Deoxycytidine Kinase (dCK) Binding Compounds.

(56) References Cited

OTHER PUBLICATIONS

U.S. Appl. No. 14/002,964 Office Action dated Jul. 22, 2015.
U.S. Appl. No. 14/992,396 Office Action dated Jul. 18, 2016.
U.S. Appl. No. 15/421,258 Office Action dated Jun. 21, 2017.
U.S. Appl. No. 16/068,658 Office Action dated Mar. 1, 2019.
Vagin et al. Molecular replacement with MOLREP. Acta Crystallogr D Biol Crystallogr 66:22-5 (2010).
Van Rompay et al. Substrate Specificity and Phosphorylation of Antiviral and Anticancer Nucleoside Analogs by Human Deoxyribonucleoside Kinases and Ribonucleoside Kinases. Pharmacol. Ther. 100:119-139 (2003).
Vander Heiden. Targeting cancer metabolism: a therapeutic window opens. Nat Rev Drug Discov. 10(9):671-684 (2011).
Vanderpool et al. Characterization of the CHK1 allosteric inhibitor binding site. Biochemistry. 48(41):9823-9830 (2009).
Vavrova et al. Inhibition of ATR kinase with the selective inhibitor VE-821 results in radiosensitization of cells of promyelocytic leukaemia (HL-60). Radiat Environ Biophys. 52(4):471-479 (2013).
Wagner et al. Positron Emission Tomography for Use in Microdosing Studies. Curr. Opin. Drug Discov. Devel. 11:104-110 (2008).
Walton et al. CCT244747 is a novel potent and selective CHK1 inhibitor with oral efficacy alone and in combination with genotoxic anticancer drugs. Clin Cancer Res.18(20):5650-5661 (2012).
Walton et al. The preclinical pharmacology and therapeutic activity of the novel CHK1 inhibitor SAR-020106. Mol Cancer Ther. 9(1):89-100 (2010).
Wang et al. PARP is important for genomic stability but dispensable in apoptosis. Genes Dev 11:2347-2358 (1997).
Wang et al. Positron Emission Tomography: Applications in Drug Discovery and Drug Development. Curr. Top. Med. Chem. 5:1053-1075 (2005).
Wang et al. The checkpoint 1 kinase inhibitor LY2603618 induces cell cycle arrest, DNA damage response and autophagy in cancer cells. Apoptosis. 19(9):1389-1398 (2014).
Warburg et al. The Metabolism of Tumors in the Body. The Journal of general physiology. 8:519-30 (1927).
Ward et al. Irreversible enzyme inhibitors. 200. Active-site-directed inhibitors of deoxycytidine kinase, J Med Chem 20(1):88-92 (Jan. 1977).
Weber. Biochemical strategy of cancer cells and the design of chemotherapy: G. H. A. Clowes Memorial Lecture. Cancer Res 43:3466-3492 (1983).
Weber et al. ATM and ATR as therapeutic targets in cancer. Pharmacol Ther 149:124-38 (2015).
Weber et al. Technology Insight: Advances in Molecular Imaging and an Appraisal of PET/CT Scanning. Nat. Clin. Prac. Oncol. 5:160-170 (2008).
Weber. Positron Emission Tomography as an Imaging Biomarker. J. Clin. Oncol. 24:3282-3292 (2006).
Weiss et al. Phase I dose-escalation study to ex-amine the safety and tolerability of LY2603618, a checkpoint 1 kinase inhibitor, administered 1 day after pemetrexed 500 mg/m(2) every 21 days in patients with cancer. Invest New Drugs. 31(1):136-144 (2013).
Wickremsinhe et al. Disposition and metabolism of LY2603618, a Chk-1 inhibitor following intravenous administration in patients with advanced and/or metastatic solid tumors. Xenobiotica. 44(9):827-841 (2014).
Wienkers et al. Predicting in vivo drug interactions from in vitro drug discovery data. Nature reviews 4:825-833 (2005).
Williams et al. Arf gene loss enhances oncogenicity and limits imatinib response in mouse models of Bcr-Abl-induced acute lymphoblastic leukemia. PNAS USA 103(17):6688-6693 (2006).
Wlodkowic et al. Flow cytometry-based apoptosis detection. Method Mol Biol 559:19-32 (2009).
Wood et al. Positron Emission Tomography in Oncology: A Review. Clin. Oncol. 19:237-255 (2007).
Xiao et al. Identification of preferred chemotherapeutics for combining with a CHK1 inhibitor. Mol Cancer Ther. 12(11):2285-2295 (2013).
Xu et al. Functional compartmentation of dCTP pools. Preferential utilization of salvaged deoxycytidine for DNA repair in human lymphoblasts. J Biol Chern 270(2):631-637 (Jan. 13, 1995).
Yang et al. Deoxycytidine kinase regulates the G2/M checkpoint through interaction with cyclin-dependent kinase 1 in response to DNA damage. Nucleic Acids Res 40(19):9621-9632 (2012).
Yu et al. Novel potent inhibitors of deoxycytidine kinase identified and compared by multiple assays. J Biomol Screen. 15(1):72-79 (2010).
Yu et al. Novel Potent Inhibitors of Deoxycytidine Kinase Identified and Compared by Multiple Assays. J Biomol Screening 15(1):72-79 (2010).
Yu et al. UCN-01 inhibits p53 up-regulation and abrogates gamma-radiation-induced G(2)-M checkpoint independently of p53 by targeting both of the checkpoint kinases, Chk2 and Chkl. Cancer Res. 62(20):5743-5748 (2002).
Zabludoff et al. AZD7762, a novel checkpoint kinase inhibitor, drives checkpoint abrogation and potentiates DNA-targeted therapies. Mol Cancer Ther. 7(9):2955-2966 (2008).
Zhang et al. [18F]Fluoroalkyl agents: synthesis, reactivity and application for development of PET ligands in molecular imaging. Curr. Top. Med. Chem. 7:1817-1829 (2007).
Zhao et al. Structural basis for Chkl inhibition by UCN-01. J Biol Chem.277(48):46609-46615 (2002).
Zuniga-Pflucker et al. Regulation of thymocyte development from immature progenitors. Curr Opin Immunol 8:215-224 (1996).
Zwanzig High-Temperature Equation of State by a Perturbation Method. J. Chem. Phys. 22:1420-1426 (1954).

\* cited by examiner

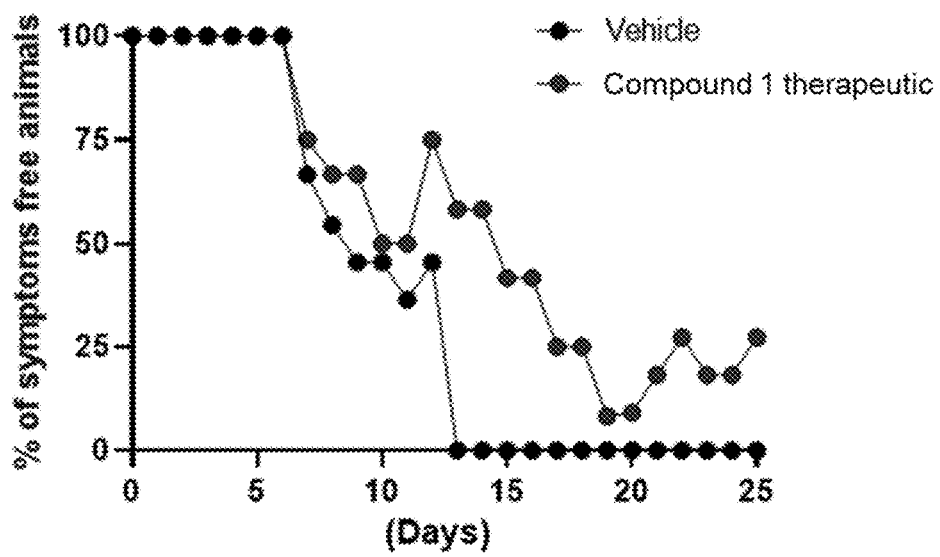
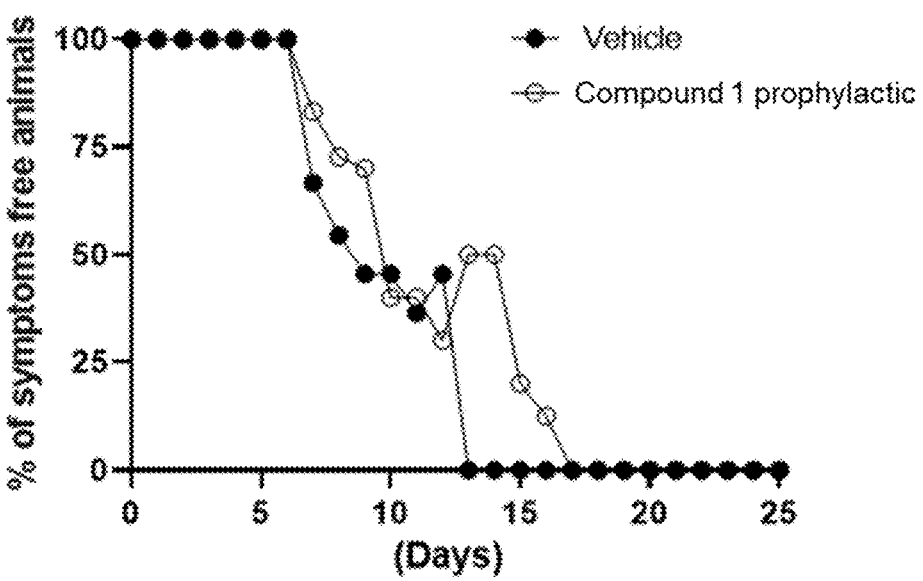
FIG. 14

BC 1
Mouse is emaciated.
- *Skeletal structure extremely prominent; little or no flesh cover.*
- *Vertebrae distinctly segmented.*

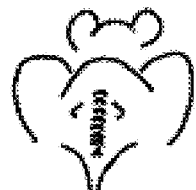
BC 2
Mouse is underconditioned.
- *Segmentation of vertebral column evident.*
- *Dorsal pelvic bones are readily palpable.*

BC 3
Mouse is well-conditioned.
- *Vertebrae and dorsal pelvis not prominent; palpable with slight pressure.*

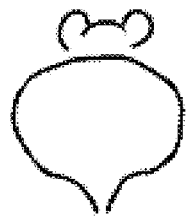
BC 4
Mouse is overconditioned.
- *Spine is a continuous column.*
- *Vertebrae palpable only with firm pressure.*

BC 5
Mouse is obese.
- *Mouse is smooth and bulky.*
- *Bone structure disappears under flesh and subcutaneous fat.*

A "+" or a "-" can be added to the body condition score if additional increments are necessary (i.e. ...2+, 2, 2-...)

FIG. 23

CRYSTALLINE FORMS OF A DEOXYCYTIDINE KINASE INHIBITOR AND USES THEREOF

CROSS-REFERENCE

This application is a continuation of U.S. non-provisional application Ser. No. 17/516,420, filed on Nov. 1, 2021, which claims the benefit of U.S. provisional application nos. 63/108,803 filed Nov. 2, 2020, and 63/190,107 filed May 18, 2021, both of which are incorporated by reference in their entireties.

BACKGROUND OF THE INVENTION

Deoxycytidine kinase (dCK) is an enzyme which plays a crucial role in cellular division and which functions in the phosphorylation of several deoxyribonucleosides and their nucleoside analogs. Deoxycytidine kinase, a rate-limiting enzyme in the salvage pathway of nucleoside synthesis, is observed to be predominantly expressed in hematopoietic tissues and is unregulated in certain solid tumors. dCK deficiency is also associated with certain forms of resistance to antiviral and anticancer chemotherapeutic agents. dCK is a clinically important polypeptide target because of, for example, its role in DNA synthesis and cell division, as well as its association with drug resistance and/or drug sensitivity. Compounds and compositions that bind to and inhibit dCK activities in vivo are desirable for the treatment of diseases and disorders where dCK activity is implicated.

SUMMARY OF THE INVENTION

Provided herein, in one aspect, is a composition comprising a crystalline form of a compound of Formula I:

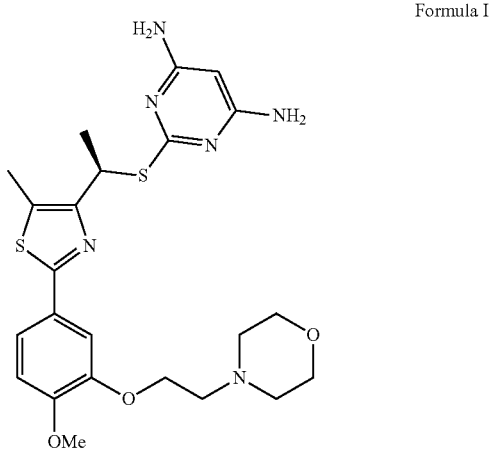 [SMILES: COc1ccc(-c2nc([C@@H](C)Sc3nc(N)cc(N)n3)c(C)s2)cc1OCCN1CCOCC1]

Formula I or a pharmaceutically acceptable salt thereof.

In some embodiments, the crystalline form is a polymorph Form I of a maleate salt of the compound of Formula I.

In some embodiments, the polymorph Form I is characterized by a differential scanning calorimetry (DSC) thermogram comprising an endotherm in the range of about 135 to about 160° C. In some embodiments, the polymorph Form I has a melting point of about 139° C. In some embodiments, the polymorph Form I has a melting point of about 148° C. In some embodiments, the polymorph Form I is characterized by a differential scanning calorimetry (DSC) thermogram substantially as set forth in FIG. 1.

In some embodiments, the polymorph Form I is dry, non-solvated, and/or non-hydrated.

In some embodiments, the polymorph Form I is characterized by an X-ray powder diffraction pattern comprising peaks at 8.2±0.2° 2-θ, 12.7±0.2° 2-θ, and 16.4±0.2° 2-θ, as measured by X-ray powder diffraction using an X-ray wavelength of 1.5406 Å. In some embodiments, the X-ray powder diffraction pattern further comprises at least one peak selected from 16.9±0.2° 2-θ, 17.6±0.2° 2-θ, and 22.9±0.2° 2-θ, as measured by X-ray powder diffraction using an X-ray wavelength of 1.5406 Å. In some embodiments, the X-ray powder diffraction pattern further comprises at least one peak selected from 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least five peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises peaks at 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the polymorph Form I is characterized by an X-ray powder diffraction pattern substantially as set forth in FIG. 2.

In some embodiments, the polymorph Form I is characterized by a thermogravimetric analysis (TGA) thermogram comprising a loss in mass of about 1% to about 5% over a temperature range of about 25 to about 125° C. In some embodiments, the polymorph Form I is characterized by a thermogravimetric analysis (TGA) thermogram comprising a loss in mass of less than about 4% over a temperature range of about 25 to about 125° C. In some embodiments, the polymorph Form I is characterized by a thermogravimetric analysis (TGA) thermogram comprising a loss in mass of less than about 2% over a temperature range of about 25 to about 125° C. In some embodiments, the polymorph Form I is characterized by a thermogravimetric analysis (TGA) thermogram comprising a loss in mass of about 4% over a temperature range of about 25 to about 125° C. In some embodiments, the polymorph Form I is characterized by a thermogravimetric analysis (TGA) thermogram comprising a loss in mass of about 5% to about 15% over a temperature range of about 125 to about 200° C. In some embodiments, the polymorph Form I is characterized by a thermogravimetric analysis (TGA) thermogram comprising a loss in mass of about 10.3% over a temperature range of about 125 to about 200° C. In some embodiments, the polymorph Form I is characterized by a thermogravimetric analysis (TGA) thermogram substantially as set forth in FIG. 3.

In some embodiments, the polymorph Form I comprises less than 5% water. In some embodiments, the polymorph Form I comprises about 0.5% water. In some embodiments, the polymorph Form I comprises about 1.5% water. In some embodiments, the polymorph Form I comprises about 2.5% water.

In some embodiments, the crystalline form is a polymorph Form II of a maleate salt of the compound of Formula I.

In some embodiments, the polymorph Form II is characterized by a differential scanning calorimetry (DSC) thermogram comprising an endotherm in the range of about 150 to about 170° C. In some embodiments, the differential scanning calorimetry (DSC) thermogram further comprises an endotherm in the range of about 25 to about 60° C. In some embodiments, the polymorph Form II has a melting point in the range of about 150 to about 155° C. In some embodiments, the polymorph Form II is characterized by a differential scanning calorimetry (DSC) thermogram substantially as set forth in FIG. 4.

In some embodiments, the polymorph Form II comprises small, acicular needle-like particles. In some embodiments, the needles range in size from about 1 µm to about 50 µm.

In some embodiments, the polymorph Form II is solvated or hydrated.

In some embodiments, the polymorph Form II is characterized by an X-ray powder diffraction pattern comprising peaks at 7.6±0.2° 2-θ, 8.7±0.2° 2-θ, and 16.0±0.2° 2-θ, as measured by X-ray powder diffraction using an X-ray wavelength of 1.5406 Å. In some embodiments, the X-ray powder diffraction pattern further comprises at least one peak selected from 12.2±0.2° 2-θ, 17.6±0.2° 2-θ, and 19.5±0.2° 2-θ, as measured by X-ray powder diffraction using an X-ray wavelength of 1.5406 Å. In some embodiments, the X-ray powder diffraction pattern further comprises at least one peak selected from 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least five peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises peaks at 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the polymorph Form II is characterized by an X-ray powder diffraction pattern substantially as set forth in FIG. 5.

In some embodiments, the polymorph Form II is characterized by a thermogravimetric analysis (TGA) thermogram comprising a loss in mass of about 1% to about 5% over a temperature range of about 25 to about 80° C. In some embodiments, the polymorph Form II is characterized by a thermogravimetric analysis (TGA) thermogram comprising a loss in mass of about 2.0% to about 2.5% over a temperature range of about 25 to about 80° C. In some embodiments, the polymorph Form II is characterized by a thermogravimetric analysis (TGA) thermogram comprising a loss in mass of about 1.8% over a temperature range of about 25 to about 80° C. In some embodiments, the polymorph Form II is characterized by a thermogravimetric analysis (TGA) thermogram comprising a loss in mass of about 2.9% over a temperature range of about 25 to about 70° C. In some embodiments, the polymorph Form II is characterized by a thermogravimetric analysis (TGA) thermogram comprising a loss in mass of about 0% to about 1% over a temperature range of about 70 to about 130° C. In some embodiments, the polymorph Form II is characterized by a thermogravimetric analysis (TGA) thermogram comprising a loss in mass of about 0.5% over a temperature range of about 70 to about 130° C. In some embodiments, the polymorph Form II is characterized by a thermogravimetric analysis (TGA) thermogram comprising a loss in mass of about 0.5% over a temperature range of about 80 to about 130° C.

In some embodiments, the polymorph Form II comprises less than 5% water. In some embodiments, the polymorph Form II comprises from about 1.5% to about 2.5% water. In some embodiments, the polymorph Form II comprises about 3.78% water. In some embodiments, the polymorph Form II comprises about 2.65% water. In some embodiments, the polymorph Form II comprises about 0.8% water.

In some embodiments, greater than 90% by weight of the composition is the crystalline form of the compound of Formula I or a pharmaceutically acceptable salt thereof.

In some embodiments, the composition comprises less than about 2% impurities by weight.

Provided herein, in another aspect, is a pharmaceutical composition comprising the composition described herein and a pharmaceutically acceptable excipient.

Provided herein, in another aspect, is a method of treating a disease or disorder in a subject in need thereof, comprising administering to the subject a therapeutically effective amount of the composition described herein or the pharmaceutical composition described herein.

In some embodiments, the disease or disorder is cancer. In some embodiments, the cancer is selected from lung cancer, breast cancer, colorectal cancer, prostate cancer, melanoma, stomach cancer, bladder cancer, endometrial cancer, kidney cancer, leukemia, liver cancer, lymphoma, pancreatic cancer, and thyroid cancer.

In some embodiments, the disease or disorder is an autoimmune disease. In some embodiments, the autoimmune disease is selected from fibromyalgia, lupus, multiple sclerosis, rheumatoid arthritis, psoriasis, ulcerative colitis, and type 1 diabetes.

Provided herein, in another aspect, is a method of preparing a first crystalline form of a maleate salt of a compound of Formula I:

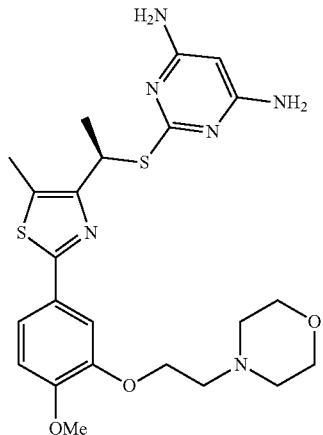

Formula I wherein the method comprises:
(i) dissolving the compound of Formula I and an acid in a first solvent mixture at a first temperature;
(ii) adding a second solvent at a second temperature;
(iii) cooling the resulting solution to a third temperature;
(iv) filtering the solution and drying the resulting solid at a fourth temperature.

In some embodiments, the acid is maleic acid. In some embodiments, the first crystalline form is polymorph Form I. In some embodiments, the first solvent mixture is EtOH/EtOAc and the first temperature is about 50 to about 60° C. In some embodiments, the second solvent is EtOAc and the second temperature is about 20 to about 25° C. In some embodiments, the third temperature is about −5 to about 5° C. In some embodiments, the fourth temperature is about 50 to 55° C.

Provided herein, in another aspect, is a method of preparing a second crystalline form of a maleate salt of a compound of Formula I:

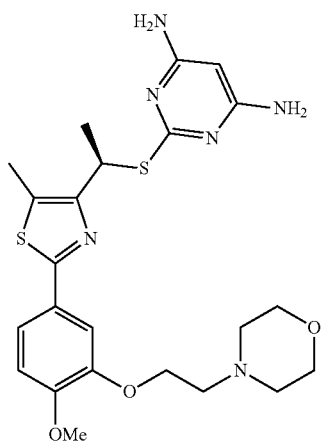

Formula I wherein the method comprises drying a first crystalline form of a maleate salt of the compound of Formula I at a temperature of about 70° C.

In some embodiments, the second crystalline form is polymorph Form II. In some embodiments, the first crystalline form is polymorph Form I.

Provided herein, in another aspect, is a method of preparing a second crystalline form of a maleate salt of a compound of Formula I:

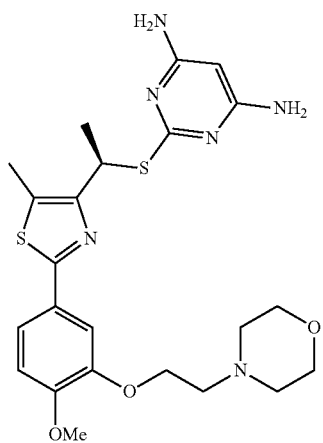

Formula I or a pharmaceutically acceptable salt thereof, wherein the method comprises slurrying a first crystalline form of a maleate salt of the compound of Formula I, or a mixture of crystalline forms of a maleate salt of the compound of Formula I, in water.

In some embodiments, the second crystalline form is polymorph Form II. In some embodiments, the first crystalline form is polymorph Form I.

Provided herein, in another aspect, is a method of treating acute disseminated encephalomyelitis (ADEM) in a subject in need thereof, comprising administering a therapeutically effective amount of a compound of Formula I:

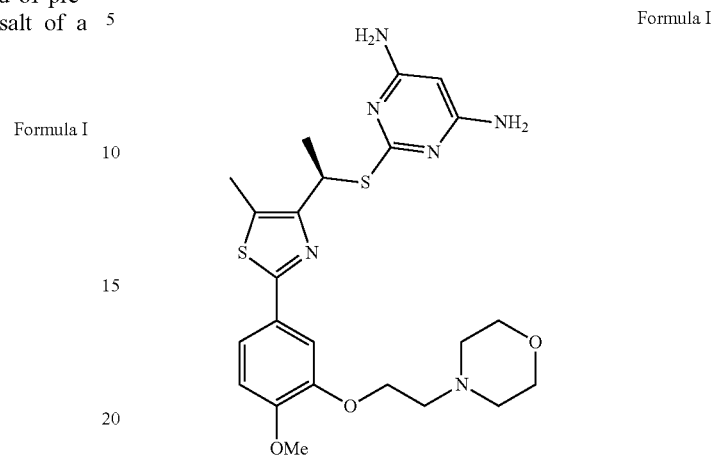

Formula I or a pharmaceutically acceptable salt thereof.

In some embodiments, the compound of Formula I is administered once daily. In some embodiments, the compound of Formula I is administered twice daily. In some embodiments, the administrations of the compound of Formula I are conducted twelve hours apart.

In some embodiments, the compound of Formula I is administered in a unit dosage form. In some embodiments, the unit dosage form comprises from about 0.5 to about 350 mg/kg of the compound of Formula I. In some embodiments, the unit dosage form comprises about 25 mg/kg of the compound of Formula I. In some embodiments, the unit dosage form comprises about 75 mg/kg of the compound of Formula I. In some embodiments, the unit dosage form comprises about 100 mg/kg of the compound of Formula I. In some embodiments, the unit dosage form comprises about 150 mg/kg of the compound of Formula I. In some embodiments, the unit dosage form comprises about 320 mg/kg of the compound of Formula I.

In some embodiments, the total amount of the compound of Formula I administered per day is from about 0.5 to about 350 mg/kg. In some embodiments, the total amount of the compound of Formula I administered per day is about 50 mg/kg. In some embodiments, the total amount of the compound of Formula I administered per day is about 100 mg/kg. In some embodiments, the total amount of the compound of Formula I administered per day is about 150 mg/kg. In some embodiments, the total amount of the compound of Formula I administered per day is about 320 mg/kg. In some embodiments, the total amount of the compound of Formula I administered per day is from about 5 to about 350 mg.

In some embodiments, the compound of Formula I is formulated for oral administration. In some embodiments, the compound of Formula I is formulated as a tablet, a pill, a capsule, a powder, a liquid, a suspension, a solution, a suppository, or an aerosol. In some embodiments, the compound of Formula I is formulated as a solution. In some embodiments, the solution comprises from about 1 to about 50 mg/mL of the compound of Formula I. In some embodiments, the solution comprises about 5 mg/mL of the compound of Formula I. In some embodiments, the solution comprises about 15 mg/mL of the compound of Formula I.

In some embodiments, the solution comprises about 20 mg/mL of the compound of Formula I.

In some embodiments, the administration of the compound of Formula I results in a decrease in interferon gamma (IFNγ) levels in the subject.

Provided herein, in another aspect, is a method of treating an autoimmune disease or disorder in a subject in need thereof, comprising administering a therapeutically effective amount of a compound of Formula I:

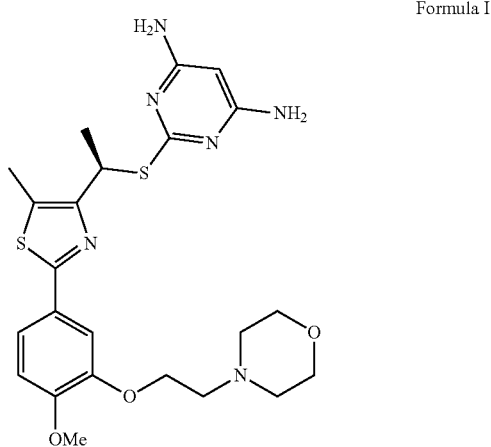 [SMILES: COc1ccc(-c2nc([C@@H](C)Sc3nc(N)cc(N)n3)c(C)s2)cc1OCCN1CCOCC1]

Formula I or a pharmaceutically acceptable salt thereof, wherein the compound of Formula I is administered once daily.

In some embodiments, the disease or disorder is multiple sclerosis. In some embodiments, the disease or disorder is optic neuritis. In some embodiments, the disease or disorder is acute disseminated encephalomyelitis (ADEM).

In some embodiments, the compound of Formula I is administered in a unit dosage form. In some embodiments, the unit dosage form comprises from about 0.5 to about 350 mg/kg of the compound of Formula I. In some embodiments, the unit dosage form comprises about 25 mg/kg of the compound of Formula I. In some embodiments, the unit dosage form comprises about 75 mg/kg of the compound of Formula I. In some embodiments, the unit dosage form comprises about 100 mg/kg of the compound of Formula I. In some embodiments, the unit dosage form comprises about 150 mg/kg of the compound of Formula I. In some embodiments, the unit dosage form comprises about 320 mg/kg of the compound of Formula I.

In some embodiments, the total amount of the compound of Formula I administered per day is from about 0.5 to about 350 mg/kg. In some embodiments, the total amount of the compound of Formula I administered per day is about 50 mg/kg. In some embodiments, the total amount of the compound of Formula I administered per day is about 100 mg/kg. In some embodiments, the total amount of the compound of Formula I administered per day is about 150 mg/kg. In some embodiments, the total amount of the compound of Formula I administered per day is about 320 mg/kg. In some embodiments, the total amount of the compound of Formula I administered per day is from about 5 to about 350 mg.

In some embodiments, the compound of Formula I is formulated for oral administration. In some embodiments, the compound of Formula I is formulated as a tablet, a pill, a capsule, a powder, a liquid, a suspension, a solution, a suppository, or an aerosol. In some embodiments, the compound of Formula I is formulated as a solution. In some embodiments, the solution comprises from about 1 to about 50 mg/mL of the compound of Formula I. In some embodiments, the solution comprises about 5 mg/mL of the compound of Formula I. In some embodiments, the solution comprises about 15 mg/mL of the compound of Formula I. In some embodiments, the solution comprises about 20 mg/mL of the compound of Formula I.

In some embodiments, the administration of the compound of Formula I results in a decrease in interferon gamma (IFNγ) levels in the subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 14 shows the percentage of symptom-free animals observed for the different experimental groups over the course of the mouse model of myelin oligodendrocyte glycoprotein (MOG)-induced experimental autoimmune encephalomyelitis (EAE) experiment.

FIG. 23 shows the body condition scoring scale used in the variable dose mouse model of myelin oligodendrocyte glycoprotein (MOG)-induced experimental autoimmune encephalomyelitis (EAE) experiment.

Figure 1:
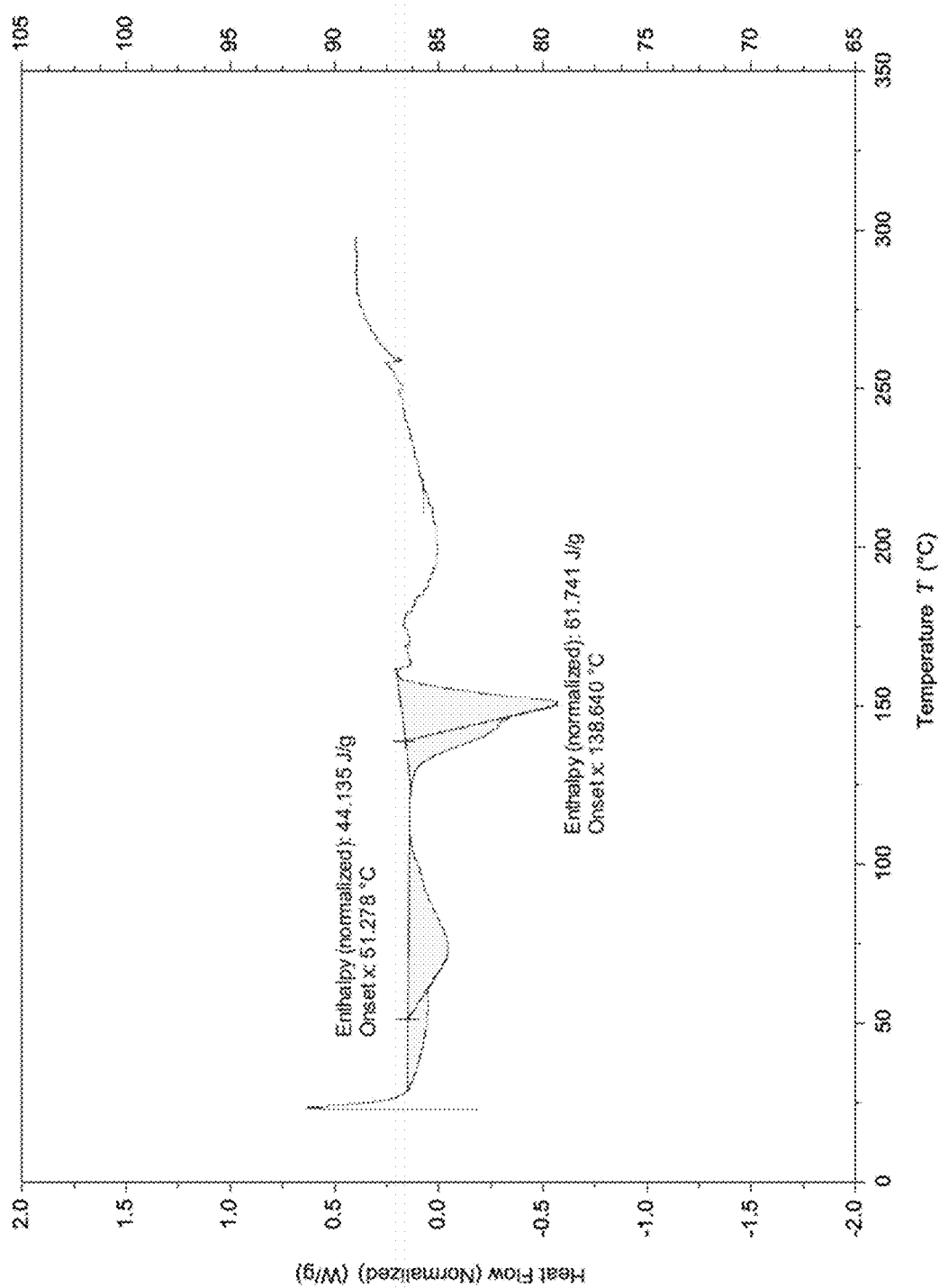
FIG. 1 shows the differential scanning calorimetry (DSC) thermogram for polymorph Form I of the compound of Formula I.

DETAILED DESCRIPTION OF THE INVENTION (R)-2-((1-(2-(4-methoxy-3-(2-morpholinoethoxy)phenyl)-5-methylthiazol-4-yl)ethyl)thio)pyrimidine-4,6-diamine (the compound of Formula I) is a potent and selective deoxycytidine kinase (dCK) inhibitor. dCK inhibitors are useful in the treatment of various diseases, conditions, and disorders for which abnormal dCK activity plays a role, such as cancer and autoimmune diseases.

The preparation and uses of the compound of Formula I have been previously described (see, U.S. Pat. Nos. 9,598,404, 9,981,961, 9,688,673, WO 2016/130581, U.S. Pat. No. 10,570,124, and WO 2016/130562, each of which is incorporated by reference in its entirety).

As used herein, the compound of Formula I or "Compound 1" refers to (R)-2-((1-(2-(4-methoxy-3-(2-morpholinoethoxy)phenyl)-5-methylthiazol-4-yl)ethyl)thio)pyrimidine-4,6-diamine, which has the chemical structure shown below:

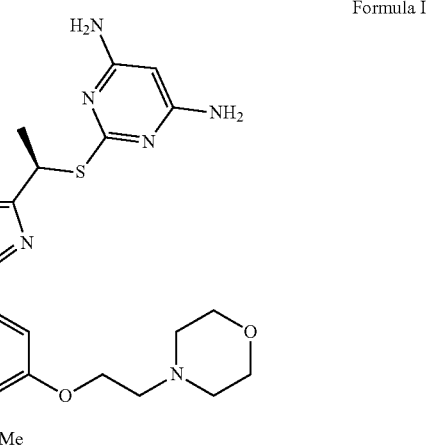

Formula I

In some embodiments, the compound of Formula I is crystalline.

As used herein, "crystalline form," "polymorph," "Form," and "form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compounds of the present disclosure include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. In some embodiments, the crystalline form is a single solid state form, e.g., polymorph Form I.

Definitions

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative, such as those known in the art, for example, described in Remington's Pharmaceutical Sciences 16th edition, Osol, A. Ed. (1980).

As used herein, "treatment" or "treating" is an approach for obtaining beneficial or desired results including and preferably clinical results. For example, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. The protein may be deoxycytidine kinase. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. In some embodiments, the active and/or adjunctive agents are linked or conjugated to one another. In some embodiments, the compounds described herein are combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. In some embodiments, the invention find use in both human medicine and in the veterinary context.

"Disease" or "condition" refer to a state of being or health status of a patient or subject capable of being treated with the compounds or methods provided herein. In some embodiments, the disease as used herein refers to cancer.

"Chemotherapeutic" or "chemotherapeutic agent" is used in accordance with its plain ordinary meaning and refers to a chemical composition or compound having antineoplastic properties or the ability to inhibit the growth or proliferation of cells.

"Cancer model organism", as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

As used herein and in the appended claims, the singular forms "a," "an," and "the" include plural reference unless the context clearly indicates otherwise.

It is understood that aspect and variations of the invention described herein include "consisting" and/or "consisting essentially of" aspects and variations.

Crystalline Forms of the Compound of Formula I

The polymorphs made according to the methods of the invention may be characterized by any methodology according to the art. For example, the polymorphs made according to the methods of the invention may be characterized by X-ray powder diffraction (XRPD), differential scanning calorimetry (DSC), thermogravimetric analysis (TGA), hot-stage microscopy, and/or spectroscopy (e.g., Raman, solid state nuclear magnetic resonance (ssNMR), and infrared (IR)). In some embodiments, crystallinity of a solid form is determined by X-Ray Powder Diffraction (XRPD).

XRPD: Polymorphs according to the invention may be characterized by XRPD. The relative intensities of XRPD peaks can vary, depending upon the particle size, the sample preparation technique, the sample mounting procedure and the particular instrument employed. Moreover, instrument variation and other factors can affect the 2-θ values. Therefore, the XRPD peak assignments can vary, for example by plus or minus about 0.2 degrees.

Figure 4:
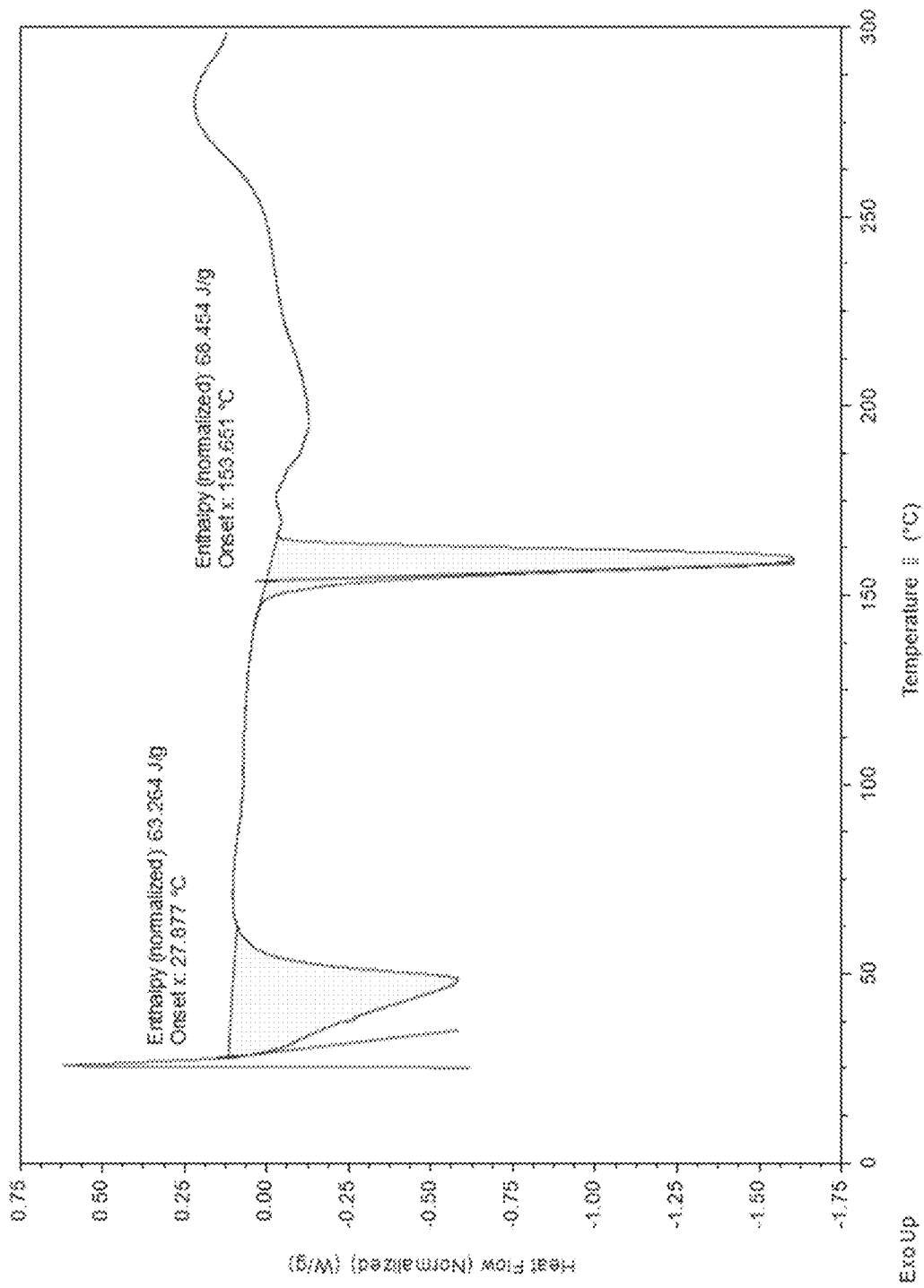
FIG. 4 shows the differential scanning calorimetry (DSC) thermogram for polymorph Form II of the compound of Formula I.

DSC: Polymorphs according to the invention can also be identified by its characteristic DSC thermograms such as shown in FIGS. 1, 4 etc. For DSC, it is known that the temperatures observed will depend upon the rate of temperature change as well as sample preparation technique and the particular instrument employed. Thus, the values reported herein relating to DSC thermograms can vary, for example by plus or minus about 4° C.

TGA: The polymorphic forms of the invention may also give rise to thermal behavior different from that of the amorphous material or another polymorphic form. Thermal behavior may be measured in the laboratory by thermogravimetric analysis (TGA) which may be used to distinguish some polymorphic forms from others. In one aspect, the polymorph may be characterized by thermogravimetric analysis.

The polymorph forms of the compound of Formula I are useful in the production of medicinal preparations and can be obtained by means of a crystallization process to produce crystalline and semi-crystalline forms or a solidification process to obtain the amorphous form. In some embodiments, the crystallization is carried out by either generating the desired compound (for example, the compound of Formula I) in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. In some embodiments, the crystallization comprises addition of a seed form of a desired polymorph. The crystallization or solidification may be followed by drying carried out under controlled conditions until the desired water content is reached in the end polymorphic form.

Polymorph Form I of the Compound of Formula I

FIG. 1 shows the differential scanning calorimetry (DSC) thermogram for polymorph Form I of the compound of Formula I.

Figure 2:
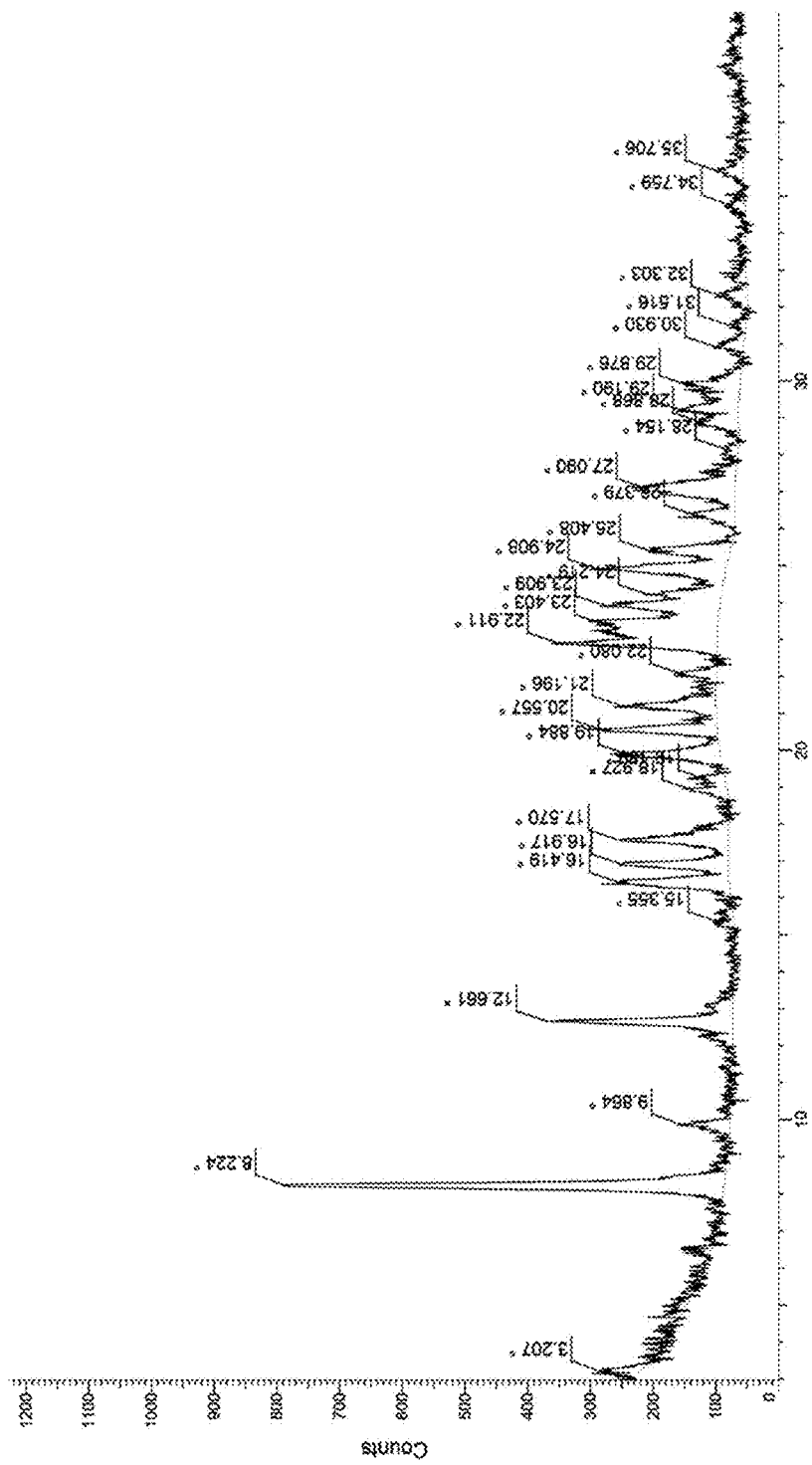
FIG. 2 shows the X-ray powder diffraction (XRPD) pattern for polymorph Form I of the compound of Formula I.

FIG. 2 shows the X-ray powder diffraction (XRPD) pattern for polymorph Form I of the compound of Formula I.

Figure 3:
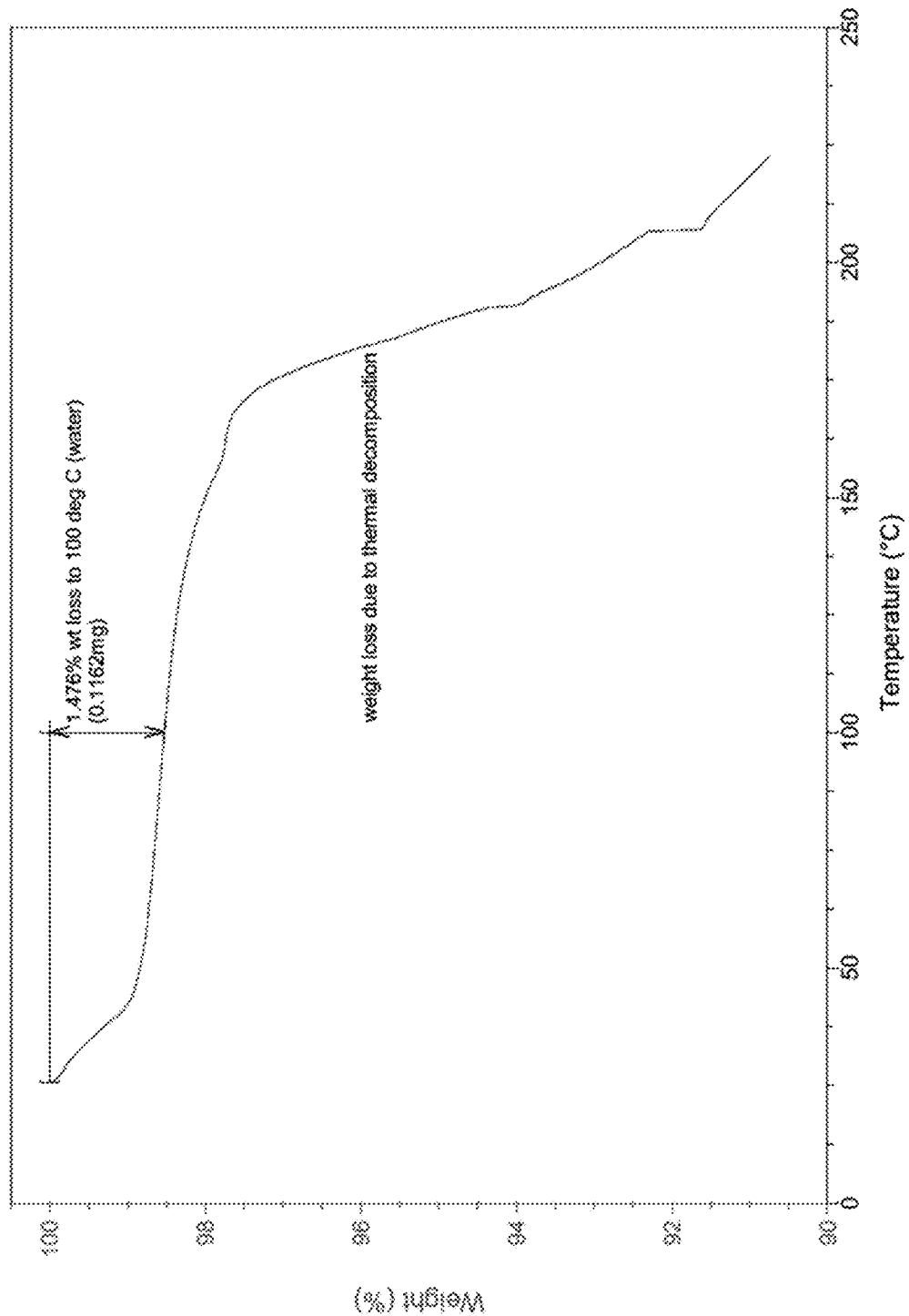
FIG. 3 shows the thermogravimetric analysis (TGA) thermogram for polymorph Form I of the compound of Formula I.

FIG. 3 shows the thermogravimetric analysis (TGA) thermogram for polymorph Form I of the compound of Formula I.

Provided herein, in one aspect, is polymorph Form I of (R)-2-((1-(2-(4-methoxy-3-(2-morpholinoethoxy)phenyl)-5-methylthiazol-4-yl)ethyl)thio)pyrimidine-4,6-diamine. Some embodiments provided a composition comprising polymorph Form I of (R)-2-((1-(2-(4-methoxy-3-(2-morpholinoethoxy)phenyl)-5-methylthiazol-4-yl)ethyl)thio)pyrimidine-4,6-diamine. In some embodiments, polymorph Form I of (R)-2-((1-(2-(4-methoxy-3-(2-morpholinoethoxy)phenyl)-5-methylthiazol-4-yl)ethyl)thio)pyrimidine-4,6-diamine is characterized as having:
  (a) an X-ray powder diffraction pattern comprising peaks at 8.2±0.2° 2-θ, 12.7±0.2° 2-θ, and 16.4±0.2° 2-θ, as measured by X-ray powder diffraction using an X-ray wavelength of 1.5406 Å;
  (b) an X-ray powder diffraction pattern substantially as set forth in FIG. 2;
  (c) a differential scanning calorimetry (DSC) thermogram comprising an endotherm in the range of about 135 to about 160° C.;
  (d) a differential scanning calorimetry (DSC) thermogram substantially as set forth in FIG. 1;
  (e) a thermogravimetric analysis (TGA) thermogram substantially as set forth in FIG. 3; or
  (f) combinations thereof.

In some embodiments, polymorph Form I is characterized by an X-ray powder diffraction pattern substantially as set forth in FIG. 2.

In some embodiments, polymorph Form I is characterized by an X-ray powder diffraction pattern comprising peaks at 8.2±0.2° 2-θ, 12.7±0.2° 2-θ, and 16.4±0.2° 2-θ, as measured by X-ray powder diffraction using an X-ray wavelength of 1.5406 Å. In some embodiments, polymorph Form I is characterized by an X-ray powder diffraction pattern comprising peaks at 8.2±0.1° 2-θ, 12.7±0.1° 2-θ, and 16.4±0.1° 2-θ, as measured by X-ray powder diffraction using an X-ray wavelength of 1.5406 Å. In some embodiments, polymorph Form I is characterized by an X-ray powder diffraction pattern comprising peaks at about 8.2° 2-θ, about 12.7° 2-θ, and about 16.4° 2-θ, as measured by X-ray powder diffraction using an X-ray wavelength of 1.5406 Å.

In some embodiments, the X-ray powder diffraction pattern further comprises at least one peak selected from 16.9±0.2° 2-θ, 17.6±0.2° 2-θ, and 22.9±0.2° 2-θ, as measured by X-ray powder diffraction using an X-ray wavelength of 1.5406 Å. In some embodiments, the X-ray powder diffraction pattern further comprises at least one peak selected from 16.9±0.1° 2-θ, 17.6±0.1° 2-θ, and 22.9±0.1° 2-θ, as measured by X-ray powder diffraction using an X-ray wavelength of 1.5406 Å. In some embodiments, the X-ray powder diffraction pattern further comprises at least one peak selected from about 16.9° 2-θ, about 17.6° 2-θ, and about 22.9° 2-θ, as measured by X-ray powder diffraction using an X-ray wavelength of 1.5406 Å.

In some embodiments, the X-ray powder diffraction pattern further comprises at least one peak selected from 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern further comprises at least one peak selected from 20.6±0.1° 2-θ, 24.9±0.1° 2-θ, and 19.9±0.1° 2-θ, as measured by X-ray powder diffraction using an X-ray wavelength of 1.5406 Å. In some embodiments, the X-ray powder diffraction pattern further comprises at least one peak selected from about 20.6° 2-θ, about 24.9° 2-θ, and about 19.9° 2-θ, as measured by X-ray powder diffraction using an X-ray wavelength of 1.5406 Å.

In some embodiments, the X-ray powder diffraction pattern comprises at least one peak selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least two peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least three peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least four peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least five peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least six peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises at least seven peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2°

2-θ, as measured by X-ray powder diffraction using an X-ray wavelength of 1.5406 Å. In some embodiments, the X-ray powder diffraction pattern comprises at least eight peaks selected from 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises peaks at 8.2±0.2° 2-θ, 12.7±0.2° 2-θ, 16.4±0.2° 2-θ, 16.9±0.2° 2-θ, 17.6±0.2° 2-θ, 22.9±0.2° 2-θ, 20.6±0.2° 2-θ, 24.9±0.2° 2-θ, and 19.9±0.2° 2-θ, as measured by X-ray powder diffraction using an X-ray wavelength of 1.5406 Å. In some embodiments, the X-ray powder diffraction pattern comprises peaks at 8.2±0.1° 2-θ, 12.7±0.1° 2-θ, 16.4±0.1° 2-θ, 16.9±0.1° 2-θ, 17.6±0.1° 2-θ, 22.9±0.1° 2-θ, 20.6±0.1° 2-θ, 24.9±0.1° 2-θ, and 19.9±0.1° 2-θ, as measured by X-ray powder diffraction using an X-ray wavelength of 1.5406 Å. In some embodiments, the X-ray powder diffraction pattern comprises peaks at about 8.2° 2-θ, about 12.7° 2-θ, about 16.4° 2-θ, about 16.9° 2-θ, about 17.6° 2-θ, about 22.9° 2-θ, about 20.6° 2-θ, about 24.9° 2-θ, and about 19.9° 2-θ, as measured by X-ray powder diffraction using an X-ray wavelength of 1.5406 Å.

In some embodiments, polymorph Form I is characterized by a differential scanning calorimetry (DSC) thermogram substantially as set forth in FIG. 1. In some embodiments, polymorph Form I is characterized by a differential scanning calorimetry (DSC) thermogram comprising an endotherm in the range of about 135 to about 160° C.

In some embodiments, polymorph Form I is characterized by a differential scanning calorimetry (DSC) thermogram comprising an endotherm at about 135-160° C., 135-158° C., 135-156° C., 135-154° C., 135-152° C., 135-150° C., 135-148° C., 135-146° C., 135-144° C., 135-142° C., 135-140° C., 140-160° C., 140-158° C., 140-156° C., 140-154° C., 140-152° C., 140-150° C., 140-148° C., 140-146° C., 140-144° C., 140-142° C., 142-160° C., 142-158° C., 142-156° C., 142-154° C., 142-152° C., 142-150° C., 142-148° C., 142-146° C., 142-144° C., 144-160° C., 144-158° C., 144-156° C., 144-154° C., 144-152° C., 144-150° C., 144-148° C., 144-146° C., 146-160° C., 146-158° C., 146-156° C., 146-154° C., 146-152° C., 146-150° C., 146-148° C., 148-160° C., 148-158° C., 148-156° C., 148-154° C., 148-152° C., 148-150° C., 150-160° C., 150-158° C., 150-156° C., 150-154° C., 150-152° C., 152-160° C., 152-158° C., 152-156° C., 152-154° C., 154-160° C., 154-158° C., 154-156° C., 156-160° C., 156-158° C., or 158-160° C. In some embodiments, polymorph Form I is characterized by a differential scanning calorimetry (DSC) thermogram comprising an endotherm at about 135-140° C., for example at about 135° C., 136° C., 137° C., 138° C., 139° C., or 140° C. In some embodiments, the polymorph Form I has a melting point of about 139° C. In some embodiments, polymorph Form I is characterized by a differential scanning calorimetry (DSC) thermogram comprising an endotherm at about 145-150° C., for example at about 145° C., 146° C., 147° C., 148° C., 149° C., or 150° C. In some embodiments, the polymorph Form I has a melting point of about 148° C.

In some embodiments, polymorph Form I is characterized by a thermogravimetric analysis (TGA) thermogram substantially as set forth in FIG. 3. In some embodiments, polymorph Form I decomposes above a temperature of about 50° C., about 100° C., about 150° C., about 200° C., about 250° C., about 300° C., about 350° C., or about 400° C. In some embodiments, polymorph Form I decomposes above a temperature of about 150° C.

In some embodiments, polymorph Form I is stable at room temperature. In some examples, polymorph Form I can be stored at room temperature for an extended period of time without significant chemical degradation or change in the crystalline form. In some examples, polymorph Form I can be stored at room temperature for a time period of at least about 1 day, 2 days, 3 days, or 7 days. In some examples, polymorph Form I can be stored at room temperature for a time period of more than about 7 days. In some examples, polymorph Form I can be stored at room temperature for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, or 6-7 days. In some examples, polymorph Form I can be stored at room temperature for a time period of at least 1 day, 2 days, 3 days, or 7 days.

In some embodiments, polymorph Form I is stable at temperatures above the room temperature and/or at high relative humidity (RH). In some examples, polymorph Form I can be stored at about 40° C. and at about 75% RH for an extended period of time without significant chemical degradation or change in the crystalline form. In some examples, polymorph Form I can be stored at about 40° C. and at about 75% RH for a time period of at least about 1 day, 2 days, 3 days, or 7 days. In some examples, polymorph Form I can be stored at about 40° C. and at about 75% RH for a time period of more than about 7 days. In some examples, polymorph Form I can be stored at about 40° C. and at about 75% RH for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, or 6-7 days. In some examples, polymorph Form I can be stored at about 40° C. and at about 75% RH for a time period of at 1 day, 2 days, 3 days, or 7 days.

In some embodiments, polymorph Form I is stable at temperatures above the room temperature and/or at high relative humidity (RH). In some examples, polymorph Form I can be stored at about 60° C. for an extended period of time without significant chemical degradation or change in the crystalline form. In some examples, polymorph Form I can be stored at about 60° C. for a time period of at least about 1 day, 2 days, 3 days, or 7 days. In some examples, polymorph Form I can be stored at about 60° C. for a time period of more than about 7 days. In some examples, polymorph Form I can be stored at about 60° C. for a time period of 1-2 days, 1-3 days, 1-4 days, 1-5 days, 1-6 days, 1-7 days, 2-3 days, 2-4 days, 2-5 days, 2-6 days, 2-7 days 3-4 days, 3-5 days, 3-6 days, 3-7 days, 4-5 days, 4-6 days, 4-7 days, 5-6 days, 5-7 days, or 6-7 days. In some examples, polymorph Form I can be stored at about 60° C. for a time period of at 1 day, 2 days, 3 days, or 7 days.

Polymorph Form II of the Compound of Formula I

FIG. 4 shows the differential scanning calorimetry (DSC) thermogram for polymorph Form II of the compound of Formula I.

Figure 5:
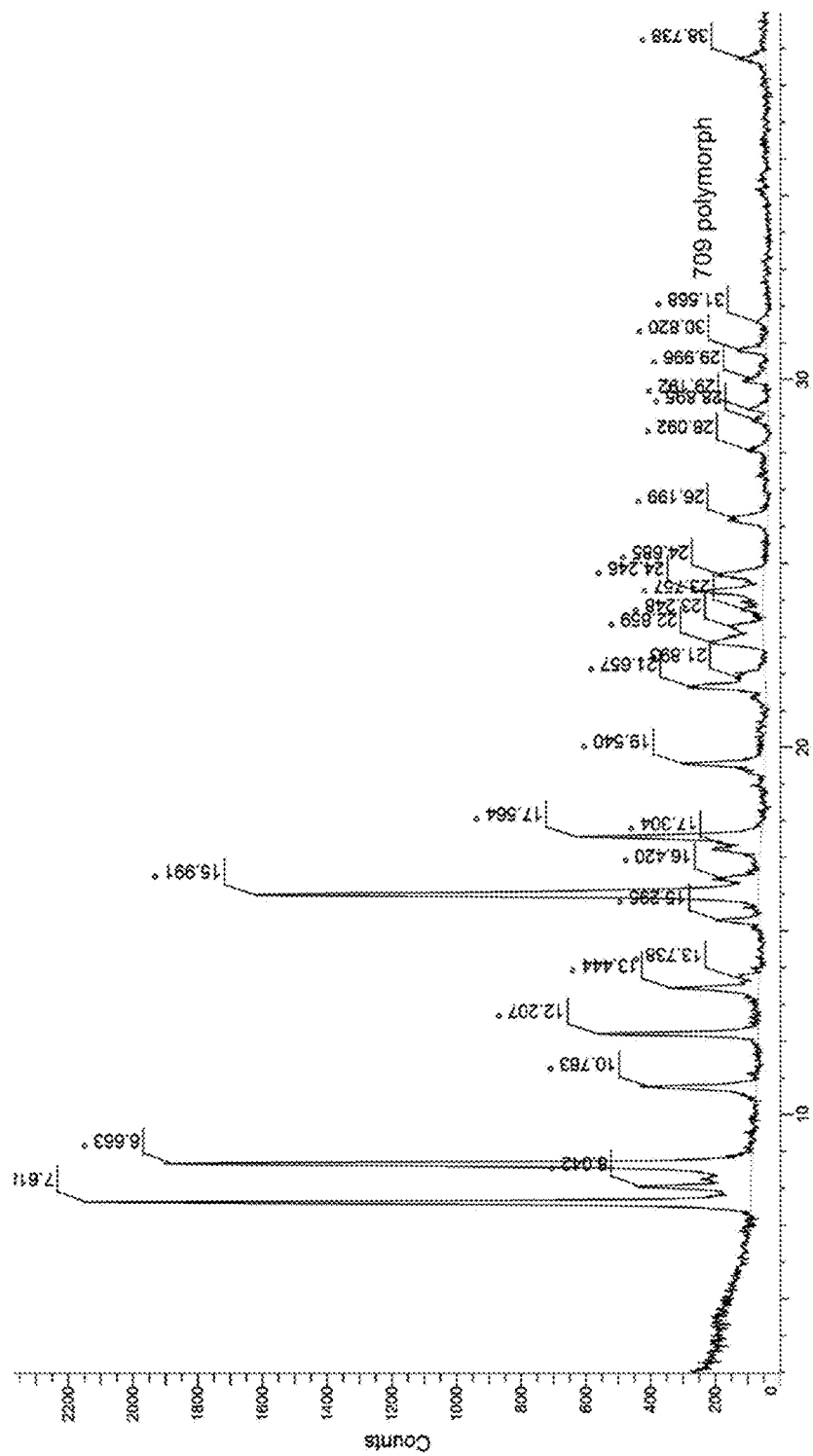
FIG. 5 shows the X-ray powder diffraction (XRPD) pattern for polymorph Form II of the compound of Formula I.

FIG. 5 shows the X-ray powder diffraction (XRPD) pattern for polymorph Form II of the compound of Formula I.

Figure 6:
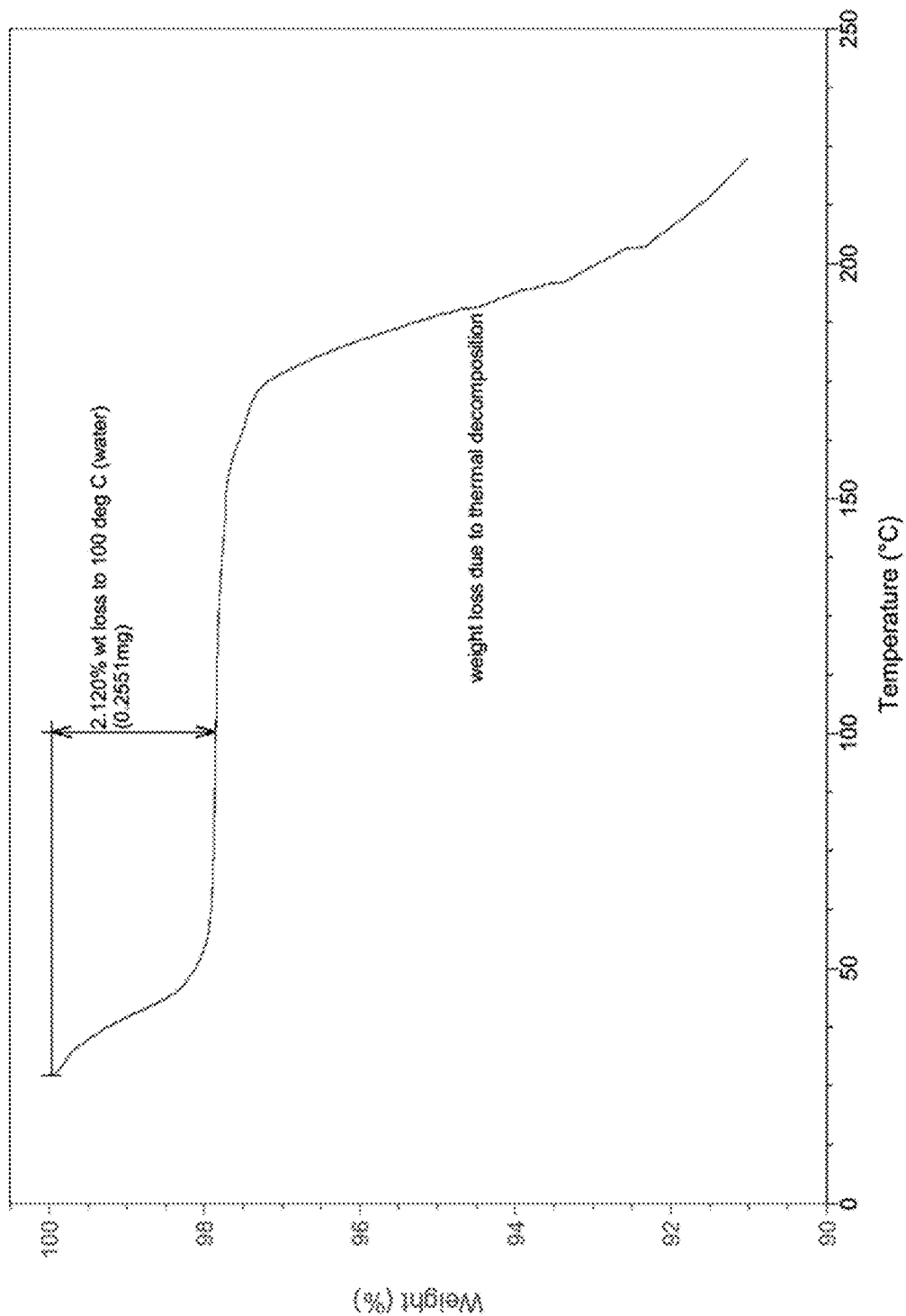
FIG. 6 shows the thermogravimetric analysis (TGA) thermogram for polymorph Form II of the compound of Formula I.

FIG. 6 shows the thermogravimetric analysis (TGA) thermogram for polymorph Form II of the compound of Formula I.

Provided herein, in one aspect, is polymorph Form II of (R)-2-((1-(2-(4-methoxy-3-(2-morpholinoethoxy)phenyl)-5-methylthiazol-4-yl)ethyl)thio)pyrimidine-4,6-diamine.

Some embodiments provided a composition comprising polymorph Form II of (R)-2-((1-(2-(4-methoxy-3-(2-morpholinoethoxy)phenyl)-5-methylthiazol-4-yl)ethyl)thio)pyrimidine-4,6-diamine. In some embodiments, polymorph Form II of (R)-2-((1-(2-(4-methoxy-3-(2-morpholinoethoxy)phenyl)-5-methylthiazol-4-yl)ethyl)thio)pyrimidine-4,6-diamine is characterized as having:

(a) an X-ray powder diffraction pattern comprising peaks at 7.6±0.2° 2-θ, 8.7±0.2° 2-θ, and 16.0±0.2° 2-θ, as measured by X-ray powder diffraction using an X-ray wavelength of 1.5406 Å;
(b) an X-ray powder diffraction pattern substantially as set forth in FIG. 5;
(c) a differential scanning calorimetry (DSC) thermogram comprising an endotherm in the range of about 150 to about 170° C.;
(d) a differential scanning calorimetry (DSC) thermogram further comprising an endotherm in the range of about 25 to about 60° C.;
(e) a differential scanning calorimetry (DSC) thermogram substantially as set forth in FIG. 4;
(f) a thermogravimetric analysis (TGA) thermogram substantially as set forth in FIG. 6; or
(g) combinations thereof.

In some embodiments, polymorph Form II is characterized by an X-ray powder diffraction pattern substantially as set forth in FIG. 5.

In some embodiments, polymorph Form II is characterized by an X-ray powder diffraction pattern comprising peaks at 7.6±0.2° 2-θ, 8.7±0.2° 2-θ, and 16.0±0.2° 2-θ, as measured by X-ray powder diffraction using an X-ray wavelength of 1.5406 Å. In some embodiments, polymorph Form II is characterized by an X-ray powder diffraction pattern comprising peaks at 7.6±0.1° 2-θ, 8.7±0.1° 2-θ, and 16.0±0.1° 2-θ, as measured by X-ray powder diffraction using an X-ray wavelength of 1.5406 Å. In some embodiments, polymorph Form II is characterized by an X-ray powder diffraction pattern comprising peaks at about 7.6° 2-θ, about 8.7° 2-θ, and about 16.0° 2-θ, as measured by X-ray powder diffraction using an X-ray wavelength of 1.5406 Å.

In some embodiments, the X-ray powder diffraction pattern further comprises at least one peak selected from 12.2±0.2° 2-θ, 17.6±0.2° 2-θ, and 19.5±0.2° 2-θ, as measured by X-ray powder diffraction using an X-ray wavelength of 1.5406 Å. In some embodiments, the X-ray powder diffraction pattern further comprises at least one peak selected from 12.2±0.1° 2-θ, 17.6±0.1° 2-θ, and 19.5±0.1° 2-θ, as measured by X-ray powder diffraction using an X-ray wavelength of 1.5406 Å. In some embodiments, the X-ray powder diffraction pattern further comprises at least one peak selected from about 12.2° 2-θ, about 17.6° 2-θ, and about 19.5° 2-θ, as measured by X-ray powder diffraction using an X-ray wavelength of 1.5406 Å.

In some embodiments, the X-ray powder diffraction pattern further comprises at least one peak selected from 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern further comprises at least one peak selected from 21.7±0.1° 2-θ, 10.8±0.1° 2-θ, and 13.4±0.1° 2-θ, as measured by X-ray powder diffraction using an X-ray wavelength of 1.5406 Å. In some embodiments, the X-ray powder diffraction pattern further comprises at least one peak selected from about 21.7° 2-θ, about 10.8° 2-θ, and about 13.4° 2-θ, as measured by X-ray powder diffraction using an X-ray wavelength of 1.5406 Å.

In some embodiments, the X-ray powder diffraction pattern comprises at least one peak selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least two peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least three peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least four peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least five peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least six peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least seven peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises at least eight peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises peaks at 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å. In some embodiments, the X-ray powder diffraction pattern comprises peaks at 7.6±0.1° 2-θ, 8.7±0.1° 2-θ, 16.0±0.1° 2-θ, 12.2±0.1° 2-θ, 17.6±0.1° 2-θ, 19.5±0.1° 2-θ, 21.7±0.1° 2-θ, 10.8±0.1° 2-θ, and 13.4±0.1° 2-θ, as measured by X-ray powder diffraction using an X-ray wavelength of 1.5406 Å. In some embodiments, the X-ray powder diffraction pattern comprises peaks at about 7.6° 2-θ, about 8.7° 2-θ, about 16.0° 2-θ, about 12.2° 2-θ, about 17.6° 2-θ, about 19.5° 2-θ, about 21.7° 2-θ, about 10.8° 2-θ, and about 13.4° 2-θ, as measured by X-ray powder diffraction using an X-ray wavelength of 1.5406 Å.

In some embodiments, polymorph Form II is characterized by a differential scanning calorimetry (DSC) thermogram substantially as set forth in FIG. 4. In some embodiments, polymorph Form II is characterized by a differential scanning calorimetry (DSC) thermogram comprising an endotherm in the range of about 150 to about 170° C.

In some embodiments, polymorph Form I is characterized by a differential scanning calorimetry (DSC) thermogram comprising an endotherm at about 150-170° C., 150-168° C., 150-166° C., 150-164° C., 150-162° C., 150-160° C., 150-158° C., 150-156° C., 150-154° C., 150-152° C., 152-170° C., 152-168° C., 152-166° C., 152-164° C., 152-162° C., 152-160° C., 152-158° C., 152-156° C., 152-154° C., 154-170° C., 154-168° C., 154-166° C., 154-164° C., 154-162° C., 154-160° C., 154-158° C., 154-156° C., 156-170° C., 156-168° C., 156-166° C., 156-164° C., 156-162° C., 156-160° C., 156-158° C., 158-170° C., 158-168° C., 158-166° C., 158-164° C., 158-162° C., 158-160° C., 160-170° C., 160-168° C., 160-166° C., 160-164° C., 160-162° C., 162-170° C., 162-168° C., 162-166° C., 162-164° C., 164-170° C., 164-168° C., 164-166° C., 166-170° C., 166-168° C., or 168-170° C. In some embodiments, polymorph Form I is characterized by a differential scanning calorimetry (DSC) thermogram comprising an endotherm at about 150-155° C., for example at about 150° C., 151° C., 152° C., 153° C., 154° C., or 155° C. In some embodiments, the polymorph Form I has a melting point of about 150-155° C.

In some embodiments, polymorph Form II is characterized by a differential scanning calorimetry (DSC) thermogram further comprising an endotherm at about 25-60° C., 25-58° C., 25-56° C., 25-54° C., 25-52° C., 25-50° C., 25-48° C., 25-46° C., 25-44° C., 25-42° C., 25-40° C., 25-38° C., 25-36° C., 25-34° C., 25-32° C., 25-30° C., 30-60° C., 30-58° C., 30-56° C., 30-54° C., 30-52° C., 30-50° C., 30-48° C., 30-46° C., 30-44° C., 30-42° C., 30-40° C., 30-38° C., 30-36° C., 30-34° C., 30-32° C., 32-60° C., 32-58° C., 32-56° C., 32-54° C., 32-52° C., 32-50° C., 32-48° C., 32-46° C., 32-44° C., 32-42° C., 32-40° C., 32-38° C., 32-36° C., 32-34° C., 34-60° C., 34-58° C., 34-56° C., 34-54° C., 34-52° C., 34-50° C., 34-48° C., 34-46° C., 34-44° C., 34-42° C., 34-40° C., 34-38° C., 34-36° C., 36-60° C., 36-58° C., 36-56° C., 36-54° C., 36-52° C., 36-50° C., 36-48° C., 36-46° C., 36-44° C., 36-42° C., 36-40° C., 36-38° C., 38-60° C., 38-58° C., 38-56° C., 38-54° C., 38-52° C., 38-50° C., 38-48° C., 38-46° C., 38-44° C., 38-42° C., 38-40° C., 40-60° C., 40-58° C., 40-56° C., 40-54° C., 40-52° C., 40-50° C., 40-48° C., 40-46° C., 40-44° C., 40-42° C., 42-60° C., 42-58° C., 42-56° C., 42-54° C., 42-52° C., 42-50° C., 42-48° C., 42-46° C., 42-44° C., 44-60° C., 44-58° C., 44-56° C., 44-54° C., 44-52° C., 44-50° C., 44-48° C., 44-46° C., 46-60° C., 46-58° C., 46-56° C., 46-54° C., 46-52° C., 46-50° C., 46-48° C., 48-60° C., 48-58° C., 48-56° C., 48-54° C., 48-52° C., 48-50° C., 50-60° C., 50-58° C., 50-56° C., 50-54° C., 50-52° C., 52-60° C., 52-58° C., 52-56° C., 52-54° C., 54-60° C., 54-58° C., 54-56° C., 56-60° C., 56-58° C., or 58-60° C.

In some embodiments, polymorph Form II is characterized by a thermogravimetric analysis (TGA) thermogram substantially as set forth in FIG. 6. In some embodiments, polymorph Form II decomposes above a temperature of about 50° C., about 100° C., about 150° C., about 200° C., about 250° C., about 300° C., about 350° C., or about 400° C. In some embodiments, polymorph Form II decomposes above a temperature of about 150° C.

In some embodiments, polymorph Form II is stable at below room temperature. In some examples, polymorph Form II can be stored at about 2-8° C. for an extended period of time without significant chemical degradation or change in the crystalline form. In some examples, polymorph Form II can be stored at about 2-8° C. for a time period of at least about 1 day, 1 week, 1 month, 3 months, 6 months, 9 months, 12 months, 15 months, 18 months, 21 months, 24 months, 27 months, 30 months, 33 months, or 36 months. In some examples, polymorph Form II can be stored at about 2-8° C. for a time period of more than about 36 months. In some examples, polymorph Form II can be stored at about 2-8° C. for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, 6-7 days, 1-2 weeks, 1-3 weeks, 1-4 weeks, 2-3 weeks, 2-4 weeks, 3-4 weeks, 1-3 months, 1-6 months, 1-9 months, 1-12 months, 1-15 months, 1-18 months, 1-21 months, 1-24 months, 1-27 months, 1-30 months, 1-33 months, 1-36 months, 3-6 months, 3-9 months, 3-12 months, 3-15 months, 3-18 months, 3-21 months, 3-24 months, 3-27 months, 3-30 months, 3-33 months, 3-36 months, 6-9 months, 6-12 months, 6-15 months, 6-18 months, 6-21 months, 6-24 months, 6-27 months, 6-30 months, 6-33 months, 6-36 months, 9-12 months, 9-15 months, 9-18 months, 9-21 months, 9-24 months, 9-27 months, 9-30 months, 9-33 months, 9-36 months, 12-15 months, 12-18 months, 12-21 months, 12-24 months, 12-27 months, 12-30 months, 12-33 months, 12-36 months, 15-18 months, 15-21 months, 15-24 months, 15-27 months, 15-30 months, 15-33 months, 15-36 months, 18-21 months, 18-24 months, 18-27 months, 18-30 months, 18-33 months, 18-36 months, 21-24 months, 21-27 months, 21-30 months, 21-33 months, 21-36 months, 24-27 months, 24-30 months, 24-33 months, 24-36 months, 27-30 months, 27-33 months, 27-36 months, 30-33 months, 30-36 months, or 33-36 months. In some examples, polymorph Form II can be stored at about 2-8° C. for a time period of at least 1 day, 1 week, 1 month, 3 months, 6 months, 9 months, 12 months, 15 months, 18 months, 21 months, 24 months, 27 months, 30 months, 33 months, or 36 months.

In some embodiments, polymorph Form II is stable at room temperature and relative humidity. In some examples, polymorph Form II can be stored at about 25° C. and at about 60% RH for an extended period of time without significant chemical degradation or change in the crystalline form. In some examples, polymorph Form II can be stored at about 25° C. and at about 60% for a time period of at least about 1 day, 1 week, 1 month, 2 months, 3 months, 4 months, 5 months, or 6 months. In some examples, polymorph Form II can be stored at about 25° C. and at about 60% RH for a time period of more than about 6 months. In some examples, polymorph Form II can be stored at about 25° C. and at about 60% RH for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, 6-7 days, 1-2 weeks, 1-3 weeks, 1-4 weeks, 2-3 weeks, 2-4 weeks, 3-4 weeks, 1-2 months, 1-3 months, 1-4 months, 1-5 months, 1-6 months, 2-3 months, 2-4 months, 2-5 months, 2-6 months, 3-4 months, 3-5 months, 3-6 months, 4-5 months, 4-6 months, or 5-6 months. In some examples, polymorph Form II can be stored at about 25° C. and at about 60% RH for a time period of at least 1 day, 1 week, 1 month, 2 months, 3 months, 4 months, 5 months, or 6 months.

In some embodiments, polymorph Form II is stable at temperatures above the room temperature and/or at high relative humidity (RH). In some examples, polymorph Form II can be stored at about 40° C. and at about 75% RH for an extended period of time without significant chemical degradation or change in the crystalline form. In some examples, polymorph Form II can be stored at about 40° C. and at about 75% RH for a time period of at least about 1 day, 2 days, 3 days, or 7 days. In some examples, polymorph Form II can be stored at about 40° C. and at about 75% RH for a time period of more than about 7 days. In some examples, polymorph Form II can be stored at about 40° C. and at about 75% RH for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, or 6-7 days. In some examples, polymorph Form II can be stored at about 40° C. and at about 75% RH for a time period of at 1 day, 2 days, 3 days, or 7 days.

In some embodiments, polymorph Form II is stable at temperatures above the room temperature and/or at high relative humidity (RH). In some examples, polymorph Form II can be stored at about 60° C. for an extended period of time without significant chemical degradation or change in the crystalline form. In some examples, polymorph Form II can be stored at about 60° C. for a time period of at least about 1 day, 2 days, 3 days, or 7 days. In some examples, polymorph Form II can be stored at about 60° C. for a time period of more than about 7 days. In some examples, polymorph Form II can be stored at 60° C. for a time period of 1-2 days, 1-3 days, 1-4 days, 1-5 days, 1-6 days, 1-7 days, 2-3 days, 2-4 days, 2-5 days, 2-6 days, 2-7 days, 3-4 days, 3-5 days, 3-6 days, 3-7 days, 4-5 days, 4-6 days, 4-7 days, 5-6 days, 5-7 days, or 6-7 days. In some examples, polymorph Form II can be stored at about 60° C. for a time period of at 1 day, 2 days, 3 days, or 7 days.

Methods of Making the Compound of Formula I and Polymorphic Forms Thereof

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the pyrazole compounds described herein is P. H. Stahl & C. G. Wermuth "Handbook of Pharmaceutical Salts", Verlag Helvetica Chimica Acta, Zurich, 2002.

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Provided herein, in one aspect, are methods of making one or more polymorphs of the compound of Formula I:

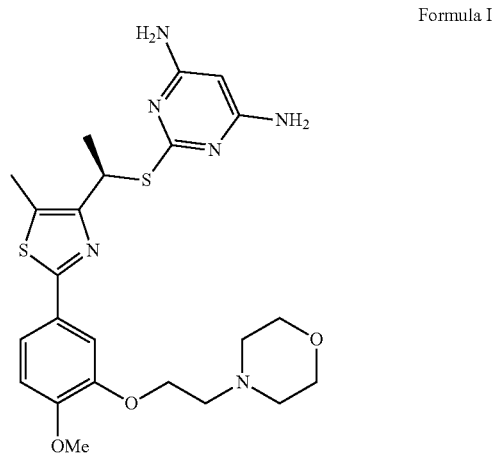 [SMILES: COc1ccc(-c2nc([C@@H](C)Sc3nc(N)cc(N)n3)c(C)s2)cc1OCCN1CCOCC1]

Formula I

The compound of Formula I may be prepared as previously described in U.S. Pat. Nos. 9,598,404, 9,981,961, 9,688,673, WO 2016/130581, U.S. Pat. No. 10,570,124, and WO 2016/130562. In some embodiments, the compound of Formula I is prepared according to the examples herein.

The polymorphs provided herein are not limited by the starting materials used to produce the compound of Formula I.

Provided herein, in one aspect, are methods of making polymorphs of the compound of Formula I, or a pharmaceutically acceptable salt and/or solvate thereof, either by isolation of the desired polymorph as the first solid form after synthesis of the compound of Formula I, or alternatively, by isolation of the desired polymorph as a transition from a prior solid form of the compound of Formula I. Transitions from one form to another are within the scope of this disclosure because they can be an alternative manufacturing method for obtaining the form desired for the production of the medicinal preparations.

Polymorphs of the compound of Formula I, according to the methods provided herein can be selected from polymorph Form I, polymorph Form II, and mixtures thereof.

Isolation and purification of the chemical entities and intermediates described herein can be performed, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples below. However, other equivalent separation or isolation procedures can also be used. Prior to crystallization, the compound of Formula I may be isolated in about 50% chemical purity, 55% chemical purity, 60% chemical purity, 65% chemical purity, 70% chemical purity, 75% chemical purity, 80% chemical purity, 90% chemical purity, 91% chemical purity, 92% purity, 93% chemical purity, 94% chemical purity, 95% chemical purity, 96% chemical purity, 97% chemical purity, 98% chemical purity, 99% chemical purity, about 98% chemical purity, or about 100% chemical purity.

In some embodiments, the crystalline forms disclosed herein are obtained by crystallizing the compound of Formula I with a chemical purity of less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 78%, less than about 76%, less than about 74%, less than about 72%, or less than about 70%. In some embodiments, the crystalline forms are obtained by crystallizing the compound of Formula I with a chemical purity in the range of about 70% to about 99%, 80% to about 96%, about 85% to about 96%, about 90% to about 96%, about 80% to 98%, about 85% to about 98%, about 90% to about 98%, about 92% to about 98%, about 94% to 98%, or about 96% to about 98%.

Preparation of Polymorph Form I

In one embodiment, the desired polymorph is polymorph Form I of a maleate salt of the compound of Formula I, and the isolating step involves recrystallization of crude reaction product from a mono-solvent system. In some embodiments, the desired polymorph is polymorph Form I of a maleate salt of the compound of Formula I, and the isolating step involves recrystallization of crude product from a binary, tertiary, or greater solvent system, collectively understood as a multi-solvent system. In some embodiments, the desired polymorph is polymorph Form I of a maleate salt of the compound of Formula I, and the isolating step involves crystallization from a mono- or multi-solvent system, where the crystallization involves dissolving the compound of Formula I and maleic acid in the mono- or multi-solvent system at a temperature above ambient temperature. In some examples, the dissolving of the compound of Formula I and maleic acid in the mono- or multi-solvent system is performed at a temperature of about 40-90° C., 45-90° C., 50-90° C., 55-90° C., 60-90° C., 65-90° C., 70-90° C., 75-90° C., 40-85° C., 45-85° C., 50-85° C., 55-85° C., 60-85° C., 65-85° C., 70-85° C., 75-85° C., 80-85° C., 40-80° C., 45-80° C., 50-80° C., 55-80° C., 60-80° C., 65-80° C., 70-80° C., 75-80° C., 40-75° C., 45-75° C., 50-75° C., 55-75° C., 60-75° C., 65-75° C., 70-75° C., 40-70° C., 45-70° C., 50-70° C., 55-70° C., 60-70° C., 65-70° C., 40-65° C., 45-65° C., 50-65° C., 55-65° C., 60-65° C., 40-60° C., 45-60° C., 50-60° C., 55-60° C., 40-55° C., 45-55° C., 50-55° C., 40-50° C., or 45-50° C. In some examples, the recrystallization solvent comprises ethanol/ethyl acetate and the dissolving of the compound of Formula I and maleic acid in the solvent is performed at a temperature of about 60° C. Any suitable amount of solvent can be used for dissolving the compound of Formula I and maleic acid. In some embodiments, the amount of solvent (e.g., 1:1 ethanol/ethyl acetate) used to dissolve the compound of Formula I and maleic acid is from about 1-10 mL per gram of the compound of Formula I. For example, in some embodiments, the amount of solvent used for dissolving the compound of Formula I is 7.3 mL per gram of the compound of Formula I. In some examples, the recrystallization solvent comprises ethanol/ethyl acetate, the dissolving of the compound of Formula I and maleic acid in the solvent system is performed at a temperature of about 60° C., and the amount of solvent used for dissolving is about 7.3 mL/g of the compound of Formula I.

In some embodiments, the crystallization further involves actively cooling the heated solution containing the dissolved maleate salt of the compound of Formula I, for example to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the crystallization further involves actively cooling the heated solution containing the dissolved maleate salt of the compound of Formula I to a temperature of about 25° C. In some embodiments, the solution containing the dissolved maleate salt of the compound of Formula I is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In some embodiments, the crystallization further involves actively cooling the heated solution containing the dissolved maleate salt of the compound of Formula I, for example to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the crystallization further involves actively cooling the heated solution containing the dissolved maleate salt of the compound of Formula I to a temperature of about 0° C. In some embodiments, the solution containing the dissolved maleate salt of the compound of Formula I is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In some embodiments, the crystallization further involves filtering the solution containing the obtained crystals of the maleate salt of the compound of Formula I. In some embodiments, the crystallization optionally involves washing the obtained crystals by a solvent, for example by the recrystallization solvent one or more times. In some embodiments, the crystallization optionally involves drying the obtained crystals, for example under vacuum at a temperature of about 55° C.

In some embodiments, the chemical purity of polymorph Form I is greater than 60%, 70%, 80%, 90%, 95%, or 99%. In some embodiments, the chemical purity of polymorph Form I is greater than about 90%. In some embodiments, the chemical purity of polymorph Form I is greater than about 95%. In some embodiments, the chemical purity of polymorph Form I greater than about 99%. The chemical purity of polymorph Form I may be measured by any available analytical technique, for example by HPLC analysis.

Preparation of Polymorph Form II

In one embodiment, the desired polymorph is polymorph Form II of a maleate salt of the compound of Formula I, and the isolating step involves recrystallization of crude reaction product from a mono-solvent system. In some embodiments, the desired polymorph is polymorph Form II of a maleate salt of the compound of Formula I, and the isolating step involves recrystallization of crude product from a binary, tertiary, or greater solvent system, collectively understood as a multi-solvent system. In some embodiments, the desired polymorph is polymorph Form II of a maleate salt of the compound of Formula I, and the isolating step involves crystallization from a mono- or multi-solvent system, where the crystallization involves dissolving the maleate salt of the compound of Formula I in the mono- or multi-solvent system at a temperature above ambient temperature. In some examples, the dissolving of the maleate salt of the compound of Formula I in the mono- or multi-solvent system is performed at a temperature of about 40-90° C., 45-90° C., 50-90° C., 55-90° C., 60-90° C., 65-90° C., 70-90° C., 75-90° C., 40-85° C., 45-85° C., 50-85° C., 55-85° C., 60-85° C., 65-85° C., 70-85° C., 75-85° C., 80-85° C., 40-80° C., 45-80° C., 50-80° C., 55-80° C., 60-80° C., 65-80° C., 70-80° C., 75-80° C., 40-75° C., 45-75° C., 50-75° C., 55-75° C., 60-75° C., 65-75° C., 70-75° C., 40-70° C., 45-70° C., 50-70° C., 55-70° C., 60-70° C., 65-70° C., 40-65° C., 45-65° C., 50-65° C., 55-65° C., 60-65° C., 40-60° C., 45-60° C., 50-60° C., 55-60° C., 40-55° C., 45-55° C., 50-55° C., 40-50° C., or 45-50° C. In some examples, the recrystallization solvent comprises 1:1 DCM/methanol and the dissolving of the maleate salt of the compound of Formula I in the solvent is performed at a temperature of about 45° C. Any suitable amount of solvent can be used for dissolving the maleate salt of the compound of Formula I. In some embodiments, the amount of solvent (e.g., 1:1 DCM/methanol) used to dissolve the maleate salt of the compound is from about 1-20 mL per gram of the maleate salt of the compound of Formula I. For example, in some embodiments, the amount of solvent used for dissolving the maleate salt of the compound of Formula I is 7.4 mL per gram of the maleate salt of the compound of Formula I. In some examples, the recrystallization solvent comprises 1:1 DCM/methanol, the dissolving of the maleate salt of the compound of Formula I in the solvent system is performed at a temperature of about 45° C., and the amount of solvent used for dissolving is about 7.4 mL/g of the maleate salt of the compound of Formula I.

In some embodiments, the crystallization further involves actively cooling the heated solution containing the dissolved maleate salt of the compound of Formula I, for example to a temperature of about 0-40° C., 0-30° C., 0-20° C., 0-10° C., 10-40° C., 10-30° C., 10-20° C., 20-40° C., 20-30° C., 20-10° C., or 30° C.-40° C. In some embodiments, the crystallization further involves actively cooling the heated solution containing the dissolved maleate salt of the compound of Formula I to a temperature of about 5° C. In some embodiments, the solution containing the dissolved maleate salt of the compound of Formula I is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In some embodiments, the crystallization further involves filtering the solution containing the obtained crystals of the maleate salt of the compound of Formula I. In some embodiments, the crystallization optionally involves washing the obtained crystals by a solvent, for example by the recrystallization solvent one or more times. In some embodiments, the crystallization optionally involves drying the obtained crystals, for example under vacuum at a temperature of about 70° C.

In some embodiments, the chemical purity of polymorph Form II is greater than 60%, 70%, 80%, 90%, 95%, or 99%. In some embodiments, the chemical purity of polymorph Form II is greater than about 90%. In some embodiments, the chemical purity of polymorph Form II is greater than about 95%. In some embodiments, the chemical purity of polymorph Form II greater than about 99%. The chemical purity of polymorph Form II may be measured by any available analytical technique, for example by HPLC analysis.

In some embodiments, polymorph Form II is dry. In some embodiments, polymorph Form II is non-solvated. In some embodiments, polymorph Form II is non-hydrated. In some embodiments, polymorph Form II is anhydrous. In some embodiments, polymorph Form II is solvated. In some embodiments, polymorph Form II is hydrated.

Pharmaceutical Compositions

The disclosure provides compositions, including pharmaceutical compositions, comprising one or more crystalline forms of the present invention.

In some embodiments, the ratio of desired crystalline form such as polymorph Form I to all other crystalline forms in a composition is greater than about 1:1, 2:1, 3:1, 4:1, 5:1, 6:1, 7:1, 8:1, 9:1, or more w/w. In other embodiments, the ratio of polymorph Form II to all other polymorphs is greater than about 1:1, 2:1, 3:1, 4:1, 5:1, 6:1, 7:1, 8:1, 9:1, or more w/w.

In some embodiments, the one or more polymorphs of the compound of Formula I are formulated into pharmaceutical compositions. In specific embodiments, pharmaceutical compositions are formulated in a conventional manner using one or more physiologically acceptable carriers comprising excipients and auxiliaries which facilitate processing of the active compounds/polymorphs into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

Provided herein are pharmaceutical compositions comprising one or more polymorphs of the compound of Formula I and a pharmaceutically acceptable diluent(s), excipient(s), or carrier(s). In certain embodiments, the one or more polymorphs of the compound of Formula I are administered as pharmaceutical compositions in which the one or more polymorphs are mixed with other active ingredients, as in combination therapy. Encompassed herein are all combinations of actives set forth in the combination therapies section below and throughout this disclosure. In specific embodiments, the pharmaceutical compositions include one or more polymorphs of the compound of Formula I.

A pharmaceutical composition, as used herein, refers to a mixture of one or more polymorphs of the compound of Formula I with other chemical components, such as carriers, stabilizers, diluents, dispersing agents, suspending agents, thickening agents, and/or excipients. In certain embodiments, the pharmaceutical composition facilitates administration of the polymorphs to an organism. In some embodiments, in practicing the methods of treatment or use provided herein, therapeutically effective amounts of one or more polymorphs of the compound of Formula I are administered in a pharmaceutical composition to a mammal having a disease or condition to be treated. In specific embodiments, the mammal is a human. In certain embodiments, therapeutically effective amounts vary depending on the severity of the disease, the age and relative health of the subject and other factors. The one or more polymorphs of the compound of Formula I described herein are used singly or in combination with one or more therapeutic agents as components of mixtures.

In one embodiment, one or more polymorphs of the compound of Formula I are formulated in an aqueous solution. In specific embodiments, the aqueous solution is selected from, by way of example only, a physiologically compatible buffer, such as Hank's solution, Ringer's solution, or physiological saline buffer. In other embodiments, one or more polymorphs of the compound of Formula I are formulated for transmucosal administration. In specific embodiments, transmucosal formulations include penetrants that are appropriate to the barrier to be permeated. In still other embodiments wherein the one or more polymorphs described herein are formulated for other parenteral injections, appropriate formulations include aqueous or nonaqueous solutions. In specific embodiments, such solutions include physiologically compatible buffers and/or excipients.

In another embodiment, the polymorphs described herein are formulated for oral administration. The polymorphs of the compound of Formula I are formulated by combining the polymorphs with, e.g., pharmaceutically acceptable carriers or excipients. In some embodiments, the polymorphs described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the polymorphs described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the polymorphs described herein is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the polymorphs described herein are formulated for buccal or sublingual administration. Formulations suitable for buccal or sublingual administration include, by way of example only, tablets, lozenges, or gels. In still other embodiments, the polymorphs described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a polymorph of the compound of Formula I is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active polymorphs in water-soluble form. In additional embodiments, suspensions of the active polymorphs are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the polymorphs to allow for the preparation of highly concentrated solutions. Alternatively, in other embodiments, the active ingredient is in powder form for constitution with a suitable vehicle, e.g., sterile pyrogen-free water, before use.

In still other embodiments, the one or more polymorphs of the compound of Formula I are administered topically. The one or more polymorphs described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the one or more polymorphs of the compound of Formula I are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In some embodiments, such patches are constructed for continuous, pulsatile, or on demand delivery of pharmaceutical agents. In additional embodiments, the transdermal delivery of the one or more polymorphs of the compound of Formula I is accomplished by means of iontophoretic patches and the like. In certain embodiments, transdermal patches provide controlled delivery of the one or more polymorphs of the compound of Formula I. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the one or more polymorphs of the compound of Formula I are formulated for administration by inhalation. Various forms suitable for administration by inhalation include, but are not limited to, aerosols, mists or powders. Pharmaceutical compositions of the polymorphs of the compound of Formula I are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the one or more polymorphs of the compound of Formula I are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active polymorphs into preparations which can be used pharmaceutically. Proper formulation is dependent upon the route of administration chosen. Any pharmaceutically acceptable techniques, carriers, and excipients are optionally used as suitable. Pharmaceutical compositions comprising the one or more polymorphs of the compound of Formula I are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one polymorph of the compound of Formula I described herein as an active ingredient. The active ingredient is in free-acid or free-base form, or in a pharmaceutically acceptable salt form. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions, comprising the one or more polymorphs of the compound of Formula I described herein include formulating the polymorphs with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, a pharmaceutical composition comprising at least one polymorph of the compound of Formula I illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspension contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a polymorph of the compound of Formula I. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the polymorphs described herein are delivered using a sustained-release system, such as semipermeable matrices of solid hydrophobic polymers containing the therapeutic agent. Various sustained-release materials are useful herein. In some embodiments, sustained-release capsules release the polymorphs for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Treatment

Disclosed herein are methods of inhibiting a deoxycytidine kinase (dCK) activity comprising contacting a compound or polymorph detailed herein with the deoxycytidine kinase, either in vitro (e.g., in an enzymatic or a cell-based assay setting) or in vivo (e.g., in animal models or an individual subject in need of treatment). Compounds and polymorphs provided herein bind to a deoxycytidine kinase polypeptide and inhibit its activity. Thus in another aspect, provided are methods for inhibiting dCK activity and treating diseases and disorders where dCK activity is implicated.

In some embodiments, provided is a method for treating cancer in an individual comprising administering to the individual an effective amount of a compound or polymorph detailed herein, or a pharmaceutically acceptable salt thereof.

As used herein, the term "cancer" refers to all types of cancer, neoplasm, or malignant or benign tumors found in mammals, including leukemia, carcinomas and sarcomas. In some embodiments, cancer is a solid tumor cancer. In some embodiments, the cancer is metastatic. In some embodiments, the cancer is a liquid tumor cancer. In some embodiments, the liquid tumor cancer is a blood cancer. In some embodiments, the cancer is refractory. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved: myeloid (myelogenous), lymphoid (lymphogenous), or monocytic; and (3) the increase or non-increase in the number abnormal cells in the blood: leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present invention includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In some embodiments, the cancer is a liquid tumor. In some embodiments, the cancer is leukemia. In some embodiments, the cancer is acute lymphoblastic leukemia (ALL). In some embodiments, the cancer is lymphoma. In some embodiments, the cancer is a solid tumor. In some embodiments, the solid tumor is characterized by high levels of replication stress as determined by measuring gamma H2A.X expression. In some embodiments, the cancer is ovarian cancer, pancreatic cancer, lung cancer, glioblastoma, hepatocellular carcinoma, breast cancer, prostate cancer, or head and neck cancer. In some embodiments, the cancer is pancreatic cancer. In some embodiments, the cancer is ovarian cancer. In some embodiments, the cancer is lung cancer. In some embodiments, the cancer is glioblastoma. In some embodiments, the cancer is hepatocellular carcinoma. In some embodiments, the cancer is prostate cancer. In some embodiments, the cancer is head or neck cancer.

In some embodiments of this section, provided is a method for treating an immune disorder in an individual in need thereof comprising administering to the individual an effective amount of a compound detailed herein, or a pharmaceutically acceptable salt thereof. In some embodiments, the immune disorder is an autoimmune disorder or transplant rejection. In some embodiments, the autoimmune disorder is a T cell mediated autoimmune disorder. In some embodiments, the autoimmune disorder is selected from the group consisting of multiple sclerosis, lupus (including systemic lupus erythematosus), inflammatory bowel disease, rheumatoid arthritis and type 1 diabetes.

Provided herein, in another aspect, is a method of treating acute disseminated encephalomyelitis (ADEM) in a subject in need thereof, comprising administering a therapeutically effective amount of a compound of Formula I:

Formula I or a pharmaceutically acceptable salt thereof.

In some embodiments, the compound of Formula I is administered once daily. In some embodiments, the compound of Formula I is administered twice daily. In some embodiments, the administrations of the compound of Formula I are conducted twelve hours apart.

In some embodiments, the compound of Formula I is administered in a unit dosage form. In some embodiments, the unit dosage form comprises from about 0.5 to about 350 mg/kg of the compound of Formula I. In some embodiments, the unit dosage form comprises about 25 mg/kg of the compound of Formula I. In some embodiments, the unit dosage form comprises about 50 mg/kg of the compound of Formula I. In some embodiments, the unit dosage form comprises about 75 mg/kg of the compound of Formula I. In some embodiments, the unit dosage form comprises about 100 mg/kg of the compound of Formula I. In some embodiments, the unit dosage form comprises about 125 mg/kg of the compound of Formula I. In some embodiments, the unit dosage form comprises about 150 mg/kg of the compound of Formula I. In some embodiments, the unit dosage form comprises about 175 mg/kg of the compound of Formula I. In some embodiments, the unit dosage form comprises about 200 mg/kg of the compound of Formula I. In some embodiments, the unit dosage form comprises about 225 mg/kg of the compound of Formula I. In some embodiments, the unit dosage form comprises about 250 mg/kg of the compound of Formula I. In some embodiments, the unit dosage form comprises about 275 mg/kg of the compound of Formula I. In some embodiments, the unit dosage form comprises about 300 mg/kg of the compound of Formula I. In some embodiments, the unit dosage form comprises about 320 mg/kg of the compound of Formula I. In some embodiments, the unit dosage form comprises about 325 mg/kg of the compound of Formula I. In some embodiments, the unit dosage form comprises about 350 mg/kg of the compound of Formula I. In some embodiments, the unit dosage form comprises from about 0.5 to about 350 mg/subject of the compound of Formula I. In some embodiments, the unit dosage form comprises about 25 mg/subject of the compound of Formula I. In some embodiments, the unit dosage form comprises about 50 mg/subject of the compound of Formula I. In some embodiments, the unit dosage form comprises about 75 mg/subject of the compound of Formula I. In some embodiments, the unit dosage form comprises about 100 mg/subject of the compound of Formula I. In some embodiments, the unit dosage form comprises about 125 mg/subject of the compound of Formula I. In some embodiments, the unit dosage form comprises about 150 mg/subject of the compound of Formula I. In some embodiments, the unit dosage form comprises about 175 mg/subject of the compound of Formula I. In some embodiments, the unit dosage form comprises about 200 mg/subject of the compound of Formula I. In some embodiments, the unit dosage form comprises about 225 mg/subject of the compound of Formula I. In some embodiments, the unit dosage form comprises about 250 mg/subject of the compound of Formula I. In some embodiments, the unit dosage form comprises about 275 mg/subject of the compound of Formula I. In some embodiments, the unit dosage form comprises about 300 mg/subject of the compound of Formula I. In some embodiments, the unit dosage form comprises about 320 mg/subject of the compound of Formula I. In some embodiments, the unit dosage form comprises about 325 mg/subject of the compound of Formula I. In some embodiments, the unit dosage form comprises about 350 mg/subject of the compound of Formula I.

In some embodiments, the total amount of the compound of Formula I administered per day is from about 0.5 to about 350 mg/kg. In some embodiments, the total amount of the compound of Formula I administered per day is about 25 mg/kg. In some embodiments, the total amount of the compound of Formula I administered per day is about 50 mg/kg. In some embodiments, the total amount of the compound of Formula I administered per day is about 75 mg/kg. In some embodiments, the total amount of the compound of Formula I administered per day is about 100 mg/kg. In some embodiments, the total amount of the compound of Formula I administered per day is about 125 mg/kg. In some embodiments, the total amount of the compound of Formula I administered per day is about 150 mg/kg. In some embodiments, the total amount of the compound of Formula I administered per day is about 175 mg/kg. In some embodiments, the total amount of the compound of Formula I administered per day is about 200 mg/kg. In some embodiments, the total amount of the compound of Formula I administered per day is about 225 mg/kg. In some embodiments, the total amount of the compound of Formula I administered per day is about 250 mg/kg. In some embodiments, the total amount of the compound of Formula I administered per day is about 275 mg/kg. In some embodiments, the total amount of the compound of Formula I administered per day is about 300 mg/kg. In some embodiments, the total amount of the compound of Formula I administered per day is about 320 mg/kg. In some embodiments, the total amount of the compound of Formula I administered per day is about 325 mg/kg. In some embodiments, the total amount of the compound of Formula I administered per day is about 350 mg/kg.

In some embodiments, the total amount of the compound of Formula I administered per day is from about 0.5 to about 350 mg/subject. In some embodiments, the total amount of the compound of Formula I administered per day is about 25 mg/subject. In some embodiments, the total amount of the compound of Formula I administered per day is about 50 mg/subject. In some embodiments, the total amount of the compound of Formula I administered per day is about 75 mg/subject. In some embodiments, the total amount of the compound of Formula I administered per day is about 100 mg/subject. In some embodiments, the total amount of the compound of Formula I administered per day is about 125 mg/subject. In some embodiments, the total amount of the compound of Formula I administered per day is about 150 mg/subject. In some embodiments, the total amount of the compound of Formula I administered per day is about 175 mg/subject. In some embodiments, the total amount of the compound of Formula I administered per day is about 200 mg/subject. In some embodiments, the total amount of the compound of Formula I administered per day is about 225 mg/subject. In some embodiments, the total amount of the compound of Formula I administered per day is about 250 mg/subject. In some embodiments, the total amount of the compound of Formula I administered per day is about 275 mg/subject. In some embodiments, the total amount of the compound of Formula I administered per day is about 300 mg/subject. In some embodiments, the total amount of the compound of Formula I administered per day is about 320 mg/subject. In some embodiments, the total amount of the compound of Formula I administered per day is about 325 mg/subject. In some embodiments, the total amount of the compound of Formula I administered per day is about 350 mg/subject.

In some embodiments, the total amount of the compound of Formula I administered per day is from about 5 to about 350 mg. In some embodiments, the total amount of the compound of Formula I administered per day is about 25 mg. In some embodiments, the total amount of the compound of Formula I administered per day is about 50 mg. In some embodiments, the total amount of the compound of Formula I administered per day is about 75 mg. In some embodiments, the total amount of the compound of Formula I administered per day is about 100 mg. In some embodiments, the total amount of the compound of Formula I administered per day is about 125 mg. In some embodiments, the total amount of the compound of Formula I administered per day is about 150 mg. In some embodiments, the total amount of the compound of Formula I administered per day is about 175 mg. In some embodiments, the total amount of the compound of Formula I administered per day is about 200 mg. In some embodiments, the total amount of the compound of Formula I administered per day is about 225 mg. In some embodiments, the total amount of the compound of Formula I administered per day is about 250 mg. In some embodiments, the total amount of the compound of Formula I administered per day is about 275 mg. In some embodiments, the total amount of the compound of Formula I administered per day is about 300 mg. In some embodiments, the total amount of the compound of Formula I administered per day is about 320 mg. In some embodiments, the total amount of the compound of Formula I administered per day is about 325 mg. In some embodiments, the total amount of the compound of Formula I administered per day is about 350 mg.

In some embodiments, the compound of Formula I is formulated for oral administration. In some embodiments, the compound of Formula I is formulated as a tablet, a pill, a capsule, a powder, a liquid, a suspension, a solution, a suppository, or an aerosol. In some embodiments, the compound of Formula I is formulated as a tablet. In some embodiments, the compound of Formula I is formulated as a pill. In some embodiments, the compound of Formula I is formulated as a capsule. In some embodiments, the compound of Formula I is formulated as a powder. In some embodiments, the compound of Formula I is formulated as a liquid. In some embodiments, the compound of Formula I is formulated as a suspension. In some embodiments, the compound of Formula I is formulated as a suppository. In some embodiments, the compound of Formula I is formulated as an aerosol.

In some embodiments, the compound of Formula I is formulated as a solution. In some embodiments, the solution comprises from about 1 to about 50 mg/mL of the compound of Formula I. In some embodiments, the solution comprises about 5 mg/mL of the compound of Formula I. In some embodiments, the solution comprises about 10 mg/mL of the compound of Formula I. In some embodiments, the solution comprises about 15 mg/mL of the compound of Formula I. In some embodiments, the solution comprises about 20 mg/mL of the compound of Formula I. In some embodiments, the solution comprises about 25 mg/mL of the compound of Formula I. In some embodiments, the solution comprises about 30 mg/mL of the compound of Formula I. In some embodiments, the solution comprises about 35 mg/mL of the compound of Formula I. In some embodiments, the solution comprises about 40 mg/mL of the compound of Formula I. In some embodiments, the solution comprises about 45 mg/mL of the compound of Formula I. In some embodiments, the solution comprises about 50 mg/mL of the compound of Formula I.

In some embodiments, the administration of the compound of Formula I results in a decrease in interferon gamma (IFNγ) levels in the subject.

Provided herein, in another aspect, is a method of treating an autoimmune disease or disorder in a subject in need thereof, comprising administering a therapeutically effective amount of a compound of Formula I:

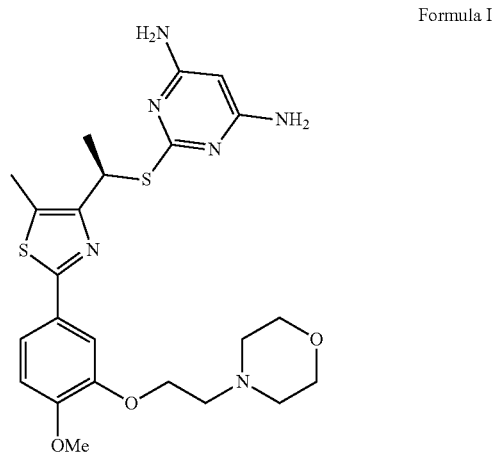 [SMILES: COc1ccc(-c2nc([C@@H](C)Sc3nc(N)cc(N)n3)c(C)s2)cc1OCCN1CCOCC1]

Formula I or a pharmaceutically acceptable salt thereof, wherein the compound of Formula I is administered once daily.

In some embodiments, the disease or disorder is multiple sclerosis. In some embodiments, the disease or disorder is optic neuritis. In some embodiments, the disease or disorder is acute disseminated encephalomyelitis (ADEM).

In some embodiments, the compound of Formula I is administered in a unit dosage form. In some embodiments, the unit dosage form comprises from about 0.5 to about 350 mg/kg of the compound of Formula I. In some embodiments, the unit dosage form comprises about 25 mg/kg of the compound of Formula I. In some embodiments, the unit dosage form comprises about 50 mg/kg of the compound of Formula I. In some embodiments, the unit dosage form comprises about 75 mg/kg of the compound of Formula I. In some embodiments, the unit dosage form comprises about 100 mg/kg of the compound of Formula I. In some embodiments, the unit dosage form comprises about 125 mg/kg of the compound of Formula I. In some embodiments, the unit dosage form comprises about 150 mg/kg of the compound of Formula I. In some embodiments, the unit dosage form comprises about 175 mg/kg of the compound of Formula I. In some embodiments, the unit dosage form comprises about 200 mg/kg of the compound of Formula I. In some embodiments, the unit dosage form comprises about 225 mg/kg of the compound of Formula I. In some embodiments, the unit dosage form comprises about 250 mg/kg of the compound of Formula I. In some embodiments, the unit dosage form comprises about 275 mg/kg of the compound of Formula I. In some embodiments, the unit dosage form comprises about 300 mg/kg of the compound of Formula I. In some embodiments, the unit dosage form comprises about 320 mg/kg of the compound of Formula I. In some embodiments, the unit dosage form comprises about 325 mg/kg of the compound of Formula I. In some embodiments, the unit dosage form comprises about 350 mg/kg of the compound of Formula I. In some embodiments, the unit dosage form comprises from about 0.5 to about 350 mg/subject of the compound of Formula I. In some embodiments, the unit dosage form comprises about 25 mg/subject of the compound of Formula I. In some embodiments, the unit dosage form comprises about 50 mg/subject of the compound of Formula I. In some embodiments, the unit dosage form comprises about 75 mg/subject of the compound of Formula I. In some embodiments, the unit dosage form comprises about 100 mg/subject of the compound of Formula I. In some embodiments, the unit dosage form comprises about 125 mg/subject of the compound of Formula I. In some embodiments, the unit dosage form comprises about 150 mg/subject of the compound of Formula I. In some embodiments, the unit dosage form comprises about 175 mg/subject of the compound of Formula I. In some embodiments, the unit dosage form comprises about 200 mg/subject of the compound of Formula I. In some embodiments, the unit dosage form comprises about 225 mg/subject of the compound of Formula I. In some embodiments, the unit dosage form comprises about 250 mg/subject of the compound of Formula I. In some embodiments, the unit dosage form comprises about 275 mg/subject of the compound of Formula I. In some embodiments, the unit dosage form comprises about 300 mg/subject of the compound of Formula I. In some embodiments, the unit dosage form comprises about 320 mg/subject of the compound of Formula I. In some embodiments, the unit dosage form comprises about 325 mg/subject of the compound of Formula I. In some embodiments, the unit dosage form comprises about 350 mg/subject of the compound of Formula I.

In some embodiments, the total amount of the compound of Formula I administered per day is from about 0.5 to about 350 mg/kg. In some embodiments, the total amount of the compound of Formula I administered per day is about 25 mg/kg. In some embodiments, the total amount of the compound of Formula I administered per day is about 50 mg/kg. In some embodiments, the total amount of the compound of Formula I administered per day is about 75 mg/kg. In some embodiments, the total amount of the compound of Formula I administered per day is about 100 mg/kg. In some embodiments, the total amount of the compound of Formula I administered per day is about 125 mg/kg. In some embodiments, the total amount of the compound of Formula I administered per day is about 150 mg/kg. In some embodiments, the total amount of the compound of Formula I administered per day is about 175 mg/kg. In some embodiments, the total amount of the compound of Formula I administered per day is about 200 mg/kg. In some embodiments, the total amount of the compound of Formula I administered per day is about 225 mg/kg. In some embodiments, the total amount of the compound of Formula I administered per day is about 250 mg/kg. In some embodiments, the total amount of the compound of Formula I administered per day is about 275 mg/kg. In some embodiments, the total amount of the compound of Formula I administered per day is about 300 mg/kg. In some embodiments, the total amount of the compound of Formula I administered per day is about 320 mg/kg. In some embodiments, the total amount of the compound of Formula I administered per day is about 325 mg/kg. In some embodiments, the total amount of the compound of Formula I administered per day is about 350 mg/kg.

In some embodiments, the total amount of the compound of Formula I administered per day is from about 0.5 to about 350 mg/subject. In some embodiments, the total amount of the compound of Formula I administered per day is about 25 mg/subject. In some embodiments, the total amount of the compound of Formula I administered per day is about 50 mg/subject. In some embodiments, the total amount of the compound of Formula I administered per day is about 75 mg/subject. In some embodiments, the total amount of the compound of Formula I administered per day is about 100 mg/subject. In some embodiments, the total amount of the compound of Formula I administered per day is about 125 mg/subject. In some embodiments, the total amount of the compound of Formula I administered per day is about 150 mg/subject. In some embodiments, the total amount of the compound of Formula I administered per day is about 175 mg/subject. In some embodiments, the total amount of the compound of Formula I administered per day is about 200 mg/subject. In some embodiments, the total amount of the compound of Formula I administered per day is about 225 mg/subject. In some embodiments, the total amount of the compound of Formula I administered per day is about 250 mg/subject. In some embodiments, the total amount of the compound of Formula I administered per day is about 275 mg/subject. In some embodiments, the total amount of the compound of Formula I administered per day is about 300 mg/subject. In some embodiments, the total amount of the compound of Formula I administered per day is about 320 mg/subject. In some embodiments, the total amount of the compound of Formula I administered per day is about 325 mg/subject. In some embodiments, the total amount of the compound of Formula I administered per day is about 350 mg/subject.

In some embodiments, the total amount of the compound of Formula I administered per day is from about 5 to about 350 mg. In some embodiments, the total amount of the compound of Formula I administered per day is about 25 mg. In some embodiments, the total amount of the compound of Formula I administered per day is about 50 mg. In some embodiments, the total amount of the compound of Formula I administered per day is about 75 mg. In some embodiments, the total amount of the compound of Formula I administered per day is about 100 mg. In some embodiments, the total amount of the compound of Formula I administered per day is about 125 mg. In some embodiments, the total amount of the compound of Formula I administered per day is about 150 mg. In some embodiments, the total amount of the compound of Formula I administered per day is about 175 mg. In some embodiments, the total amount of the compound of Formula I administered per day is about 200 mg. In some embodiments, the total amount of the compound of Formula I administered per day is about 225 mg. In some embodiments, the total amount of the compound of Formula I administered per day is about 250 mg. In some embodiments, the total amount of the compound of Formula I administered per day is about 275 mg. In some embodiments, the total amount of the compound of Formula I administered per day is about 300 mg. In some embodiments, the total amount of the compound of Formula I administered per day is about 320 mg. In some embodiments, the total amount of the compound of Formula I administered per day is about 325 mg. In some embodiments, the total amount of the compound of Formula I administered per day is about 350 mg.

In some embodiments, the compound of Formula I is formulated for oral administration. In some embodiments, the compound of Formula I is formulated as a tablet, a pill, a capsule, a powder, a liquid, a suspension, a solution, a suppository, or an aerosol. In some embodiments, the compound of Formula I is formulated as a tablet. In some embodiments, the compound of Formula I is formulated as a pill. In some embodiments, the compound of Formula I is formulated as a capsule. In some embodiments, the compound of Formula I is formulated as a powder. In some embodiments, the compound of Formula I is formulated as a liquid. In some embodiments, the compound of Formula I is formulated as a suspension. In some embodiments, the compound of Formula I is formulated as a suppository. In some embodiments, the compound of Formula I is formulated as an aerosol.

In some embodiments, the compound of Formula I is formulated as a solution. In some embodiments, the solution comprises from about 1 to about 50 mg/mL of the compound of Formula I. In some embodiments, the solution comprises about 5 mg/mL of the compound of Formula I. In some embodiments, the solution comprises about 10 mg/mL of the compound of Formula I. In some embodiments, the solution comprises about 15 mg/mL of the compound of Formula I. In some embodiments, the solution comprises about 20 mg/mL of the compound of Formula I. In some embodiments, the solution comprises about 25 mg/mL of the compound of Formula I. In some embodiments, the solution comprises about 30 mg/mL of the compound of Formula I. In some embodiments, the solution comprises about 35 mg/mL of the compound of Formula I. In some embodiments, the solution comprises about 40 mg/mL of the compound of Formula I. In some embodiments, the solution comprises about 45 mg/mL of the compound of Formula I. In some embodiments, the solution comprises about 50 mg/mL of the compound of Formula I.

In some embodiments, the administration of the compound of Formula I results in a decrease in interferon gamma (IFNγ) levels in the subject.

Combination Therapy

In some embodiments, provided is a method for treating cancer in an individual comprising administering to the individual an effective amount of a compound or polymorph detailed herein, or a pharmaceutically acceptable salt thereof, and thymidine. In some embodiments, the compound or polymorph is co-administered with thymidine. In some embodiments, the compound or polymorph is administered before, during or after administration of thymidine. Examples of cancer treated include, but is not limited to leukemia, lymphoma, breast cancer, ovarian cancer, lung cancer, pancreatic cancer, hepatocellular carcinoma, melanoma, sarcoma, head and neck cancer, glioma, glioblastoma, and a cancer independent of tissue of origin that are characterized by genomic instability and/or activation of the DNA damage response. Inhibition of dCK by a compound or polymorph detailed herein, or a pharmaceutically acceptable salt thereof, synergizes with thymidine to induce cell cycle arrest in tumors.

In some embodiments, the compounds and polymorphs described herein are used in combination with one another, with other active drugs known to be useful in treating a disease (e.g. anti-cancer agents) or with adjunctive agents that may not be effective alone, but may contribute to the efficacy of the active agent. In some embodiments, the compounds and polymorphs described herein are co-administered with one another or with other active drugs known to be useful in treating a disease.

"Anti-cancer agent" is used in accordance with its plain and ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer.

Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomustine, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene;

adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062 Å, CS-39-L-Ser-.HCl, and RPR-258062 Å), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

When a polymorph of the compound of Formula I is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one polymorph of the compound of Formula I is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the polymorph of the compound of Formula I, such as including, e.g., from about 1 mg to about 1000 mg. The quantity of the at least one polymorph of the compound of Formula I in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one polymorph of the compound of Formula I used and the judgment of the attending clinician taking into consideration factors such as health, weight, and age. In combinational applications in which the at least one polymorph of the compound of Formula I described herein is not the sole active ingredient, it may be possible to administer lesser amounts of the at least one polymorph of the compound of Formula I and still have therapeutic or prophylactic effect.

In some embodiments, the pharmaceutical preparation is in unit dosage form. In such form, the preparation is subdivided into unit doses containing appropriate quantities of the polymorph of the compound of Formula I, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one polymorph of the compound of Formula I. Thereafter, the dosage is increased by small amounts until the optimum effect under the circumstances is reached. For convenience, the total daily dosage may be divided and administered in portions during the day if desired.

The amount and frequency of administration of the at least one polymorph of the compound of Formula I, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one polymorph of the compound of Formula I need not be administered in the same pharmaceutical composition as a chemotherapeutic agent, and may, because of different physical and chemical characteristics, be administered by a different route. For example, the polymorphs/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of polymorph (and where appropriate, chemotherapeutic agent and/or radiation) will depend upon the diagnosis of the attending physicians and their judgment of the condition of the subject and the appropriate treatment protocol.

The one or more polymorphs of the compound of Formula I (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the one or more polymorphs/composition.

In combinational applications and uses, the one or more polymorphs/composition and the chemotherapeutic agent and/or radiation need not be administered simultaneously or essentially simultaneously, and the initial order of administration of the one or more polymorphs/composition, and the chemotherapeutic agent and/or radiation, may not be important. Thus, the at least one polymorph of the compound of Formula I may be administered first followed by the administration of the chemotherapeutic agent and/or radiation; or the chemotherapeutic agent and/or radiation may be administered first followed by the administration of the at least one polymorph of the compound of Formula I. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one polymorph of the compound of Formula I followed, where determined advantageous, by the administration of the chemotherapeutic agent and/or radiation, and so on until the treatment protocol is complete.

Thus, in accordance with experience and knowledge, the practicing physician can modify each protocol for the administration of a polymorph of the compound of Formula I/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a polymorph of the compound of Formula I is administered in a local rather than systemic manner, for example, via injection of the polymorph directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, a polymorph of the compound of Formula I is provided in the form of a rapid release formulation, in the form of an extended release formulation, or in the form of an intermediate release formulation. In yet other embodiments, a polymorph of the compound of Formula I is administered topically.

Kits and Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more polymorphs described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a polymorph of the compound of Formula I formulated in a compatible pharmaceutical carrier are prepared, placed in an appropriate container, and labeled for treatment of an indicated condition.

EXAMPLES

Example 1: Preparation of 2-(1-(2-(4-methoxy-3-(2-morpholinoethoxy)phenyl)-5-methylthiazol-4-yl)ethylthio)pyrimidine-4,6-diamine (6)

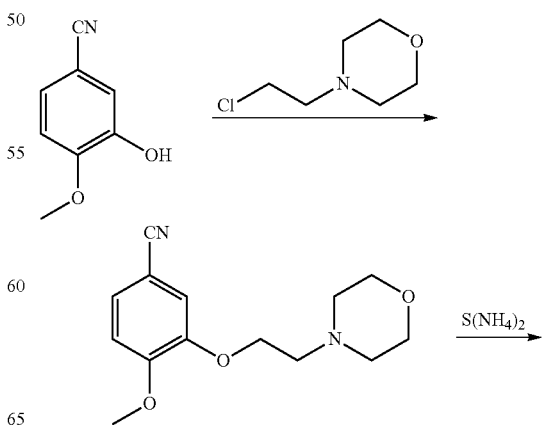

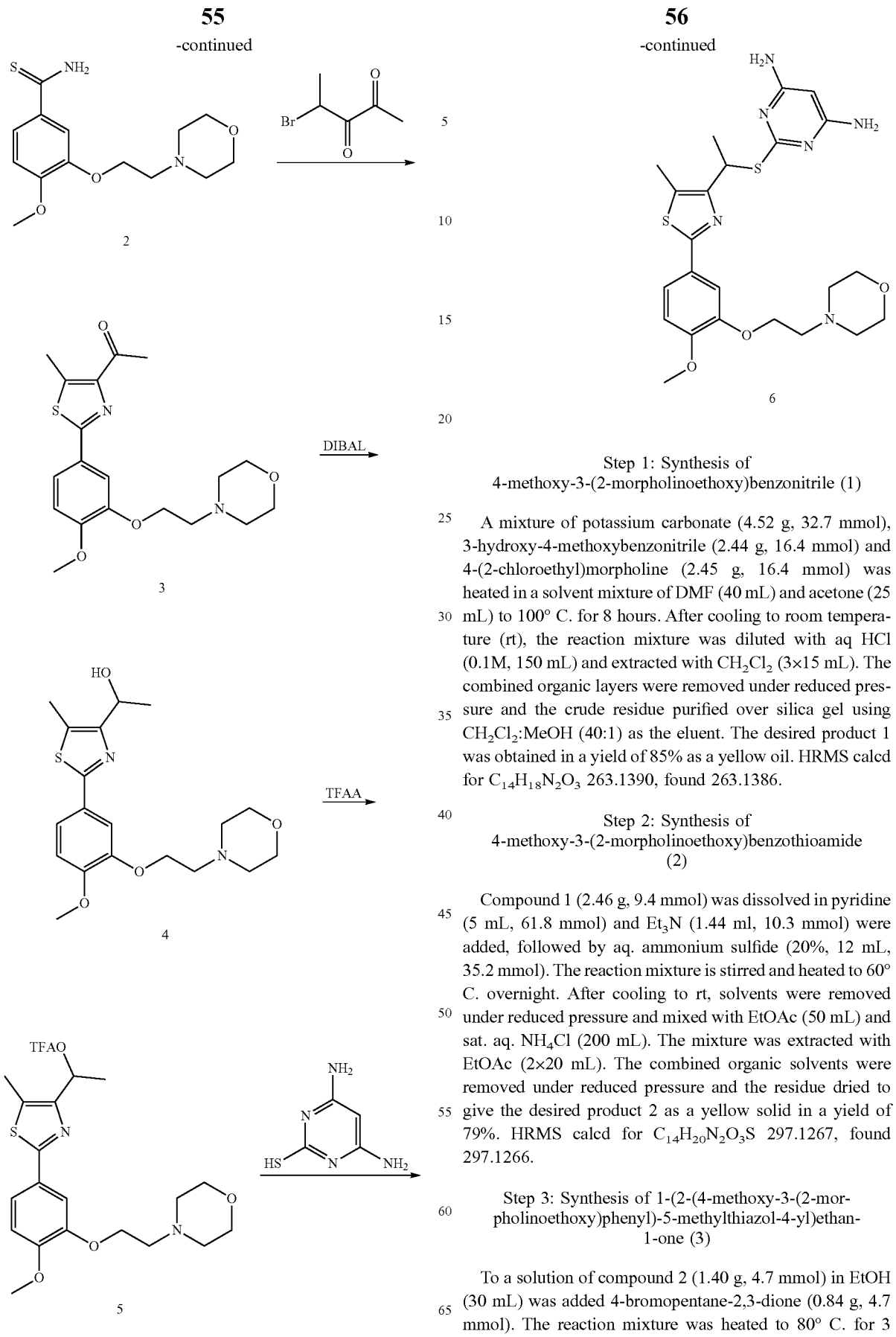

Step 1: Synthesis of 4-methoxy-3-(2-morpholinoethoxy)benzonitrile (1)

A mixture of potassium carbonate (4.52 g, 32.7 mmol), 3-hydroxy-4-methoxybenzonitrile (2.44 g, 16.4 mmol) and 4-(2-chloroethyl)morpholine (2.45 g, 16.4 mmol) was heated in a solvent mixture of DMF (40 mL) and acetone (25 mL) to 100° C. for 8 hours. After cooling to room temperature (rt), the reaction mixture was diluted with aq HCl (0.1M, 150 mL) and extracted with $CH_2Cl_2$ (3×15 mL). The combined organic layers were removed under reduced pressure and the crude residue purified over silica gel using $CH_2Cl_2$:MeOH (40:1) as the eluent. The desired product 1 was obtained in a yield of 85% as a yellow oil. HRMS calcd for $C_{14}H_{18}N_2O_3$ 263.1390, found 263.1386.

Step 2: Synthesis of 4-methoxy-3-(2-morpholinoethoxy)benzothioamide (2)

Compound 1 (2.46 g, 9.4 mmol) was dissolved in pyridine (5 mL, 61.8 mmol) and $Et_3N$ (1.44 ml, 10.3 mmol) were added, followed by aq. ammonium sulfide (20%, 12 mL, 35.2 mmol). The reaction mixture is stirred and heated to 60° C. overnight. After cooling to rt, solvents were removed under reduced pressure and mixed with EtOAc (50 mL) and sat. aq. $NH_4Cl$ (200 mL). The mixture was extracted with EtOAc (2×20 mL). The combined organic solvents were removed under reduced pressure and the residue dried to give the desired product 2 as a yellow solid in a yield of 79%. HRMS calcd for $C_{14}H_{20}N_2O_3S$ 297.1267, found 297.1266.

Step 3: Synthesis of 1-(2-(4-methoxy-3-(2-morpholinoethoxy)phenyl)-5-methylthiazol-4-yl)ethan-1-one (3)

To a solution of compound 2 (1.40 g, 4.7 mmol) in EtOH (30 mL) was added 4-bromopentane-2,3-dione (0.84 g, 4.7 mmol). The reaction mixture was heated to 80° C. for 3 hours. After cooling to rt, the solvents were removed under reduced pressure and the residue mixed with $CH_2Cl_2$ (20 mL) and water (100 mL). The mixture was extracted with $CH_2Cl_2$ (2×10 mL) and the combined organic solvents removed under reduced pressure. The product 3 was obtained as a brown solid without further purification in a yield of 76%. HRMS calcd for $C_{19}H_{24}N_2O_4S$ 377.1530, found 377.1526.

Step 4: Synthesis of 1-(2-(4-methoxy-3-(2-morpholinoethoxy)phenyl)-5-methylthiazol-4-yl)ethan-1-ol (4)

A solution of 3 (1.35 g, 3.6 mmol) in $CH_2Cl_2$ (40 mL) was cooled to −78° C. and DIBAL-H (1M in $CH_2Cl_2$, 14.3 mL, 14.3 mmol) was slowly added. The reaction mixture was allowed to warm to rt and stirred for 30 min. The solution was cooled to 0° C. and add sat. aq. potassium sodium tartrate (10 mL) was added and the mixture was stirred for 1 hour. The solution was extracted with $CH_2Cl_2$ (3×10 mL) and the combined organic solvents were removed under reduced pressure. The crude residue was purified over silica gel using 5-10% MeOH in $CH_2Cl_2$. The pure product 4 was obtained in a yield of 40% as a yellow oil. HRMS calcd for $C_{19}H_{26}N_2O_4S$ 379.1686, found 379.1684.

Step 5: Synthesis of 1-(2-(4-methoxy-3-(2-morpholinoethoxy)phenyl)-5-methylthiazol-4-yl)ethyl 2,2,2-trifluoroacetate (5)

A solution of compound 4 (47 mg, 0.12 mmol) in $CH_2Cl_2$ (5 mL) was cooled to 0° C. and trifluoroacetic anhydride (70 μL, 0.5 mmol) was added dropwise. The reaction mixture was allowed to warm to rt and stirred for 1 hour. The mixture was cooled to 0° C. and ice-cooled water (20 mL) was added. The mixture was extracted with $CH_2Cl_2$ (2×5 mL) and the combined organic layers were removed under reduced pressure to give the desired compound 5 in quantitative yields.

Step 6: Synthesis of 2-((1-(2-(4-methoxy-3-(2-morpholinoethoxy)phenyl)-5-methylthiazol-4-yl)ethyl)thio)pyrimidine-4,6-diamine (6)

To a solution of 4,6-diaminopyrimidine-2-thiol (45 mg, 0.31 mmol) in DMF (1.5 mL) was added potassium carbonate (87 mg, 0.63 mmol), followed by 5 (75 mg, 0.16 mmol). The solution was stirred and heated to 80° C. overnight. After cooling to rt, the reaction mixture was diluted with water (20 mL) and extracted with $CH_2Cl_2$ (3×5 mL). The organic layers were combined and solvents removed under reduced pressure. The crude residue was purified over silica gel using 5-10% MeOH in $CH_2Cl_2$ to give the desired final compound 6 in a yield of 25%. HRMS calcd for $C_{23}H_{30}N_6O_3S_2$ 503.1894, found 503.1876.

Example 2: Preparation of (R)-2-((1-(2-(4-methoxy-3-(2-morpholinoethoxy)phenyl)-5-methylthiazol-4-yl)ethyl)thio)pyrimidine-4,6-diamine (the compound of Formula I)

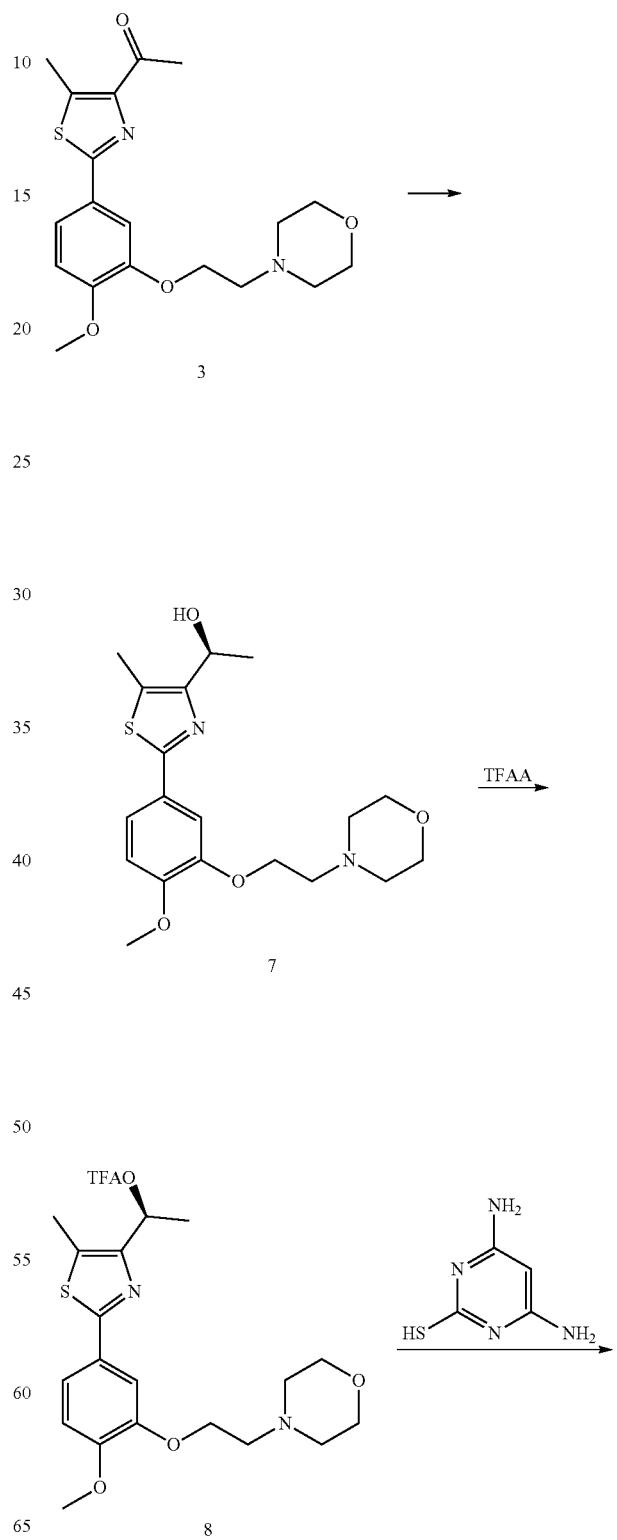

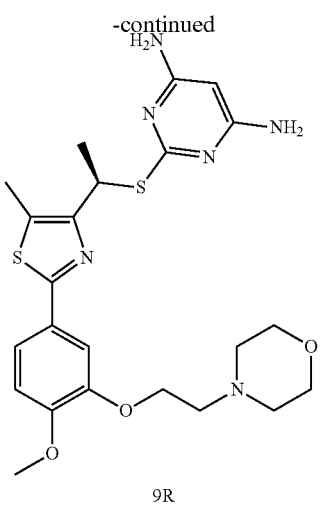

9R

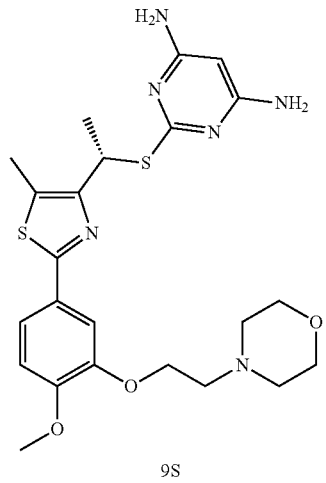 [SMILES: COc1ccc(-c2nc([C@H](C)Sc3nc(N)cc(N)n3)c(C)s2)cc1OCCN1CCOCC1 ; "9S"]

9S

Step 1: Synthesis of (S)-1-(2-(4-methoxy-3-(2-morpholinoethoxy)phenyl)-5-methylthiazol-4-yl)ethanol (7)

To a stirred solution of (R)-(+)-2-Methyl-CBS-oxazaborolidine 1.0 M solution in toluene) in THF at −78° C. under Ar was added borane-tetrahydrofuran complex (1.0 M solution in THF) followed by a solution of 3 in THF. After finish adding the 3 solution with syringe pump for 6 h, the reaction mixture was stirred for another 20 min at −78° C. $H_2O$ and MeOH were added and the mixture was allowed to warm to room temperature. After concentration to remove residual solvent, the resulting residue was washed with brine and extracted with ethyl acetate. The organic layer was washed with water three times, dried over anhydrous $Na_2SO_4$ and concentrated in vacuo, and the crude residue was purified by flash column chromatography over silica gel to yield alcohol 7 as a white solid. HRMS calcd for $C_{19}H_{26}N_2O_4S$ 379.1686, found 379.1684.

Step 2: Synthesis of (S)-1-(2-(4-methoxy-3-(2-morpholinoethoxy)phenyl)-5-methylthiazol-4-yl)ethyl 2,2,2-trifluoroacetate (8)

A solution of compound 7 (47 mg, 0.12 mmol) in $CH_2Cl_2$ (5 mL) was cooled to 0° C. and trifluoroacetic anhydride (70 μL, 0.5 mmol) was added dropwise. The reaction mixture was allowed to warm to rt and stirred for 1 hour. The mixture was cooled to 0° C. and ice-cooled water (20 mL) was added. The mixture was extracted with $CH_2Cl_2$ (2×5 mL) and the combined organic layers were removed under reduced pressure to give the desired compound 8 in quantitative yields.

Step 3: Synthesis of (R)-2-(1-(2-(4-methoxy-3-(2-morpholinoethoxy)phenyl)-5-methylthiazol-4-yl)ethylthio)pyrimidine-4,6-diamine (9R) and (S)-2-(1-(2-(4-methoxy-3-(2-morpholinoethoxy)phenyl)-5-methylthiazol-4-yl)ethylthio)pyrimidine-4,6-diamine (9S)

To a solution of 4,6-diaminopyrimidine-2-thiol (45 mg, 0.31 mmol) in DMF (1.5 mL) was added potassium carbonate (87 mg, 0.63 mmol), followed by 8 (75 mg, 0.16 mmol). The solution was stirred and heated to 80° C. overnight. After cooling to rt, the reaction mixture was diluted with water (20 mL) and extracted with $CH_2Cl_2$ (3×5 mL). The organic layers were combined and solvents removed under reduced pressure. The crude residue was purified over silica gel using 5-10% MeOH in $CH_2Cl_2$ to afford the couple of enantiomers 9R and 9S as a white solid. Recrystallization of the enantiomers with MeOH/acetone solvent system gave 9R with 93% ee. HRMS calcd for $C_{23}H_{30}N_6O_3S_2$ 503.1894, found 503.1876.

Example 3: Preparation of Polymorph Form I of the Compound of Formula I

Maleic acid (66.05 g, 1.0 equiv) was dissolved with stirring in ethanol (300 mL) at 40° C. In a separate container, (R)-2-(1-(2-(4-methoxy-3-(2-morpholinoethoxy)phenyl)-5-methylthiazol-4-yl)ethylthio)pyrimidine-4,6-diamine (314.95 g, 1.0 equiv) was dissolved with stirring in ethanol (850 mL) and ethyl acetate (1.15 L) and stirred for 1 hour at 60° C. The maleic acid solution was slowly added and the resulting reaction mixture was stirred for 20 hours at 60° C. The reaction mixture was cooled to room temperature, diluted with ethyl acetate (5.8 L), and stirred for 30 minutes at room temperature. The reaction mixture was cooled to 0° C., stirred at 0° C. for 3 hours, and filtered. The filter cake was dried at 55° C. for 64 hours to yield polymorph Form I of the compound of Formula I (317.94 g, 82.0% yield, 97.6% purity).

Example 4: Preparation of Polymorph Form II of the Compound of Formula I

Polymorph Form I of the compound of Formula I (323.15 g) was dissolved with stirring in 1:1 DCM/methanol (2.4 L) at 45° C. The reaction mixture was cooled to 5° C. over the course of 1 hour and stirred at 5° C. for 16 hours. The reaction mixture was diluted with methyl tert-butyl ether (2.4 L) over 2 hours, stirred at 5° C. for 2 hours, and filtered. The filter cake was washed with methyl tert-butyl ether (700 mL) and dried at 70° C. for 47 hours to yield polymorph Form I of the compound of Formula I (295.41 g, 98.4% purity).

Example 5: X-Ray Powder Diffraction (XRPD)

X-ray powder diffraction (XRPD) patterns were obtained on a Rigaku Miniflex. A CuK source (=1.54056 angstrom) operating minimally at 40 kV and 15 mA scans each sample between 3 and 45 degrees 2-θ. The step size is 0.02 degrees 2-theta and the scan speed is 2.5 degrees per minute.

The XRPD pattern obtained for polymorph Form I of the compound of Formula I is summarized in Table 1 and FIG. 2.

TABLE 1

| Peak # | Angle (°2-θ) | Intensity (%) |
|---|---|---|
| 1 | 3.207 | 8.4 |
| 2 | 8.224 | 100.0 |
| 3 | 9.864 | 10.9 |
| 4 | 12.661 | 42.2 |
| 5 | 15.355 | 3.5 |
| 6 | 16.419 | 24.9 |
| 7 | 16.917 | 24.3 |
| 8 | 17.570 | 25.0 |
| 9 | 18.927 | 8.0 |
| 10 | 19.189 | 3.7 |
| 11 | 19.884 | 20.9 |
| 12 | 20.557 | 26.3 |
| 13 | 21.196 | 21.3 |
| 14 | 22.080 | 8.2 |
| 15 | 22.911 | 36.4 |
| 16 | 23.403 | 25.9 |
| 17 | 23.909 | 26.0 |
| 18 | 24.219 | 16.6 |
| 19 | 24.908 | 29.1 |
| 20 | 25.408 | 18.4 |
| 21 | 26.379 | 9.2 |
| 22 | 27.090 | 20.1 |
| 23 | 28.154 | 3.0 |
| 24 | 28.868 | 8.2 |
| 25 | 29.190 | 12.7 |
| 26 | 29.876 | 11.5 |
| 27 | 30.930 | 6.5 |
| 28 | 31.516 | 4.1 |
| 29 | 32.303 | 5.9 |
| 30 | 34.759 | 2.9 |
| 31 | 35.706 | 6.4 |

The XRPD pattern obtained for polymorph Form II of the compound of Formula I is summarized in Table 2 and FIG. 5.

TABLE 2

| Peak # | Angle (°2-θ) | Intensity (%) |
|---|---|---|
| 1 | 7.618 | 100.0 |
| 2 | 8.042 | 16.6 |
| 3 | 8.663 | 87.2 |
| 4 | 10.763 | 16.2 |
| 5 | 12.207 | 24.1 |
| 6 | 13.444 | 13.1 |
| 7 | 13.738 | 3.7 |
| 8 | 15.295 | 6.1 |
| 9 | 15.991 | 76.0 |
| 10 | 16.420 | 5.1 |
| 11 | 17.304 | 4.5 |
| 12 | 17.564 | 27.9 |
| 13 | 19.540 | 12.2 |
| 14 | 21.657 | 11.4 |
| 15 | 21.893 | 3.8 |
| 16 | 22.859 | 8.0 |
| 17 | 23.248 | 4.2 |
| 18 | 23.757 | 2.9 |
| 19 | 24.246 | 9.8 |
| 20 | 24.685 | 6.3 |
| 21 | 26.199 | 4.5 |
| 22 | 28.092 | 3.3 |
| 23 | 28.895 | 2.0 |
| 24 | 29.192 | 3.0 |
| 25 | 29.996 | 2.0 |
| 26 | 30.820 | 4.2 |
| 27 | 31.568 | 1.6 |
| 28 | 38.738 | 3.6 |

Example 6: Thermogravimetric Analysis (TGA)

Thermogravimetric analysis was carried out on a TA Instruments Q5000 thermogravimetric analyzer. Samples were heated in aluminum pans from ambient to 250° C. at 15° C./min with a nitrogen purge of 60 mL/min. The TGA thermogram obtained for polymorph Form I of the compound of Formula I is summarized in FIG. 3. The TGA thermogram obtained for polymorph Form II of the compound of Formula I is summarized in FIG. 6.

Example 7: Differential Scanning Calorimetry (DSC)

Differential scanning calorimetry analysis was carried out on a TA Instruments Discovery thermogravimetric analyzer. Samples were heated in sealed aluminum pans from ambient to 250° C. at 10° C./min. The DSC thermogram obtained for polymorph Form I of the compound of Formula I is summarized in FIG. 1. The DSC thermogram obtained for polymorph Form II of the compound of Formula I is summarized in FIG. 4.

Example 8: High-Performance Liquid Chromatography (HPLC)

High-performance liquid chromatography (HPLC) was performed using the following instrument and/or conditions.

| | |
|---|---|
| HPLC System | Waters Alliance HPLC equipped with UV Detector |
| Column | Waters XBridge BEH C18, 4.6 × 250 mm, 5.0 μm, Part Number 186003117 (Column # 1385) |
| Column Temperature | 30.0 ± 5.0° C. |
| Sample Temperature | Ambient |
| Diluent | [80:10:10] ACN:DCM:Water |
| Mobile Phase A | 0.1% NH$_4$OH in Water |
| Mobile Phase B/Needle Wash | 100% ACN |
| Needle Wash | Extended |
| Injection Volume | 10 μL |
| Run Time | 35 minutes |
| Detection Wavelength | 290 nm |
| Sample Rate | 2 pt/sec |
| Flow | 1.0 mL/min |

| | Time (Minutes) | Mobile Phase A (%) | Mobile Phase B (%) |
|---|---|---|---|
| Gradient | 0.0 | 95.0 | 5.0 |
| | 25.0 | 30.0 | 70.0 |
| | 27.0 | 5.0 | 95.0 |
| | 29.0 | 5.0 | 95.0 |
| | 30.0 | 95.0 | 5.0 |
| | 35.0 | 95.0 | 5.0 |

Example 9: Stability Tests of Polymorph Form II

The results of polymorph Form II in accelerated stability tests are shown in Table 3.

| Exposure | Purity (area %) | Potency (%) |
|---|---|---|
| API standard | 98.22 | 98.6 |
| 25° C./60% RH for 1 week | 98.75 | 98.7 |
| 40° C./75% RH for 1 week | 98.66 | 98.6 |
| 60° C. for 1 week | 98.75 | 98.6 |

Example 10: Efficacy of Compound 1 in a Mouse Model of Myelin Oligodendrocyte Glycoprotein (MOG)-Induced Experimental Autoimmune Encephalomyelitis (EAE)

Adult female C57BL/6J mice were randomly allocated to experimental groups and allowed to acclimatize for one week prior to commencing the study. On Day 0 and Day 7, animals were administered an emulsion (200 µL/mouse) of MOG35-55 and complete Freund's adjuvant (CFA). MOG35-55 (300 µg/mouse) was purchased as powder and reconstituted with NaCl (0.9%) at an initial concentration of 3 mg/mL. After reconstitution, the MOG35-55 solution was mixed with an equivalent volume of CFA prepared by reconstituting *Mycobacterium Tuberculosis* H37Ra in Incomplete Freund's adjuvant at an initial concentration of 5 mg/mL in order to obtain a final concentration of 2.5 mg/mL. Injections were performed under gas (isoflurane) anesthesia in the two lower quadrants of the back on Day 0 (100 µL in each flank) and the two upper quadrants of the back on Day 7 (100 µL in each flank). On Day 0 (immediately post-MOG injection) and Day 2, animals were administered with pertussis toxin (PTx, 500 ng/mouse) prepared in phosphate buffered saline (PBS, 100 µL/mouse) by intraperitoneal injection.

Treatments were administered according to the administration schedule shown in Table 4.

| | Treatments | | | |
|---|---|---|---|---|
| Groups | Dose | Route | Regimen | Intervention |
| (1) Vehicle (40% Captisol) | at 5 mL/kg | P.O. | BID, Days 1-25 | Day 0: $MOG_{35-55}$ S.C. |
| (2) Compound 1 | 75 mg/kg | P.O. | BID, Days 1-25 | Day 0: PTx I.P. |
| (3) Vehicle/Compound 1 | (150 mg/kg/day) (at 5 mL/kg) | P.O. | BID, Vehicle: Days 1-7 Compound 1: Days 8-25 | Day 2: PTx I.P. Day 7: $MOG_{35-55}$ S.C. |
| (4) Dexamethasone | 1 mg/kg (at 5 mL/kg) | S.C. P.O. | SC in the morning PO - vehicle in the evening Days 1-25 | |

Treatment was performed twice daily (BID) prophylactically starting on Day 1 for groups 1, 2, and 4, and therapeutically starting on day 8 for group 3. All experimental groups were n=12. The administration interval was 12 hours and the administration volume was 5 mL/kg.

Figure 7:
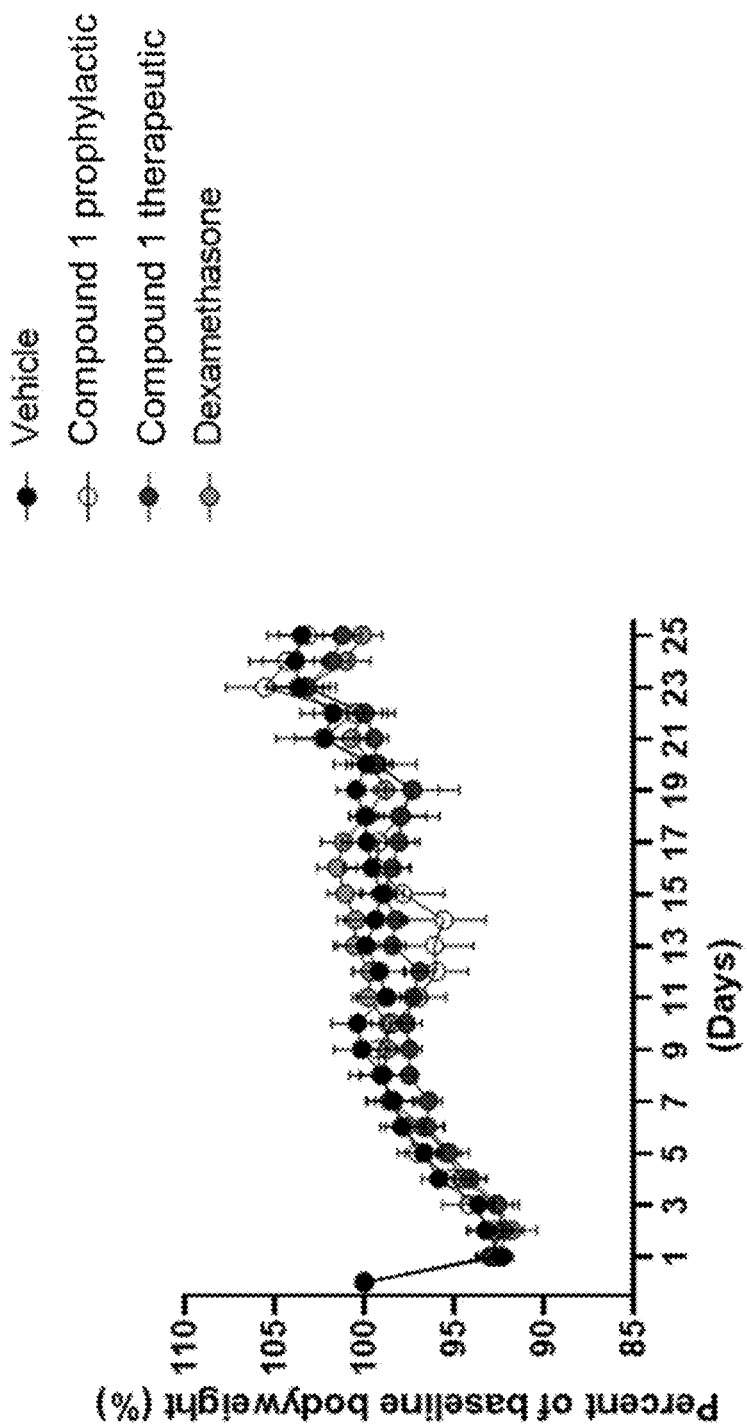
FIG. 7 shows the changes in mouse body weight observed for the different experimental groups over the course of the mouse model of myelin oligodendrocyte glycoprotein (MOG)-induced experimental autoimmune encephalomyelitis (EAE) experiment.

Because body weight loss is known to be an important hallmark of EAE occurring in correspondence of the appearance of the first symptoms, animals were weighed daily from the day of immunization (Day 0) until the end of the experiment. The changes in body weight observed over the course of the experiment for the different experimental groups, presented as mean±SEM, are summarized in FIG. 7. As expected, a significant weight loss was observed in a time-dependent manner in vehicle-treated animals (p<0.001). A marked bodyweight loss was observed immediately after the first $MOG_{35-55}$ administration, after which time the body weight gradually returned to normal. A similar effect on body weights was observed in Compound 1- and dexamethasone-treated groups. Analyzing the two variables as dependent from each other (time×treatment effect) revealed a significant general effect (p=0.002) suggesting the bodyweights increase over time in a similar manner among all the experimental groups.

Figure 8:
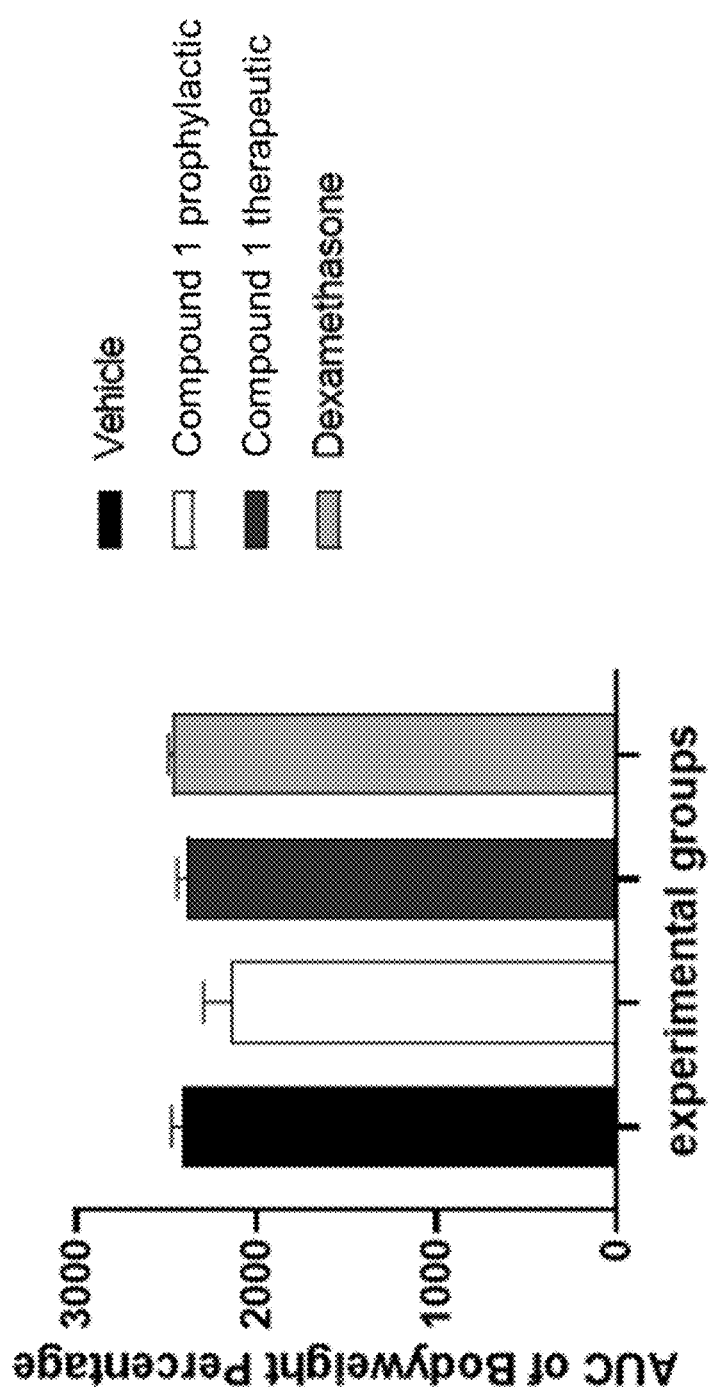
FIG. 8 shows the area under the curve values of the percentage of bodyweight changes in comparison to baseline observed for the different experimental groups in the mouse model of myelin oligodendrocyte glycoprotein (MOG)-induced experimental autoimmune encephalomyelitis (EAE) experiment.

Next, in order to assess the overall effect of the pharmacological treatment, analysis of the area under the curve (AUC) was performed. The area under the curve values of the percentage of bodyweight changes in comparison to baseline for the different experimental groups, presented as mean±SEM, are summarized in FIG. 8. AUC analysis corroborated the body weight loss data and showed no significant differences between the groups treated with Compound 1 and the vehicle-treated group. Prophylactic treatment with Compound 1 showed a small trend towards a reduced AUC value which indicates a greater bodyweight loss in this group in comparison to the vehicle. However, it failed to reach the significance threshold (p=0.72).

From Day 0 until the end of the experiment, animals were scored daily for clinical signs of EAE to include paresis and paralysis affecting the tail and the limbs. The following scale was used:
(0) no abnormality, the animal moves and behaves normally;
(1) limp tail, the tail hangs limp when the mouse is held at the base of the tail;
(2) partial hind limb paralysis, spastic paresis or paralysis affects one hind limb;
(3) total hind limb paralysis, spastic paresis or paralysis affects both hind limbs;
(4) front and hind limb paralysis, spastic paresis or paralysis affects one or both front limbs;
(5) moribund.

Figure 9:
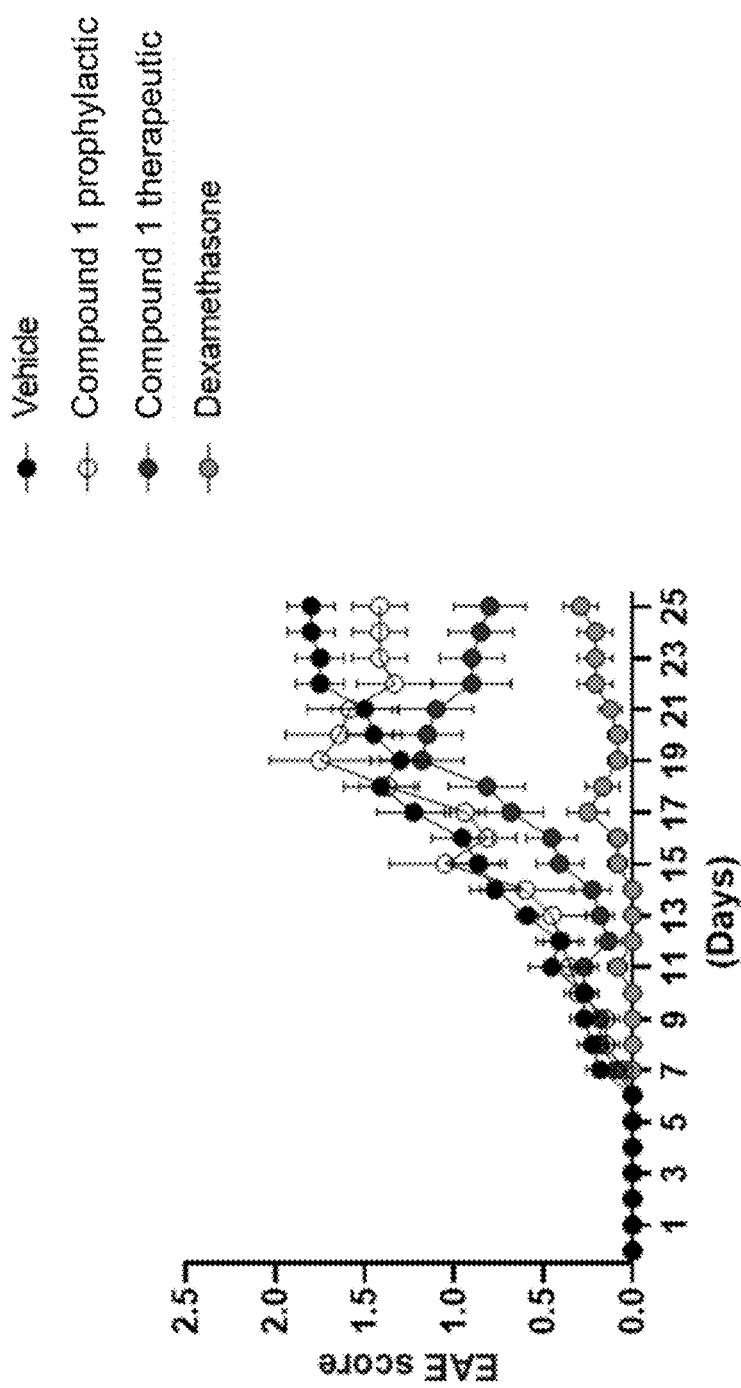
FIG. 9 shows the changes in EAE score observed for the different experimental groups over the course of the mouse model of myelin oligodendrocyte glycoprotein (MOG)-induced experimental autoimmune encephalomyelitis (EAE) experiment.

The changes in EAE score observed over the course of the experiment for the different experimental groups, presented as mean±SEM, are summarized in FIG. 9. Analysis of the clinical EAE profile revealed that the first clinical symptoms appeared at day 7 after immunization in almost all the experimental groups. On day 8, treatments with Compound 1 started for group 3 which was administered with vehicle until that day. The vehicle-treated group showed a constantly increasing disease profile over time (p<0.0001). A similar disease course was observed for the group treated prophylactically with Compound 1. On the contrary, both the administration of Compound 1 following a therapeutic approach and the prophylactic administration of Dexamethasone, as positive control, significantly ameliorated the disease profile (p<0.0001).

Figure 10:
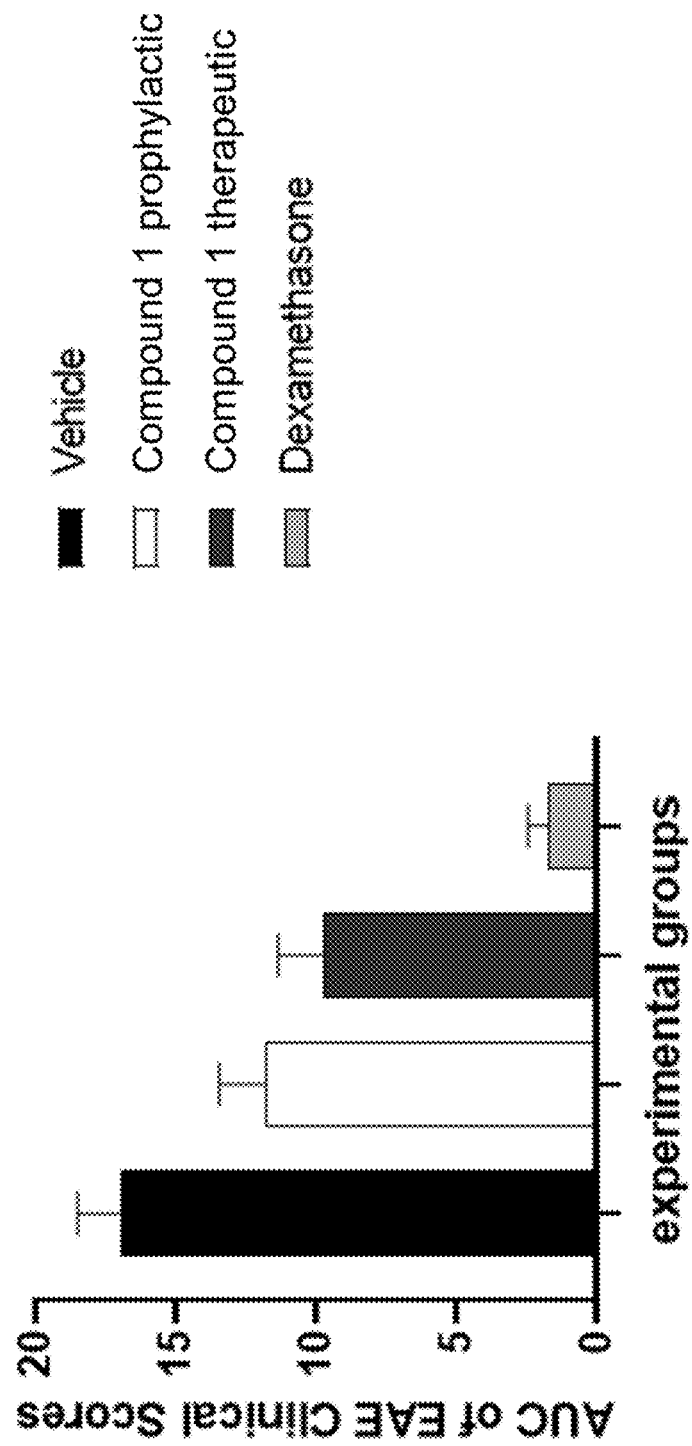
FIG. 10 shows the area under the curve values of the EAE clinical scores observed for the different experimental groups in the mouse model of myelin oligodendrocyte glycoprotein (MOG)-induced experimental autoimmune encephalomyelitis (EAE) experiment.

Next, in order to assess the overall effect of the pharmacological treatment, analysis of the AUC was performed. The area under the curve values of the EAE clinical scores for the different experimental groups, presented as mean±SEM, are summarized in FIG. 10. AUC analysis corroborated the changes in the disease profile observed over time. The therapeutic treatment with Compound 1 reduced the calculated AUC indicating amelioration of the symptoms. However, despite showing a clear tendency, it did not reach significant threshold. A trend towards a reduced AUC value was also observed in the Compound 1 prophylactic group. Treatments with dexamethasone significantly lowered the curve, therefore reducing the calculated AUC indicating amelioration of the symptoms (vehicle vs. dexamethasone: p<0.0001).

Figure 11:
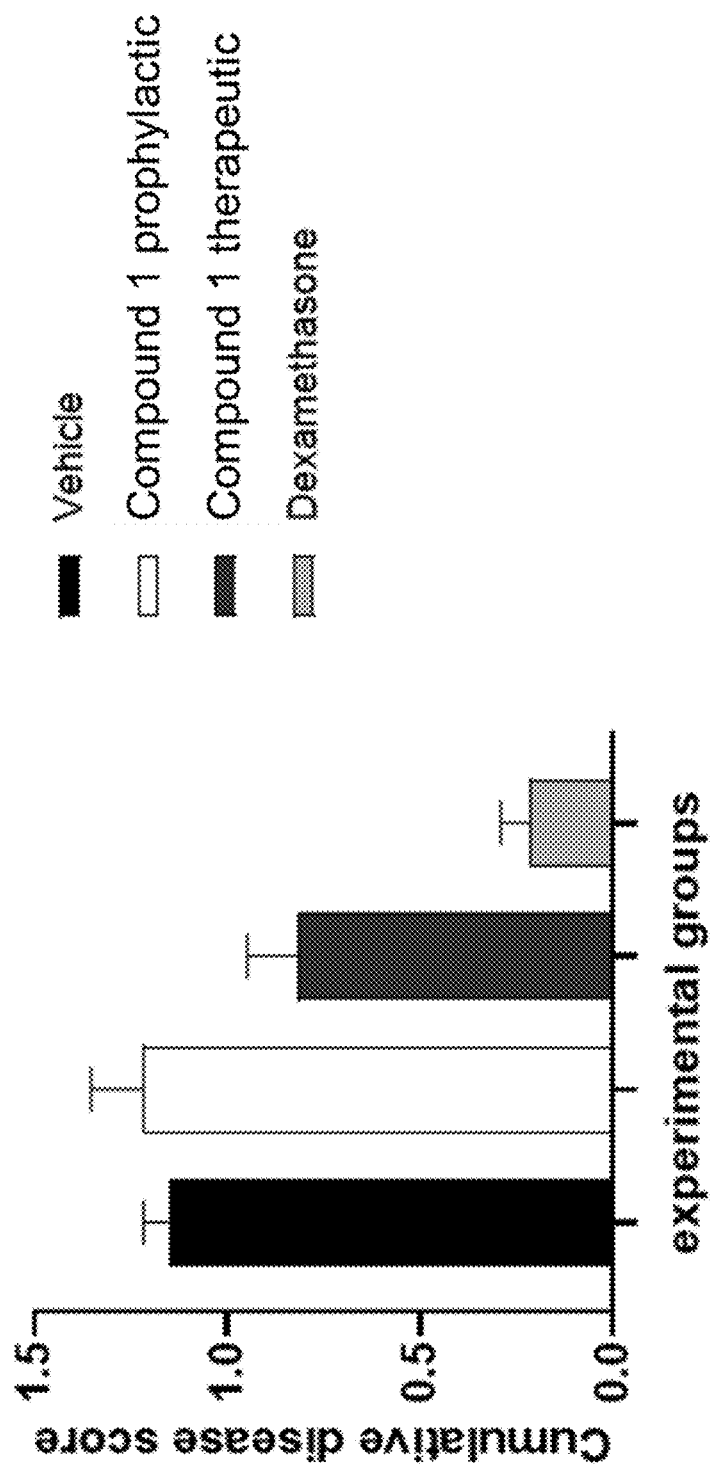
FIG. 11 shows the cumulative disease scores observed for the different experimental groups in the mouse model of myelin oligodendrocyte glycoprotein (MOG)-induced experimental autoimmune encephalomyelitis (EAE) experiment.

The overall effect of the treatment was analyzed by calculating a mean cumulative score obtained for every animal in every experimental group summing up the disease scores from the day in which the first symptom appeared until Day 25 and dividing this value by the number of days in which the animal displayed clinical scores. The cumulative disease scores for the different experimental groups, presented as mean±standard error of the mean (SEM), are summarized in FIG. 11. Kruskal-Wallis test (Kruskal-Wallis statistics: 24.74) revealed an overall significant effect of the treatment but Dunn's multiple comparisons test identified only a significant difference for the dexamethasone-treated group (p<0.0001 vs. vehicle).

Figure 12:
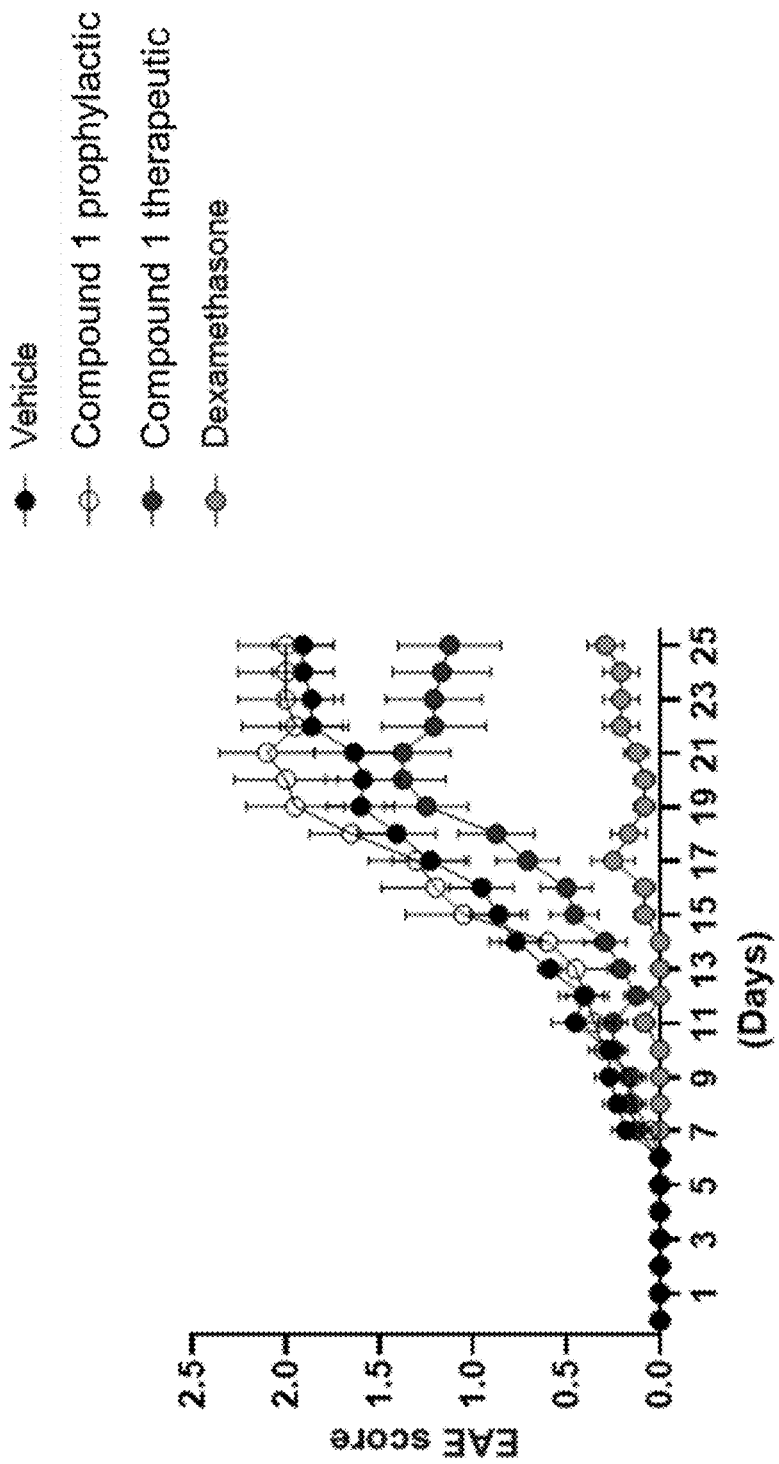
FIG. 12 shows a disease profile course resulting from all the animals showing a disease score until Day 25 for the different experimental groups in the mouse model of myelin oligodendrocyte glycoprotein (MOG)-induced experimental autoimmune encephalomyelitis (EAE) experiment.

An additional parameter considered for EAE analysis is plotting and analyzing "extended data". While the graph shown in FIG. 9 includes the disease scores of animals terminated prior to the scheduled end until the day of their respective termination (e.g. if an animal was terminated on Day 20, that following time point in the graph, will contain less animals), the graph presented in FIG. 12 shows a disease profile course resulting from all the animals showing a disease score until Day 25 (e.g. the animals that were terminated earlier maintain the score they had at termination day until day 25). This is a common method to represent the EAE disease profile that can be used to assess a group effect.

In a similar scenario to the one described above for FIG. 9, the vehicle-treated group showed a constantly increasing disease profile over time (p<0.0001). A similar disease course was observed for the group treated prophylactically with Compound 1. On the contrary, both the administration of Compound 1 following a therapeutic approach and the prophylactic administration of Dexamethasone, as a positive control, significantly ameliorated the disease profile (p<0.0001).

Figure 13:
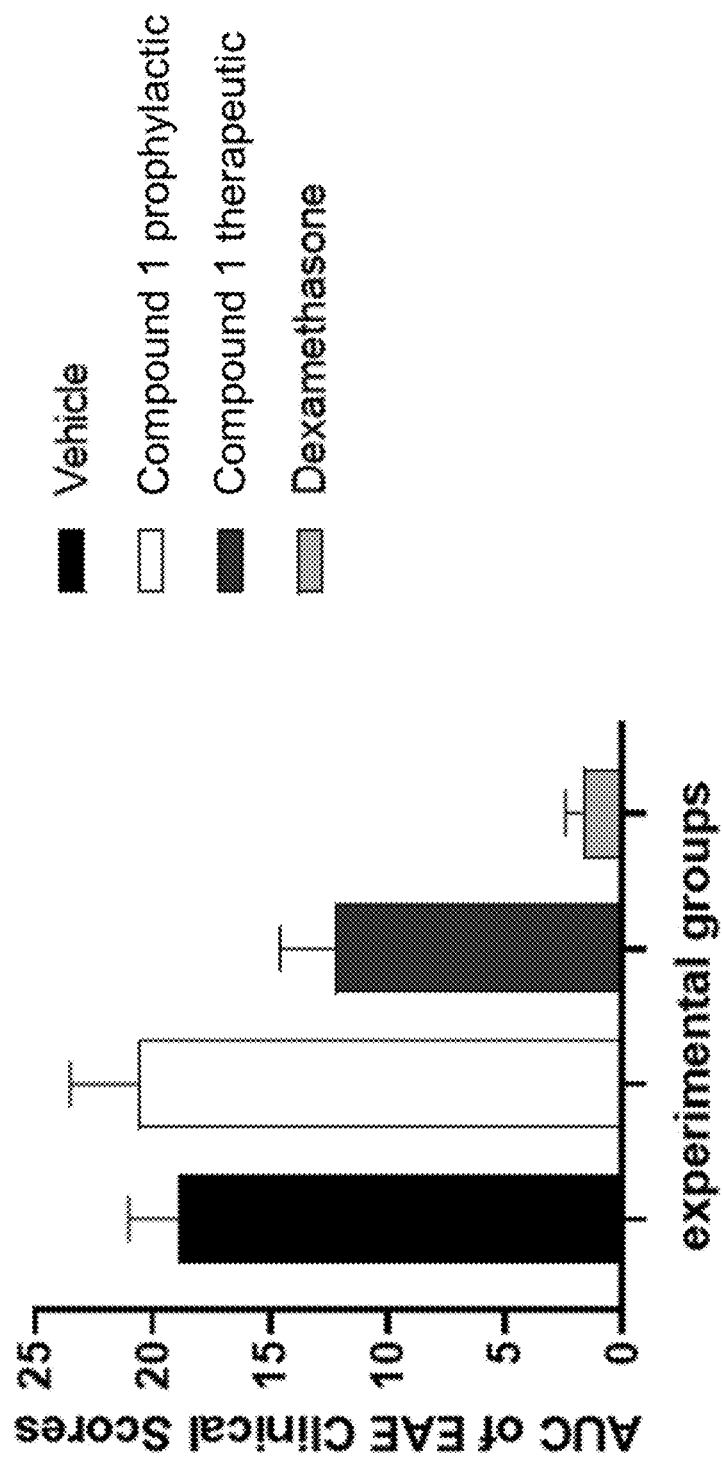
FIG. 13 shows the area under the curve values of the extended disease scores observed for the different experimental groups in the mouse model of myelin oligodendrocyte glycoprotein (MOG)-induced experimental autoimmune encephalomyelitis (EAE) experiment.

Next, in order to assess the overall effect of the pharmacological treatment, analysis of the AUC was performed on the extended disease score. The area under the curve values of the extended disease scores for the different experimental groups, presented as mean±SEM, are summarized in FIG. 13. AUC analysis corroborated the changes in the disease profile observed over time. The therapeutic treatment with Compound 1 reduced the calculated AUC indicating amelioration of the symptoms. However, despite showing a clear tendency, it did not reach significant threshold. Treatments with dexamethasone significantly lowered the curve, therefore reducing the calculated AUC indicating amelioration of the symptoms (vehicle vs. dexamethasone: p<0.0001).

Analysis of the incidence in the vehicle-treated group and in the groups treated therapeutically and prophylactically with Compound 1, considered as the percentage of symptoms free animals at any of the analyzed time points, revealed that a higher percentage of animals did not show disease symptoms in the group which received Compound 1 therapeutically in comparison to the respective vehicle-treated group at any of the analyzed time points (FIG. 14, upper panel). Moreover, while the therapeutically treated group never reached 100% incidence (~92% on Day 19), the vehicle-treated group did reach 100% incidence on Day 13. Animals therapeutically treated with Compound 1 do not only show a significant remission reflected by the amelioration of symptoms after Day 20 (FIGS. 9 and 12) but, ~27% of the animals showed no symptoms at all suggesting a complete remission in these animals after Day 20 (FIG. 14, upper panel). No differences in the percentage of symptoms free animals were observed for the group treated prophylactically with Compound 1 (FIG. 14, lower panel) even if, the animas left in the group do show an amelioration of symptoms in comparison to vehicle-treated ones (FIGS. 9 and 12).

Figure 15:
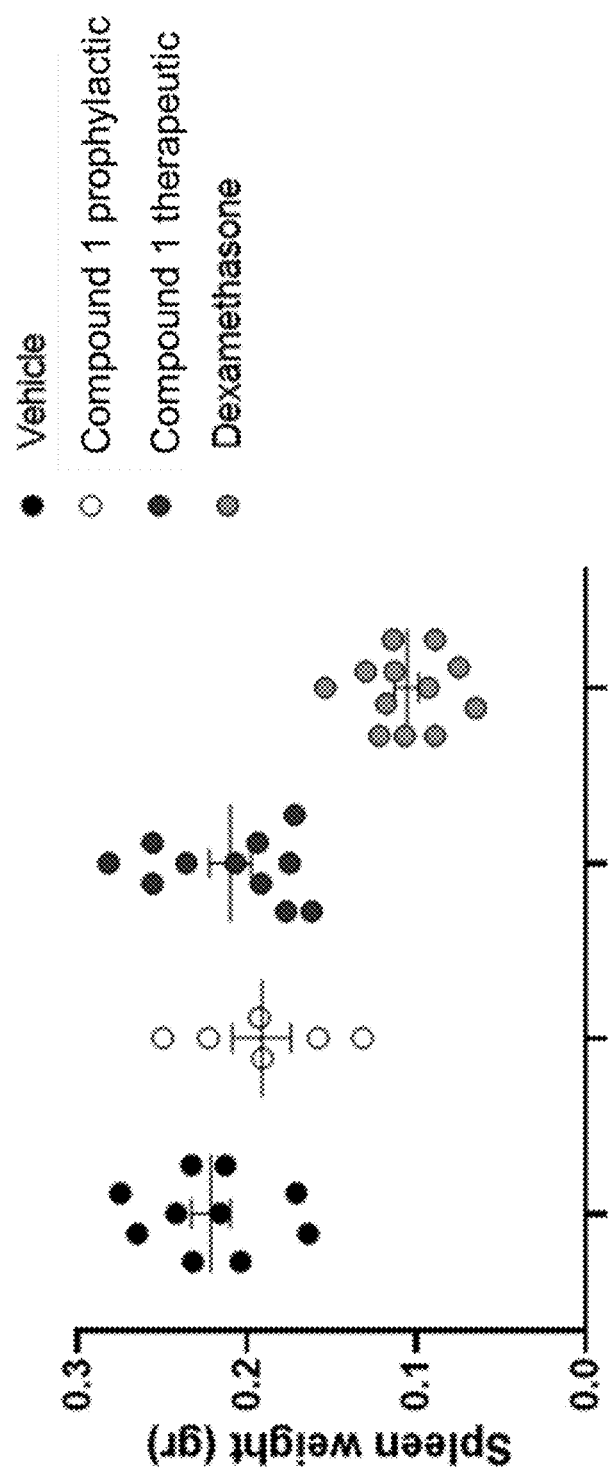
FIG. 15 shows the spleen weights observed for the different experimental groups in the mouse model of myelin oligodendrocyte glycoprotein (MOG)-induced experimental autoimmune encephalomyelitis (EAE) experiment.

At termination, spleens were removed and weighed. The spleen weights observed for the different experimental groups, presented as mean±SEM, are summarized in FIG. 15. No differences were observed between the spleen size recorded for the vehicle-treated group and both groups treated with Compound 1. Animals treated with dexamethasone show significantly lower spleen weights in comparison to the vehicle-treated group.

Analysis of plasma cytokine levels using Luminex showed low levels of all cytokines measured (IFN-$\gamma$, IL-6, IL-10, IL-17a, and TNF-$\alpha$), with most samples reporting values close to or below the functional Lower Limit Of Quantification (LLOQ) for each cytokine assay (FIGS. 16-20).

Figure 16:
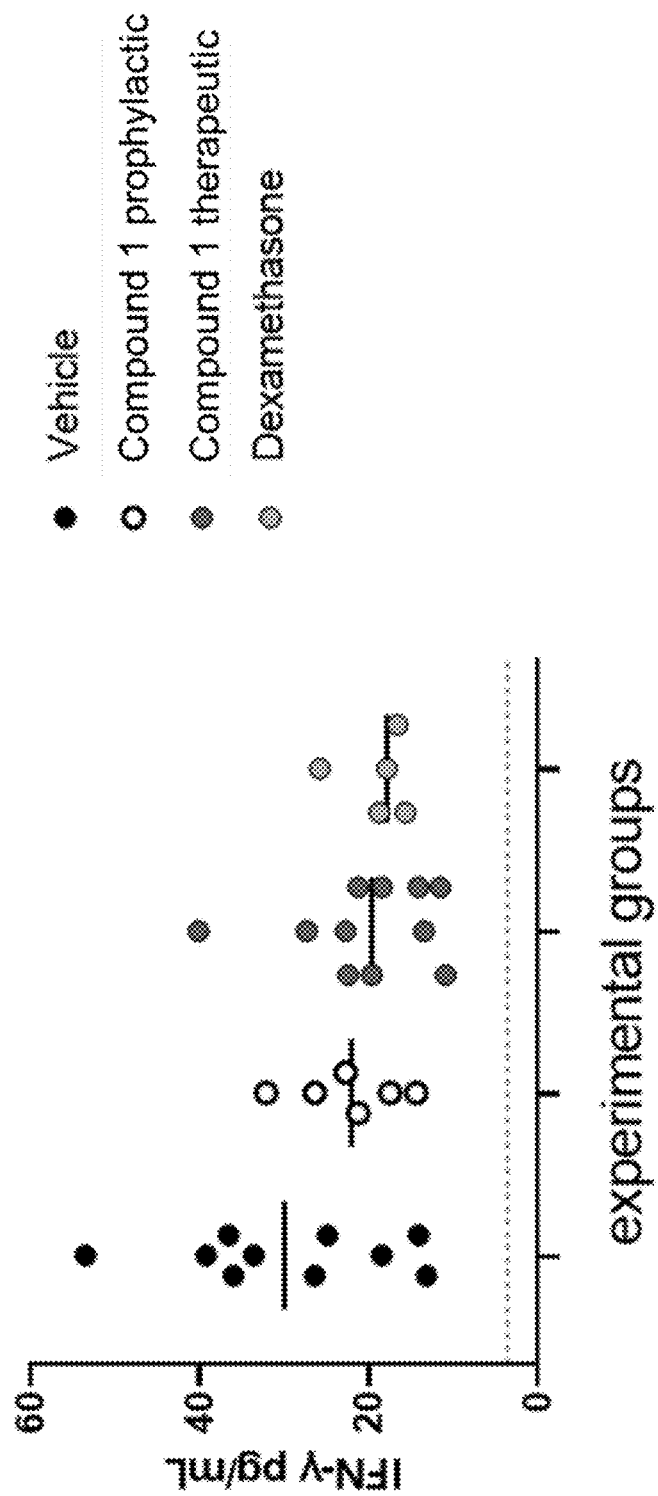
FIG. 16 shows the IFN-γ levels observed for the different experimental groups in the mouse model of myelin oligodendrocyte glycoprotein (MOG)-induced experimental autoimmune encephalomyelitis (EAE) experiment.

The IFN-$\gamma$ levels observed for the different experimental groups, presented as mean±SEM, are summarized in FIG. 16. Overall, no statistically significant changes were observed for IFN-$\gamma$ (p=0.096) although there was a decreasing trend from vehicle to dexamethasone, thus mirroring the in vivo clinical score data. A decrease in IFN-$\gamma$ was observed for both prophylactic and therapeutic Compound 1 treatments, with the therapeutic treatment almost matching that of the dexamethasone group.

Figure 17:
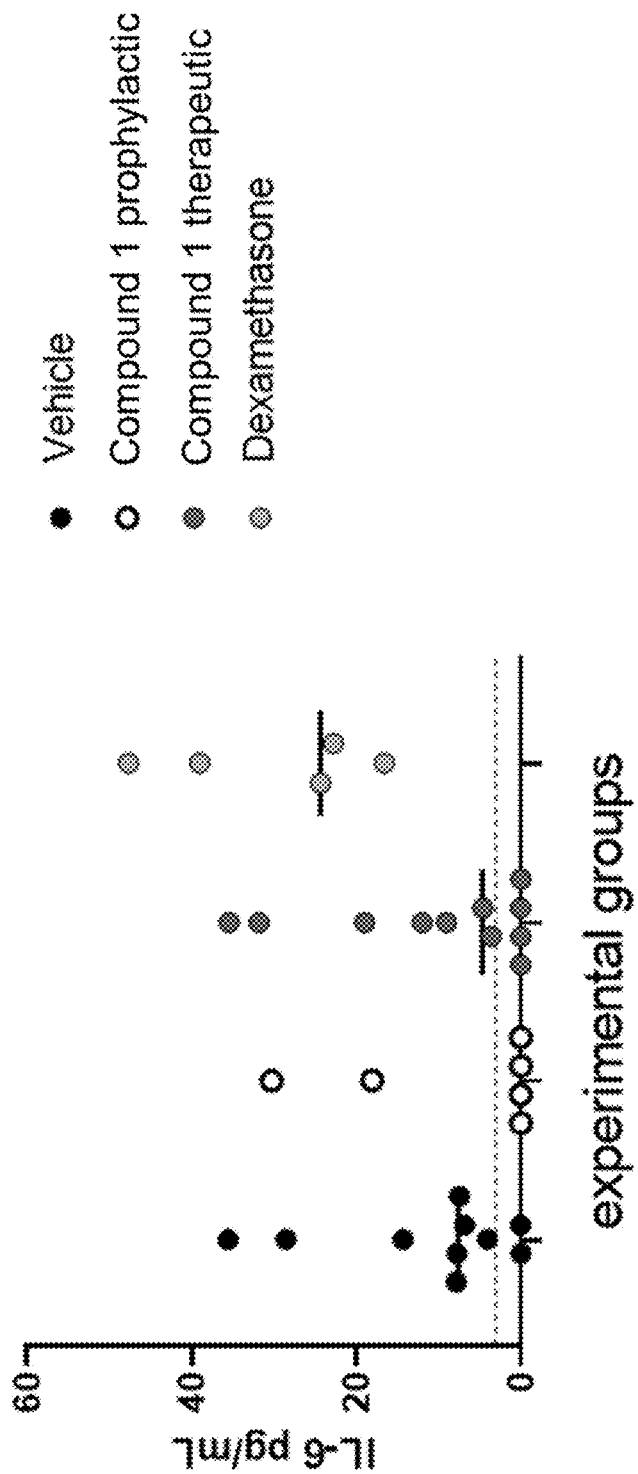
FIG. 17 shows the Interleukin 6 (IL-6) levels observed for the different experimental groups in the mouse model of myelin oligodendrocyte glycoprotein (MOG)-induced experimental autoimmune encephalomyelitis (EAE) experiment.

The Interleukin 6 (IL-6) levels observed for the different experimental groups, presented as mean±SEM, are summarized in FIG. 17. IL-6 was present at low levels or levels below the limit of detection in plasma from all samples and no significant differences were observed between groups.

Figure 18:
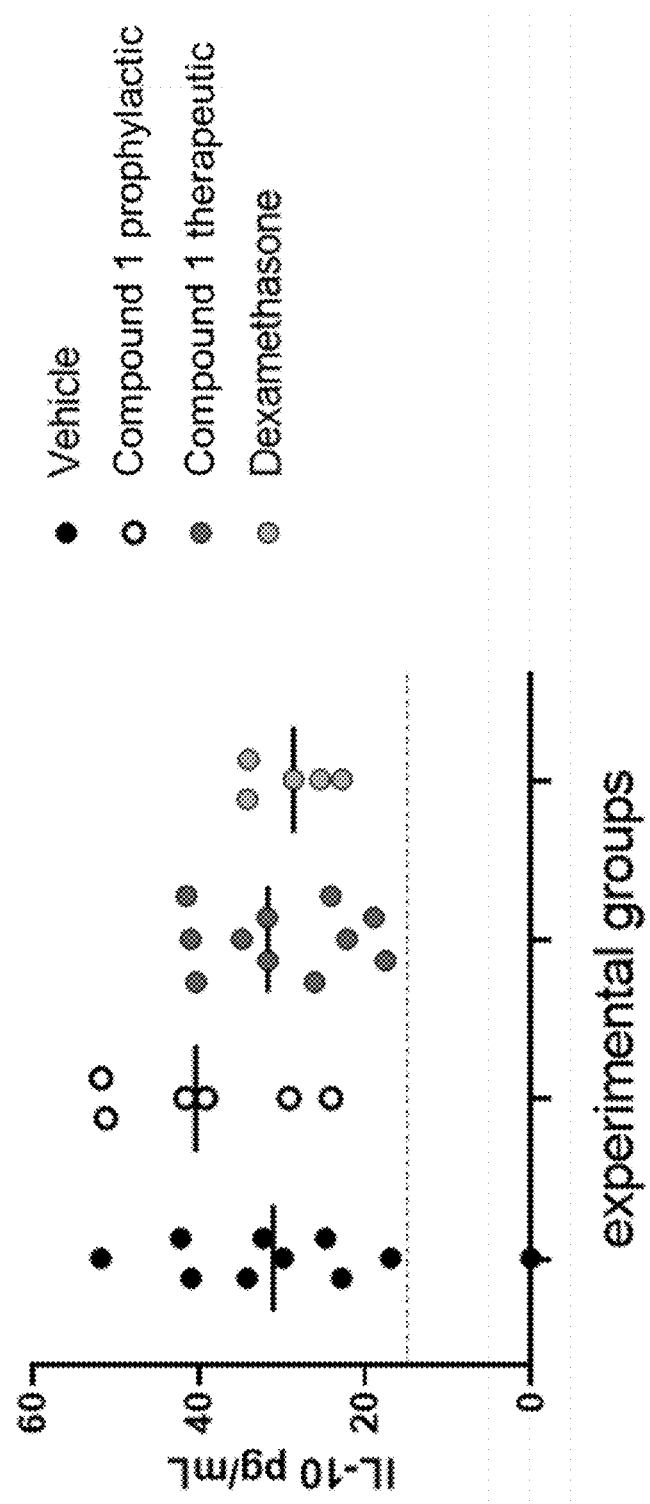
FIG. 18 shows the Interleukin 10 (IL-10) levels observed for the different experimental groups in the mouse model of myelin oligodendrocyte glycoprotein (MOG)-induced experimental autoimmune encephalomyelitis (EAE) experiment.

The Interleukin 10 (IL-10) levels observed for the different experimental groups, presented as mean±SEM, are summarized in FIG. 18. No significant changes were observed for IL-10.

Figure 19:
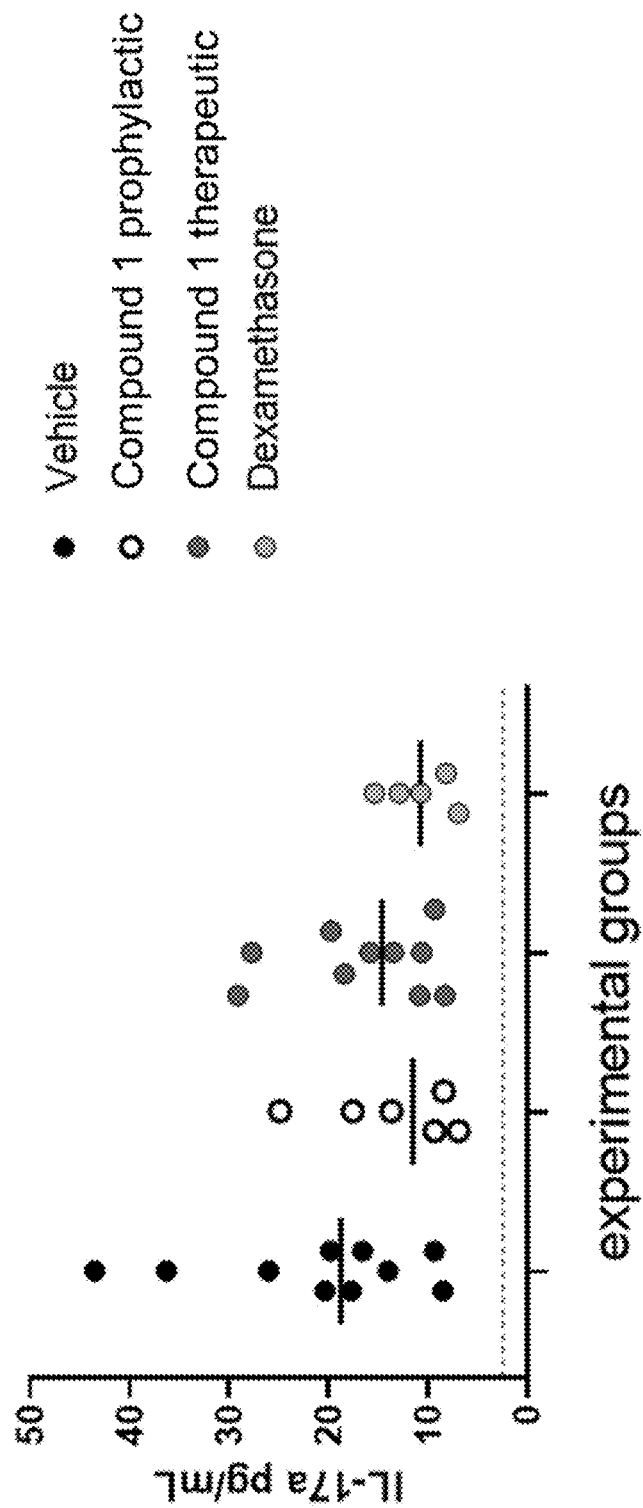
FIG. 19 shows the Interleukin 17a (IL-17a) levels observed for the different experimental groups in the mouse model of myelin oligodendrocyte glycoprotein (MOG)-induced experimental autoimmune encephalomyelitis (EAE) experiment.

The Interleukin 17a (IL-17a) levels observed for the different experimental groups, presented as mean±SEM, are summarized in FIG. 19. IL-17a showed a similar trend to IFN-$\gamma$, with a reduction in the dexamethasone group and slight reductions in both treatment groups. However, overall, none of these changes reached significance.

Figure 20:
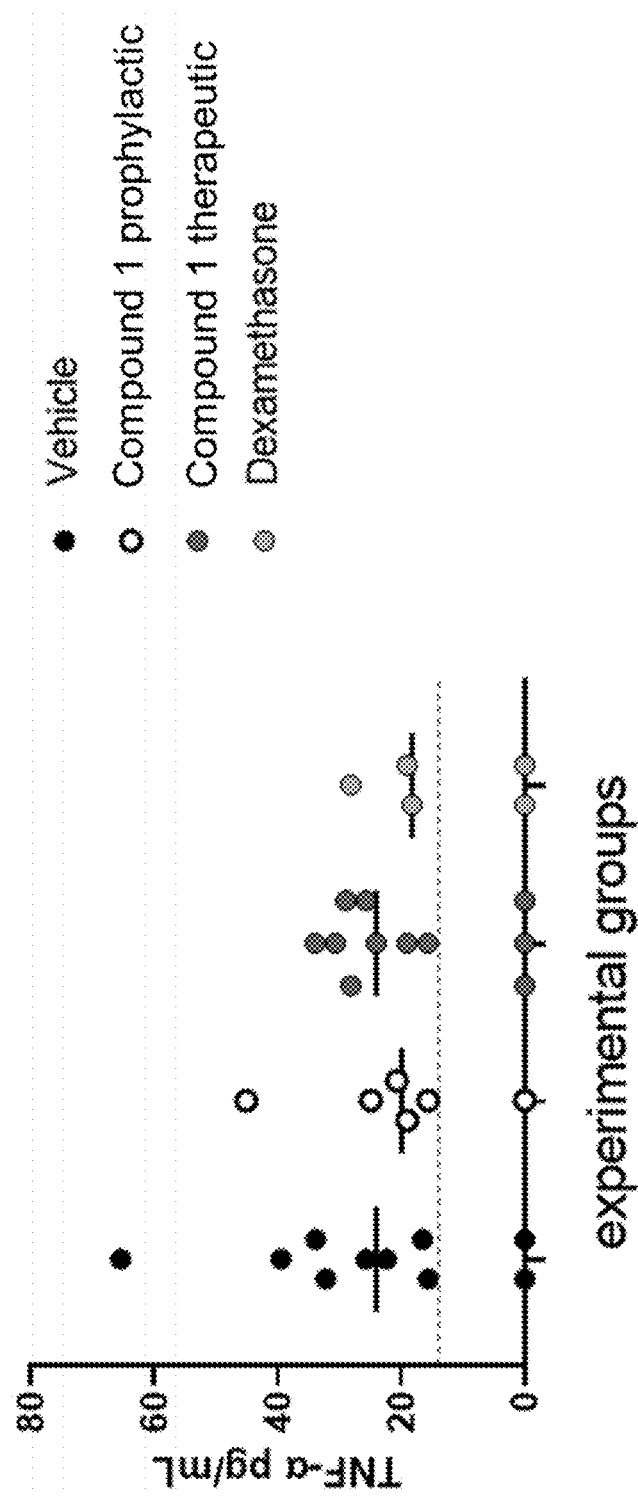
FIG. 20 shows the tumor necrosis factor α (TNF-α) levels observed for the different experimental groups in the mouse model of myelin oligodendrocyte glycoprotein (MOG)-induced experimental autoimmune encephalomyelitis (EAE) experiment.

The tumor necrosis factor $\alpha$ (TNF-$\alpha$) levels observed for the different experimental groups, presented as mean±SEM, are summarized in FIG. 20. Prophylactic Compound 1 and dexamethasone induced very slight decreases in TNF-$\alpha$. However, none of the changes were statistically significant.

In the present study, all animals developed signs of EAE 7 days after disease induction by immunization with $MOG_{35-55}$. The efficacy of Compound 1 was tested in the model by using a prophylactic approach (group 2, treatments started on day 1) and a therapeutic approach (group 3, treatment initiated on day 8). The prophylactic treatment with Compound 1 did not prevent or improve the clinical EAE profile when the effects were analyzed over time or when the overall effect was investigated using AUC analysis. On the contrary, the therapeutic administration of Compound 1 statistically significantly ameliorated the disease profile at earlier time points (day 13 and 14) and again at later stages (days 22-25) which are normally associated with a more neurodegenerative mechanism. Compound 1 therapeutic treatment also showed a trend towards a reduced AUC value as compared to the vehicle AUC. As expected, treatment with the positive control dexamethasone statistically significantly reduced the EAE scores (days 8-25) as well as the clinical profile compared to vehicle, as assessed by AUC. This corticosteroid was used as a positive control based on validation data for this model and on several independent studies showing the efficacy of dexamethasone treatments in EAE. Notably, the animals treated with Compound 1 in a therapeutic manner showed a significant remission of the symptoms, and ~27% of the animals remised to zero. Whilst plasma cytokine levels did not show any significant differences between the vehicle and treatment groups, there was a general trend towards decreasing levels in the treatment groups for some cytokines such as IFN-γ, IL-17a, and TNF-α.

Example 11: Efficacy of Various Doses of Compound 1 in a Mouse Model of Myelin Oligodendrocyte Glycoprotein (MOG)-Induced Experimental Autoimmune Encephalomyelitis (EAE)

60 female C57BL/6 mice were housed for an acclimation period of 1 week. 53 mice were enrolled in the study after randomization with a body weight between 18.3-22.3 g with an average body weight of 19.7 g per group on Study day minus 1.

For induction of MOG-EAE, $MOG_{35-55}$ peptide was administered in phosphate buffered saline (PBS) and complete Freund's adjuvant (CFA). $MOG_{35-55}$ peptide in PBS was emulsified in a 1:1 (v:v) mixture with CFA via homogenization in an Omni BeadRuptor Elite using 7 mL tubes pre-filled with 2.8 mm ceramic beads. Briefly, $MOG_{35-55}$ peptide was brought up to 1 mg/mL in cold PBS, and 1.75 mL aliquoted into each homogenization tube. An equal volume (1.75 mL) CFA was then added for a total volume of 3.5 mL, on ice. Two rounds of homogenization were performed using a speed of 3.5 m/s; 3 cycles of 45 seconds with 30 seconds dwell at 4° C., followed by a third round with 2 cycles of 45 seconds and 30 seconds dwell at 4° C. In between each round, samples were placed on ice for ~15 minutes. Tubes were spun down at 300 g for 1 minute at 4° C. Mice were anesthetized under isoflurane anesthesia. 100 μL (50 μg $MOG_{35-55}$) was then injected subcutaneously into the flank of each leg (for a total of two injections and 100 μg $MOG_{35-55}$). On Study Day 0 and Day 2, pertussis toxin was formulated at a concentration of 2 ng/4 in PBS, and 100 μL (200 ng) injected into each animal by intraperitoneal injection.

Treatments were administered according to the administration schedule shown in Table 5.

| Group | Treatment Description | N | Test Article Dose (mg/kg) | Dose Volume (mL/kg) | Dose Route | Dosing Frequency & Duration |
|---|---|---|---|---|---|---|
| 1 | Naïve (no treatment) | 5 | N/A | N/A | N/A | NA |
| 2 | Vehicle | 12 | 0 | 5 | PO | BID, day 1-28 |
| 3 | Compound 1 | 12 | 75 | 5 | PO | BID, day 1-28 |
| 4 | Compound 1 | 12 | 25 | 5 | PO | BID, day 1-28 |
| 5 | Vehicle | 12 | 0 | 5 | PO | AM, day 1-28 |
|   | Compound 1 |   | 100 | 5 | PO | PM, day 1-28 |

Treatment was performed BID starting on Day 1 for groups 2, 3, and 4, and once daily (QD) starting on day 1 for group 5. All experimental groups were n=12. The administration interval was 12 hours and the administration volume was 5 mL/kg.

Figure 21:
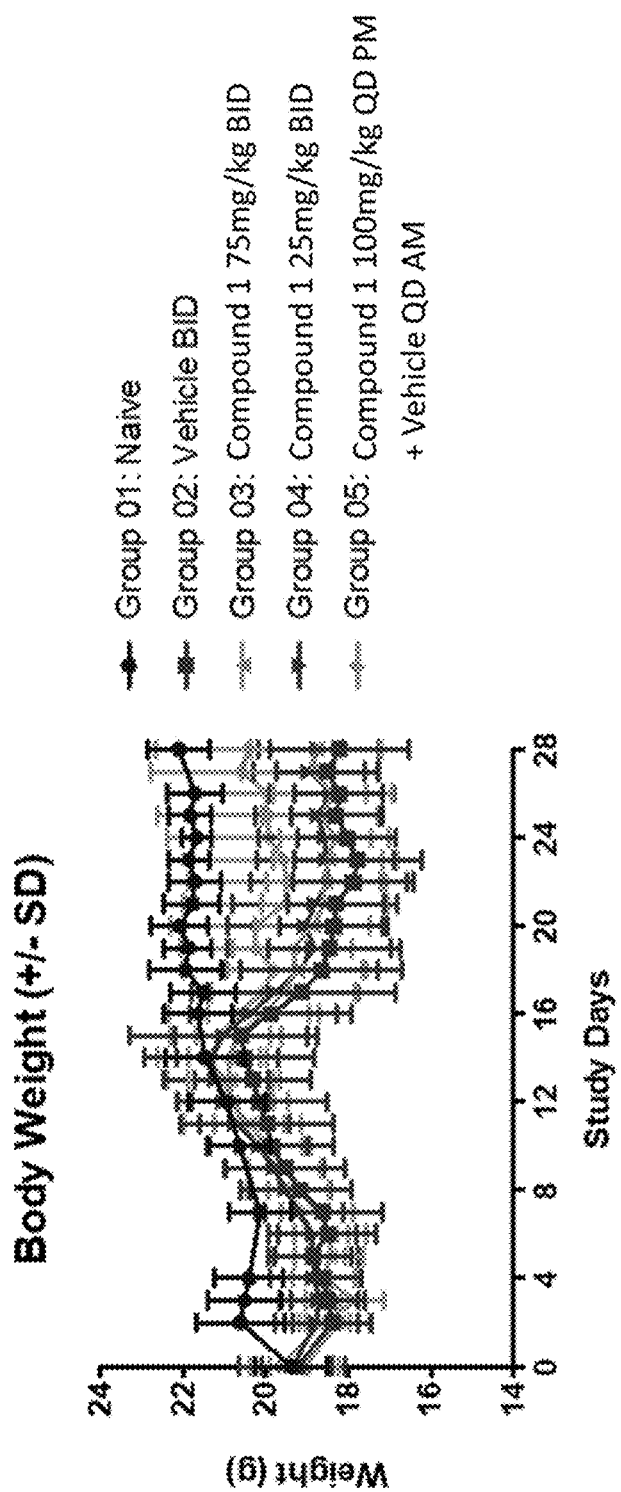
FIG. 21 shows the changes in mouse body weight observed for the different experimental groups over the course of the variable dose mouse model of myelin oligodendrocyte glycoprotein (MOG)-induced experimental autoimmune encephalomyelitis (EAE) experiment.
Figure 22:
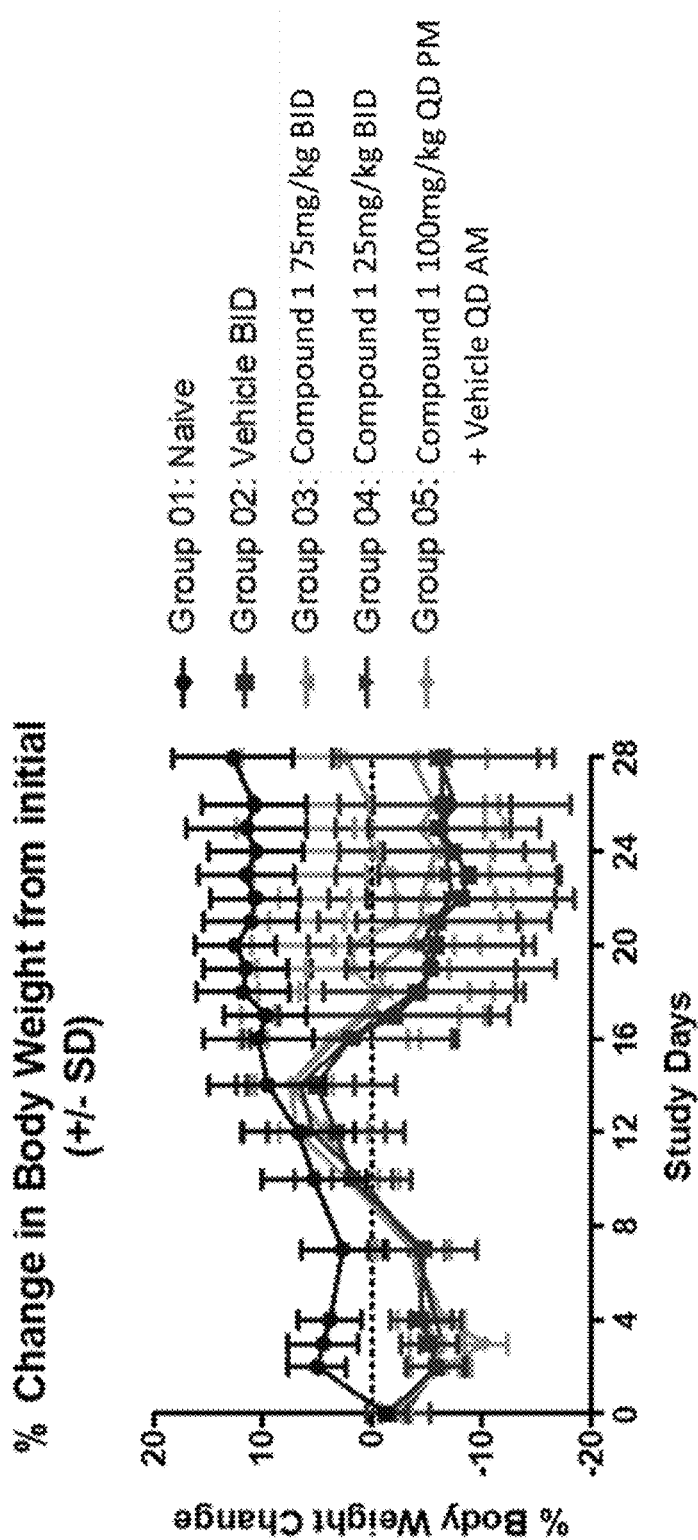
FIG. 22 shows the percent body weight change observed for the different experimental groups over the course of the variable dose mouse model of myelin oligodendrocyte glycoprotein (MOG)-induced experimental autoimmune encephalomyelitis (EAE) experiment.

Body weight measurements were taken daily for all animals except for study days 5, 6, 8, 9, 11 and 27 when the body weights were not recorded by mistake in the control group (naïve mice). The changes in body weight observed over the course of the experiment for the different experimental groups, presented as mean±SD, are summarized in FIG. 21. The percent body weight changes versus baseline observed over the course of the experiment for the different experimental groups, presented as mean±SD, are summarized in FIG. 22. As compared to Group 2 (Vehicle), Group 5 (Compound 1, 100 mg/kg, QD) showed significantly less body weight loss towards the end of the study, on study Days 19-20 and then from study day 22 onward until study termination on day 28. Group 2 had significantly lower body weights when compared to Group 1 (naïve animals) on study Days 2 and 3 ($p<0.05$), day 17 ($p<0.01$), Day 18 ($p<0.001$) and Days 19-28 ($p<0.0001$).

Figure 24:
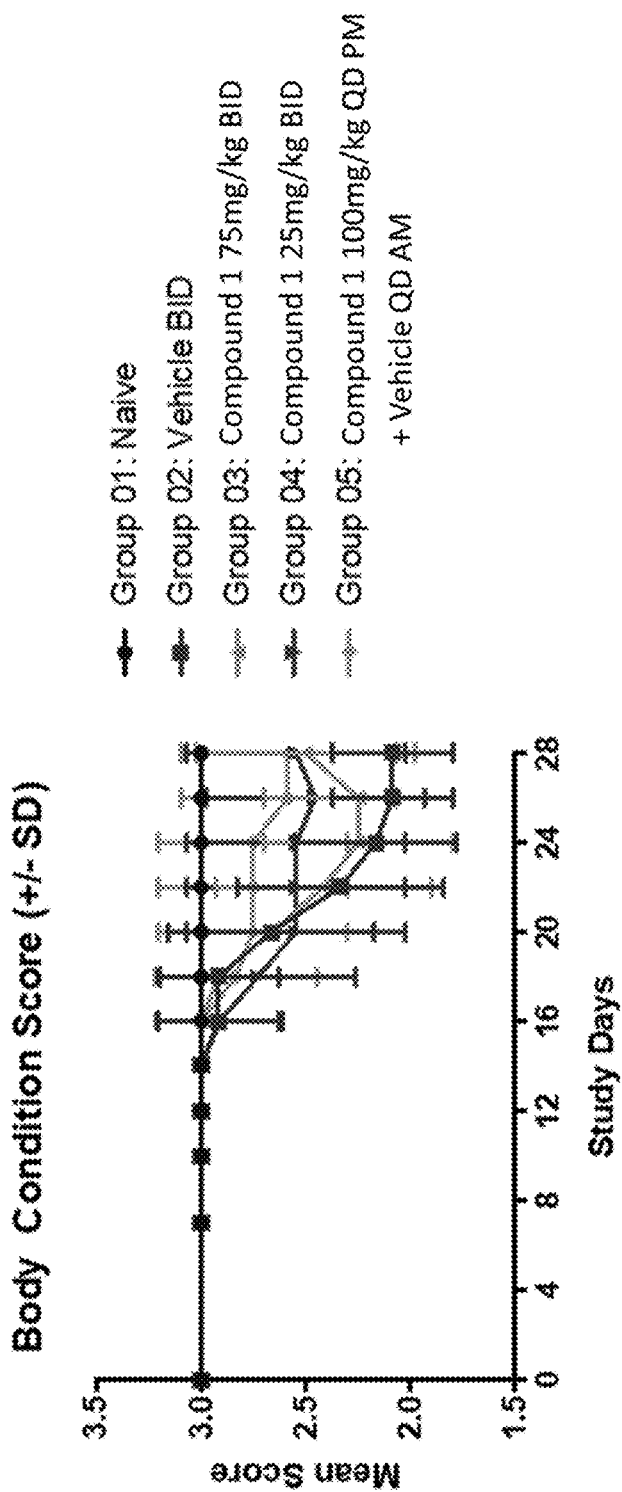
FIG. 24 shows the mean body condition scores observed for the different experimental groups over the course of the variable dose mouse model of myelin oligodendrocyte glycoprotein (MOG)-induced experimental autoimmune encephalomyelitis (EAE) experiment.

The Body condition score of all animals was monitored on study Days 0, 7, 10 and then every other day. Body condition scoring was conducted according to the scale shown in FIG. 23. The mean body condition scores observed over the course of the experiment for the different experimental groups, presented as mean±SD, are summarized in FIG. 24. Group 5 showed statistically significant improvement in comparison to animals from Group 2 on Day 22 ($p<0.01$), Day 24 ($p<0.0001$), Days 26 and 28 (*$p<0.001$). Group 4 showed a statistically significant effect vs. Group 2 on study Days 24 and 26 (*$p<0.05$), and Day 28 ($p<0.01$). Group 3 only showed a statistically significant reduction in body condition scores on study Day 28 ($p<0.01$). Group 2 had significantly lower body condition scores than Group 1 on Day 22 (*$p<0.001$) and Day 24-28 (**$p<0.0001$).

Disease severity was scored on Day 0, 7 and every 2 days beginning on Day 10 onward for all groups. The following scale was used:
(0) normal;
(1) loss of tail tone;
(2) loss of tail tone and hind limb weakness;
(3) severe weakness in both limbs/single limb, paralysis;
(4) paralysis of 2 or more limbs;
(5) death.

Figure 25:
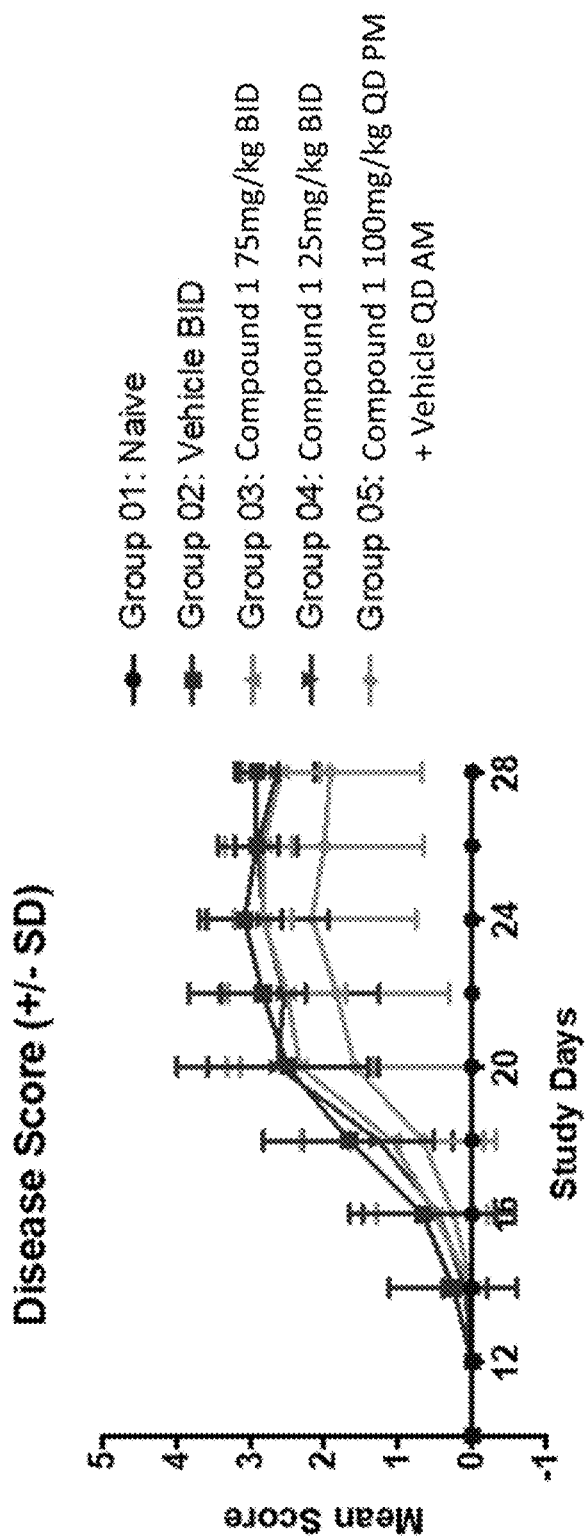
FIG. 25 shows the mean disease scores observed for the different experimental groups over the course of the variable dose mouse model of myelin oligodendrocyte glycoprotein (MOG)-induced experimental autoimmune encephalomyelitis (EAE) experiment.

The mean disease scores observed over the course of the experiment for the different experimental groups, presented as mean±SD, are summarized in FIG. 25. The mean disease score per group was calculated by averaging the individual disease scores in each group. Starting from day 14-18 disease severity increased in all groups. Disease severity was statistically significantly lower in Group 5 receiving 100 mg/kg of Compound 1 in comparison to the vehicle group from study day 18 to 28.

Figure 26:
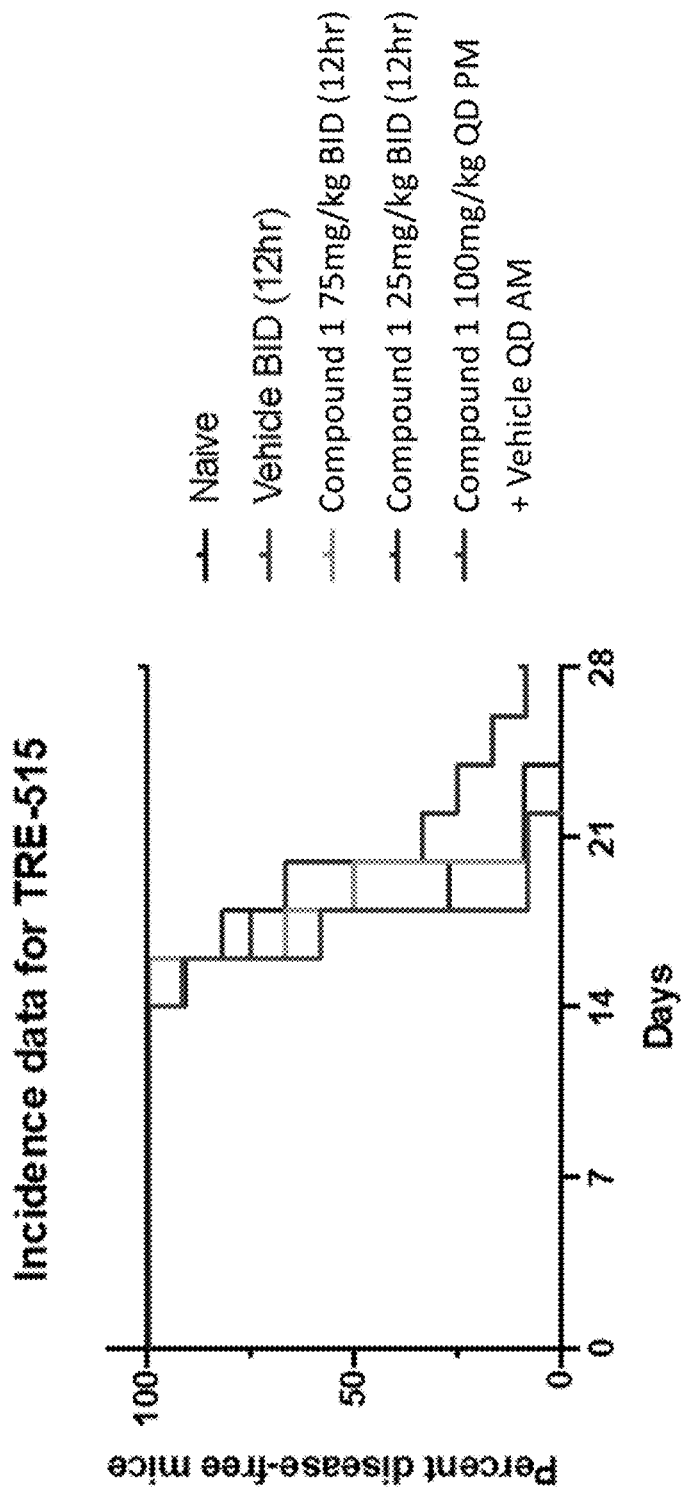
FIG. 26 shows the percentage of disease-free animals observed for the different experimental groups over the course of the variable dose mouse model of myelin oligodendrocyte glycoprotein (MOG)-induced experimental autoimmune encephalomyelitis (EAE) experiment.

Disease incidence rate was calculated as percentage of total animals per group starting from day 0 until termination on study day 28. The percentages of disease-free mice observed over the course of the experiment for the different experimental groups are summarized in FIG. 26. Group 5 showed lower incidence rate and later disease onset. A Log-rank (Mantel-Cox) test comparing Vehicle BID, Compound 1 75 mg/kg BID, Compound 1 25 mg/kg BID, and Compound 1 100 mg/kg QD gives a p-value of 0.039 with median time to disease of 18 days, 19 days, 18 days, and 20 days, respectively.

Figure 27:
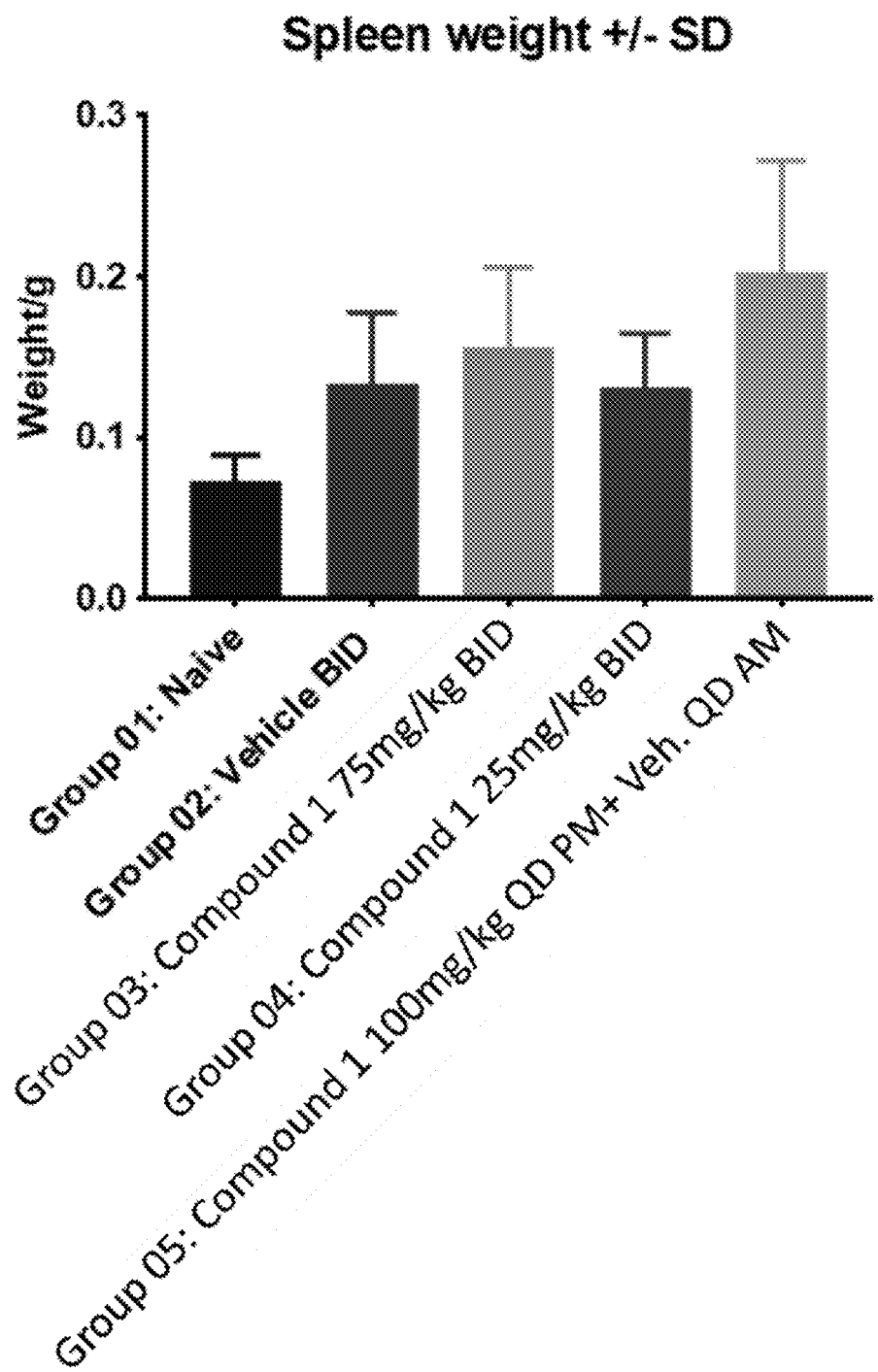
FIG. 27 shows the spleen weights observed for the different experimental groups in the variable dose mouse model of myelin oligodendrocyte glycoprotein (MOG)-induced experimental autoimmune encephalomyelitis (EAE) experiment.

The spleen weights of all mice and all groups were determined on study Day 28 during necropsy. The spleen weights observed for the different experimental groups, presented as mean±SEM, are summarized in FIG. 27. Group 5 showed significantly higher spleen weights in comparison to group 2.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a crystalline form of a compound of Formula I:

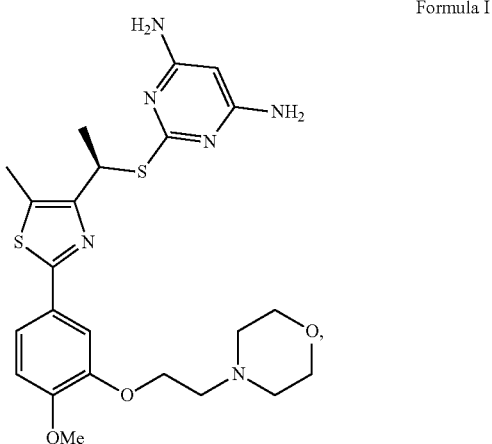 [SMILES: COc1ccc(-c2nc([C@@H](C)Sc3nc(N)cc(N)n3)c(C)s2)cc1OCCN1CCOCC1]

Formula I wherein the crystalline form is a polymorph Form II of a maleate salt of the compound of Formula I, and wherein the polymorph Form II is characterized by an X-ray powder diffraction pattern comprising a peak at 7.6±0.2° 2-θ, 8.7±0.2° 2-θ, or 16.0±0.2° 2-θ, as measured by X-ray powder diffraction using an X-ray wavelength of 1.5406 Å.

2. The composition of claim 1, wherein the polymorph Form II is characterized by an X-ray powder diffraction pattern comprising peaks at 7.6±0.2° 2-θ, 8.7±0.2° 2-θ, and 16.0±0.2° 2-θ, as measured by X-ray powder diffraction using an X-ray wavelength of 1.5406 Å.

3. The composition of claim 1, wherein the X-ray powder diffraction pattern further comprises at least one peak selected from 12.2±0.2° 2-θ, 17.6±0.2° 2-θ, and 19.5±0.2° 2-θ, as measured by X-ray powder diffraction using an X-ray wavelength of 1.5406 Å.

4. The composition of claim 1, wherein the X-ray powder diffraction pattern further comprises at least one peak selected from 21.7±0.2° 2-θ, 10.8±0.2° 2-θ, and 13.4±0.2° 2-θ, as measured by X-ray powder diffraction using an X-ray wavelength of 1.5406 Å.

5. The composition of claim 1, wherein the X-ray powder diffraction pattern comprises at least five peaks selected from 7.6±0.2° 2-θ, 8.7±0.2° 2-θ, 16.0±0.2° 2-θ, 12.2±0.2° 2-θ, 17.6±0.2° 2-θ, 19.5±0.2° 2-θ, 21.7±0.2° 2-θ, 10.8±0.2° 2-θ, and 13.4±0.2° 2-θ, as measured by X-ray powder diffraction using an X-ray wavelength of 1.5406 Å.

6. The composition of claim 1, wherein the polymorph Form II is characterized by an X-ray powder diffraction pattern substantially as set forth in FIG. 5.

7. The composition of claim 1, wherein the polymorph Form II is characterized by a differential scanning calorimetry (DSC) thermogram comprising an endotherm in the range of about 150° C. to about 170° C.

8. The composition of claim 1, wherein the polymorph Form II is characterized by a DSC thermogram comprising an endotherm in the range of about 25° C. to about 80° C.

9. The composition of claim 1, wherein the polymorph Form II is characterized by a DSC thermogram comprising an endotherm in the range of about 25° C. to about 60° C.

10. The composition of claim 1, wherein the polymorph Form II is characterized by a DSC thermogram substantially as set forth in FIG. 4.

11. The composition of claim 1, wherein the polymorph Form II has a melting point in the range of about 150 to about 155° C.

12. The composition of claim 1, wherein the polymorph Form II comprises acicular needle-like particles ranging in size from about 1 μm to about 100 μm.

13. The composition of claim 1, wherein the polymorph Form II comprises acicular needle-like particles ranging in size from about 1 μm to about 50 μm.

14. The composition of claim 1, wherein the polymorph Form II is characterized by a thermogravimetric analysis (TGA) thermogram comprising a loss in mass of about 1% to about 5% over a temperature range of about 25 to about 80° C.

15. The composition of claim 1, wherein the polymorph Form II is characterized by a TGA thermogram comprising a loss in mass of about 0% to about 1% over a temperature range of about 70 to about 130° C.

16. The composition of claim 1, wherein the polymorph Form II is characterized by a TGA thermogram substantially as set forth in FIG. 6.

17. The composition of claim 1, wherein the polymorph Form II comprises less than 5% water.

18. A pharmaceutical composition comprising the composition of claim 1 and a pharmaceutically acceptable excipient.

19. A method of treating a disease or disorder in a subject in need thereof, comprising administering to the subject a therapeutically effective amount of the pharmaceutical composition of claim 18.

20. The method of claim 19, wherein the disease or disorder comprises a solid tumor or autoimmune disease.

21. The method of claim 19, wherein the disease or disorder comprises optic neuritis or acute disseminated encephalomyelitis.

22. The method of claim 19, wherein the pharmaceutical composition is administered once daily, twice daily, or 12 hours apart.

23. The method of claim 19, wherein the administration of the pharmaceutical composition results in a decrease in interferon gamma (IFNγ) levels in the subject.

* * * * *